US012703877B2

(12) United States Patent
Khlystov

(10) Patent No.: US 12,703,877 B2
(45) Date of Patent: Aug. 11, 2026

(54) METHODS AND SYSTEMS TO SECRETE LIGNIN-MODIFYING ENZYMES AND USES THEREOF

(71) Applicant: The Board of Trustees of the Leland Stanford Junior University, Stanford, CA (US)

(72) Inventor: Nikita A. Khlystov, Los Altos Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 774 days.

(21) Appl. No.: 18/000,797

(22) PCT Filed: Jun. 7, 2021

(86) PCT No.: PCT/US2021/036248

§ 371 (c)(1),
(2) Date: Dec. 5, 2022

(87) PCT Pub. No.: WO2021/248137

PCT Pub. Date: Dec. 9, 2021

(65) Prior Publication Data

US 2023/0313257 A1 Oct. 5, 2023

Related U.S. Application Data

(60) Provisional application No. 63/035,172, filed on Jun. 5, 2020.

(51) Int. Cl.

| | |
|---|---|
| ***C12N 1/19*** | (2006.01) |
| ***C12N 1/185*** | (2026.01) |
| ***C12N 9/08*** | (2006.01) |
| ***C12N 15/10*** | (2006.01) |
| ***C12N 15/81*** | (2006.01) |
| ***C12P 21/02*** | (2006.01) |
| *C12R 1/865* | (2006.01) |

(52) U.S. Cl.

CPC .............. *C12P 21/02* (2013.01); *C12N 1/185* (2021.05); *C12N 9/0065* (2013.01); *C12N 15/1037* (2013.01); *C12N 15/81* (2013.01); *C12Y 111/01007* (2013.01); *C12R 2001/865* (2021.05)

(58) Field of Classification Search

None

See application file for complete search history.

(56) References Cited

U.S. PATENT DOCUMENTS

| | | | |
|---|---|---|---|
| 6,617,435 | B2 | 9/2003 | Turpen et al. |
| 8,236,551 | B2 | 8/2012 | Dhawan et al. |
| 9,441,214 | B2 | 9/2016 | Schoonneveld-Bergmans et al. |
| 10,472,688 | B2 | 11/2019 | Lau et al. |
| 10,655,115 | B2 | 5/2020 | Los et al. |
| 11,312,753 | B2 | 4/2022 | Khlystov et al. |
| 2008/0235830 | A1 | 9/2008 | Sticklen et al. |
| 2009/0275481 | A1 | 11/2009 | Wang et al. |
| 2012/0079627 | A1 | 3/2012 | Gampala et al. |
| 2017/0233753 | A1 | 8/2017 | Parrow et al. |
| 2020/0095291 | A1* | 3/2020 | Khlystov ............ C07K 14/375 |
| 2020/0299742 | A1 | 9/2020 | Huang et al. |

FOREIGN PATENT DOCUMENTS

| | | |
|---|---|---|
| WO | 2021248137 A2 | 12/2021 |
| WO | 2021248137 A3 | 12/2021 |

OTHER PUBLICATIONS

Krainer et al., "Optimizing cofactor availability for the production of recombinant heme peroxidase in Pichia pastoris," Microbial Cell Factories 14:4, 2015, 9 pages (Year: 2015).*

Lipovšek et al., "Selection of Horseradish Peroxidase Variants with Enhanced Enantioselectivity by Yeast Surface Display," Chem. Biol. 14:1176-1185, 2007 (Year: 2007).*

Sun et al., "Display of Heterologous Proteins on the *Saccharomyces cerevisiae*Surface Display System Using a Single Constitutive Expression Vector," Biotechnol. Prog. 30:44-450, 2014 (Year: 2014).*

Yang et al., "Model Compounds Study for the Mechanism of Horseradish Peroxidase-Catalyzed Lignin Modification," Appl. Biochem. Biotechnol. 191:981-995, Jan. 2020 (Year: 2020).*

Liu et al., "Improved production of a heterologous amylase in *Saccharomyces cerevisiae* by inverse metabolic engineering," Appl. Environ. Microbiol. 80:5542-5550, 2014 (Year: 2014).*

Colby et al., "Engineering antibody affinity by yeast surface display," Methods Enzymol. 388:348-358, 2004 (Year: 2004).*

Wang et al., "Systematic screening of glycosylation- and trafficking-associated gene knockouts in *Saccharomyces cerevisiae* identifies mutants with improved heterologous exocellulase activity and," BMC Biotechnol. 13:71, 2013, 14 pages (Year: 2013).*

Bao et al., "Are mutations usually deleterious? A perspective on the fitness effects of mutation accumulation," Evolutionary Ecology 36:753-766, 2022 (Year: 2022).*

Singh et al., Curr. Protein Pept. Sci. 18:1-11, 2017 (Year: 2017).*

Zhang et al., Structure 26:1474-1485, 2018 (Year: 2018).*

(Continued)

*Primary Examiner* — David Steadman

(74) *Attorney, Agent, or Firm* — KPPB LLP

(57) ABSTRACT

Embodiments of the invention are generally directed to lignin-modifying enzymes and systems and methods of their manufacture. In many embodiments, yeast strains, including *S. cerevisiae*, are used to produce and secrete lignin-modifying enzymes Further embodiments are directed to methods to screening peroxidase-producing yeast strains, including *S. cerevisiae*. Additional embodiments are directed to an expression vector or cassette encoding for a protein of interest and one or more proteins to allow for surface to display of the protein of interest.

5 Claims, 8 Drawing Sheets

Specification includes a Sequence Listing.

(56) References Cited

OTHER PUBLICATIONS

Peng et al., "Controlling heterologous gene expression in yeast cell factories on different carbon substrates and across the diauxic shift: a comparison of yeast promoter activities," Microb. Cell Fact. 14:91, 2015, 11 pages (Year: 2015).*
International Preliminary Report on Patentability received for International Application PCT/US2021/036248, Report issued Dec. 6, 2022, Mailed on Dec. 15, 2022, 9 pgs.
International Search Report and Written Opinion received for International Application No. PCT/US2021/036248, Search completed Nov. 9, 2021, Mailed Dec. 7, 2021, 29 pgs.
Ahmad et al., "Development of novel assays for lignin degradation: comparative analysis of bacterial and fungal lignin degraders", Molecular BioSystems, vol. 6, No. 5, 2010, pp. 815-821, doi: 10.1039/B908966G.
Antipov et al., "Highly L and D enantioselective variants of horseradish peroxidase discovered by an ultrahigh-throughput selection method", Proceedings of the National Academy of Sciences, vol. 105, No. 46, Nov. 18, 2008, pp. 17694-17699, doi: 10.1073/pnas.0809851105.
Austin et al., "Production and field performance of transgenic alfalfa (*Medicago sativa* L.) expressing alpha-amylase and manganese-dependent lignin peroxidase", Euphytica, vol. 85, Feb. 1995, pp. 381-393, doi: 10.1007/BF00023971.
Bao et al., "Direct over-expression, characterization and H2O2 stability study of active Pleurotus eryngii versatile peroxidase in *Escherichia coli*", Biotechnology Letters, vol. 34, Aug. 2012, pp. 1537-1543, doi: 10.1007/s10529-012-0940-5.
Barr et al., "Pyridine Hemochromagen Assay for Determining the Concentration of Heme in Purified Protein Solutions", Bio-Protocol, vol. 5, No. 18, Sep. 20, 2015, 7 pgs., doi: 10.21769/BioProtoc.1594.
Berthet et al., "Disruption of LACCASE4 and 17 Results in Tissue-Specific Alterations to Lignification of *Arabidopsis thaliana* Stems", The Plant Cell, vol. 23, No. 3, Mar. 2011, pp. 1124-1137, doi: 10.1105/tpc.110.082792.
Chanoca et al., "Lignin Engineering in Forest Trees", Frontiers in Plant Science, vol. 10, Article 912, Jul. 25, 2019, 13 pgs., doi: 10.3389/fpls.2019.00912.
Cherf et al., "Applications of Yeast Surface Display for Protein Engineering", Methods in Molecular Biology, Chapter—8, vol. 1319, 2015, pp. 155-175, doi: 10.1007/978-1-4939-2748-7_8.
Chinowski et al., "The Crystal Structure of Lignin Peroxidase at 1.70 Å Resolution Reveals a Hydroxy Group on the Cβ of Tryptophan 171: A Novel Radical Site Formed During the Redox Cycle", Journal of Molecular Biology, vol. 286, No. 3, Feb. 26, 1999, pp. 809-827, doi: 10.1006/jmbi.1998.2507.
Clough et al., "Manganese peroxidase from the white-rot fungus *Phanerochaete chrysosporium* is enzymatically active and accumulates to high levels in transgenic maize seed", Plant Biotechnology Journal, vol. 4, No. 1, 2005, pp. 53-62, doi: 10.1111/j.1467-7652.2005.00157.x.
Conesa et al., "Studies on the Production of Fungal Peroxidases in Aspergillus niger", Applied and Environmental Microbiology, vol. 66, No. 7, Jul. 2000, pp. 3016-3023, doi: 10.1128/AEM.66.7.3016-3023.2000.
Daniel et al., "Pyranose Oxidase, a Major Source of H2O2 during Wood Degradation by Phanerochaete chrysosporium, Trametes versicolor, and Oudemansiella mucida", Applied and Environmental Microbiology, vol. 60, No. 7, Jul. 1994, pp. 2524-2532, doi: 10.1128/aem.60.7.2524-2532.1994.
De Ruijter et al., "Enhancing antibody folding and secretion by tailoring the *Saccharomyces cerevisiae* endoplasmic reticulum", Microbial Cell Factories, vol. 15, Article 87, May 23, 2016, 18 pgs., doi: 10.1186/s12934-016-0488-5.
Delic et al., "Engineering of Protein Folding and Secretion-Strategies to Overcome Bottlenecks for Efficient Production of Recombinant Proteins", Antioxidants & Redox Signaling, vol. 21, No. 3, 2014, pp. 414-437, doi: 10.1089/ars.2014.5844.
Feizi et al., "Genome-Scale Modeling of the Protein Secretory Machinery in Yeast", PLoS ONE, vol. 8, No. 5, e63284, May 2013, 13 pgs., doi: 10.1371/journal.pone.0063284.
Fernandez-Fueyo et al., "Lignin-degrading Peroxidases from Genome of Selective Ligninolytic Fungus *Ceriporiopsis subvermispora*", The Journal of Biological Chemistry, vol. 287, No. 20, May 11, 2012, pp. 16903-16916, doi: 10.1074/jbc.M112.356378.
Fernandez-Fueyo et al., "Ligninolytic peroxidase genes in the oyster mushroom genome: heterologous expression, molecular structure, catalytic and stability properties, and lignin-degrading ability", Biotechnology for Biofuels, vol. 7, Article 2, Jan. 3, 2014, 23 pgs., doi: 10.1186/1754-6834-7-2.
Garcia-Ruiz et al., "Directed evolution of a temperature-, peroxide- and alkaline pH-tolerant versatile peroxidase", Biochemical Journal, vol. 441, No. 1, 2012, pp. 487-498, doi: 10.1042/BJ20111199.
Giaever et al., "Functional profiling of the *Saccharomyces cerevisiae* genome", Nature, vol. 418, Jul. 25, 2002, pp. 387-391, doi: 10.1038/nature00935.
Gonzalez-Perez et al., "Assembly of evolved ligninolytic genes in *Saccharomyces cerevisiae*", Bioengineered, vol. 5, No. 4, Jul./Aug. 2014, pp. 254-263, doi: 10.4161/bioe.29167.
Gonzalez-Perez et al., "The making of versatile peroxidase by directed evolution", Biocatalysis and Biotransformation, vol. 36, No. 1, Aug. 16, 2017, 11 pgs., doi: 10.1080/10242422.2017.1363190.
Goodin et al., "Nicotiana benthamiana: Its History and Future as a Model for Plant-Pathogen Interactions", Molecular Plant-Microbe Interactions, vol. 21, No. 8, 2008, pp. 1015-1026, doi: 10.1094/MPMI-21-8-1015.
Goodin et al., "pGD vectors: versatile tools for the expression of green and red fluorescent protein fusions in agroinfiltrated plant leaves", The Plant Journal, vol. 31, No. 3, 2002, pp. 375-383, doi: 10.1046/j.1365-313X.2002.01360.x.
Guillen et al., "Hydrogen-peroxide-producing system of Pleurotus eryngii involving the extracellular enzyme aryl-alcohol oxidase", Applied Microbiology and Biotechnology, vol. 41, Jun. 1994, pp. 465-470, doi: 10.1007/BF00939037.
Hammel et al., "Ligninolysis by a Purified Lignin Peroxidase", The Journal of Biological Chemistry, vol. 268, No. 17, Jun. 15, 1993, pp. 12274-12281, doi: 10.1016/S0021-9258(18)31385-1.
Harvey et al., "HEx: A heterologous expression platform for the discovery of fungal natural products", Science Advances, vol. 4, No. 4, eaar5459, Apr. 11, 2018, 14 pgs., doi: 10.1126/sciadv.aar5459.
Hernandez-Ortega et al., "Fungal aryl-alcohol oxidase: a peroxide-producing flavoenzyme involved in lignin degradation", Applied Microbiology and Biotechnology, vol. 93, Jan. 17, 2012, pp. 1395-1410, doi: 10.1007/s00253-011-3836-8.
Hiatt et al., "Production of antibodies in transgenic plants", Nature, vol. 342, Nov. 2, 1989, pp. 76-78, doi: 10.1038/342076a0.
Hoshida et al., "N-glycosylation deficiency enhanced heterologous production of a Bacillus licheniformis thermostable α-amylase in *Saccharomyces cerevisiae*", Applied Microbiology and Biotechnology, vol. 97, Jan. 11, 2013, pp. 5473-5482, doi: 10.1007/s00253-012-4582-2.
Hou et al., "Metabolic engineering of recombinant protein secretion by *Saccharomyces cerevisiae*", FEMS Yeast Research, vol. 12, No. 5, Aug. 2012, pp. 491-510, doi: 10.1111/j.1567-1364.2012.00810.x.
Huang et al., "Microfluidic screening and whole-genome sequencing identifies mutations associated with improved protein secretion by yeast", Proceedings of the National Academy of Sciences, vol. 112, No. 34, Aug. 25, 2015, pp. E4689-E4696, doi: 10.1073/pnas.1506460112.
Idiris et al., "Engineering of protein secretion in yeast: strategies and impact on protein production", Applied Microbiology and Biotechnology, vol. 86, Feb. 2010, pp. 403-417, doi: 10.1007/s00253-010-2447-0.
Isikgor et al., "Lignocellulosic biomass: a sustainable platform for the production of bio-based chemicals and polymers", Polymer Chemistry, vol. 6, No. 25, Jul. 7, 2015, pp. 4497-4559, doi: 10.1039/c5py00263j.

(56) References Cited

OTHER PUBLICATIONS

Janusz et al., "Lignin degradation: microorganisms, enzymes involved, genomes analysis and evolution", FEMS Microbiology Reviews, vol. 41, No. 6, Oct. 27, 2017, pp. 941-962, doi: 10.1093/femsre/fux049.
Kathiresan et al., "Respiration triggers heme transfer from cytochrome c peroxidase to catalase in yeast mitochondria", Proceedings of the National Academy of Sciences, vol. 111, No. 49, Dec. 9, 2014, pp. 17468-17473, doi: 10.1073/pnas.1409692111.
Kersten, "Glyoxal oxidase of Phanerochaete chrysosporium: Its characterization and activation by lignin peroxidase", Proceedings of the National Academy of Sciences, vol. 87, No. 8, Apr. 15, 1990, pp. 2936-2940, doi: 10.1073/pnas.87.8.2936.
Kinnunen et al., "Improved efficiency in screening for lignin-modifying peroxidases and laccases of Basidomycetes", Current Biotechnology, vol. 6, No. 2, 2017, pp. 105-115, doi: 10.2174/2211550105666160330205138.
Kirk et al., "Ligninase of Phanerochaete chrysosporium. Mechanism of its degradation of the non-phenolic arylglycerol β-aryl ether substructure of lignin", Biochemical Journal, vol. 236, No. 1, May 15, 1986, pp. 279-287, doi: 10.1042/bj2360279.
Lambertz et al., "Progress and obstacles in the production and application of recombinant lignin-degrading peroxidases", Bioengineered, vol. 7, No. 3, Jun. 13, 2016, pp. 145-154, doi: 10.1080/21655979.2016.1191705.
Lau et al., "Six enzymes from mayapple that complete the biosynthetic pathway to the etoposide aglycone", Science, vol. 349, No. 6253, Sep. 11, 2015, pp. 1224-1228, doi: 10.1126/science.aac7202.
Li et al., "A lignin-epoxy resin derived from biomass as an alternative to formaldehyde-based wood adhesives", Green Chemistry, vol. 20, No. 7, 2018, pp. 1459-1466, doi: 10.1039/C7GC03026F.
Ligaba-Osena et al., "Reducing biomass recalcitrance by heterologous expression of a bacterial peroxidase in tobacco (*Nicotiana benthamiana*)", Scientific Reports, vol. 7, Article No. 17104, Dec. 6, 2017, 18 pgs., doi: 10.1038/s41598-017-16909-x.
Lin et al., "Functional Expression of Horseradish Peroxidase in *E. coli* by Directed Evolution", Biotechnology Progress, vol. 15, No. 3, 1999, pp. 467-471, doi: 10.1021/bp990037r.
Lopez et al., "Homologous and Heterologous Expression of Basidiomycete Genes Related to Plant Biomass Degradation", Gene Expression Systems in Fungi: Advancements and Applications, Apr. 5, 2016, pp. 119-160, doi: 10.1007/978-3-319-27951-0_5.
Martell et al., "A split horseradish peroxidase for the detection of intercellular protein-protein interactions and sensitive visualization of synapses", Nature Biotechnology, vol. 34, No. 7, Jul. 2016, pp. 774-780, doi: 10.1038/nbt.3563.
Martinez et al., "Genome sequence of the lignocellulose degrading fungus Phanerochaete chrysosporium strain RP78", Nature Biotechnology, vol. 22, No. 6, Jun. 2004, pp. 695-700, doi: 10.1038/nbt967.
Martinez et al., "Purification and catalytic properties of two manganese peroxidase isoenzymes from Pleurotus eryngii", European Journal of Biochemistry, vol. 237, No. 2, 1996, pp. 424-432, doi: 10.1111/j.1432-1033.1996.0424k.x.
Martinez et al., "Senescence-Related Changes in the Leaf Apoplast", Journal of Plant Growth Regulation, vol. 33, Mar. 2014, pp. 44-55, doi: 10.1007/s00344-013-9395-8.
Michener et al., "Identification and treatment of heme depletion attributed to overexpression of a lineage of evolved P450 monooxygenases", Proceedings of the National Academy of Sciences, vol. 109, No. 47, Nov. 20, 2012, pp. 19504-19509, doi: 10.1076/pnas31212287109.
Min et al., "A dye-decolorizing peroxidase from Bacillus subtilis exhibiting substrate-dependent optimum temperature for dyes and b-ether lignin dimer", Scientific Reports, vol. 5, Article No. 8425, Feb. 2015, 8 pgs., doi: 10.1038/srep08245.
Mnich et al., "Degradation of lignin β-aryl ether units in *Arabidopsis thaliana* expressing LigD, LigF and LigG from Sphingomonas paucimobilis SYK-6", Plant Biotechnology Journal, vol. 15, No. 5, 2017, pp. 581-593, doi: 10.1038/srep08245.
Morawski et al., "Functional expression of horseradish peroxidase in *Saccharomyces cerevisiae* and Pichia pastoris", Protein Engineering, vol. 13, No. 5, May 2000, pp. 377-384, doi: 10.1093/protein/13.5.377.
O'Leary et al., "The Infiltration-centrifugation Technique for Extraction of Apoplastic Fluid from Plant Leaves Using Phaseolus vulgaris as an Example", Journal of Visualized Experiments, vol. 94, No. e52113, Dec. 19, 2014, 8 pgs., doi: 10.3791/52113.
Priefert et al., "Biotechnological production of vanillin", Applied Microbiology and Biotechnology, vol. 56, Aug. 2001, pp. 296-314, doi: 10.1007/s002530100687.
Ragauskas et al., "Lignin Valorization: Improving Lignin Processing in the Biorefinery", Science, vol. 344, No. 6185, May 16, 2014, pp. 1246843-1-1246843-10, doi: 10.1126/science.1246843.
Ragauskas et al., "The Path Forward for Biofuels and Biomaterials", Science, vol. 311, No. 5760, Jan. 27, 2006, pp. 484-489, doi: 10.1126/science.1114736.
Rakestraw et al., "Directed Evolution of a Secretory Leader for the Improved Expression of Heterologous Proteins and Full-Length Antibodies in *Saccharomyces cerevisiae*", Biotechnology and Bioengineering, vol. 103, No. 6, Apr. 15, 2009, pp. 1192-1201, doi: 10.1002/bit.22338.
Riley et al., "Comparative genomics of biotechnologically important yeasts", Proceedings of the National Academy of Sciences, vol. 113, No. 35, Aug. 30, 2016, pp. 9882-9887, doi: 10.1073/pnas.1603941113.
Riley et al., "Extensive sampling of basidiomycete genomes demonstrates inadequacy of the white-rot/brown-rot paradigm for wood decay fungi", Proceedings of the National Academy of Sciences, vol. 111, No. 27, Jul. 8, 2014, pp. 9923-9928, doi: 10.1073/pnas.1400592111.
Robinson et al., "Design and Analysis of Bar-seq Experiments", G3 Genes | Genomes | Genetics, vol. 4, No. 1, Jan. 2014, pp. 11-18, doi: 10.1534/g3.113.008565.
Rodriguez-Limas et al., "Blocking endocytotic mechanisms to improve heterologous protein titers in *Saccharomyces cerevisiae*", Biotechnology and Bioengineering, vol. 112, No. 2, 2015, pp. 376-385, doi: 10.1002/bit.25360.
Roodveldt et al., "Directed evolution of proteins for heterologous expression and stability", Current Opinion in Structural Biology, vol. 15, No. 1, Feb. 2005, pp. 50-56, doi: 10.1016/j.sbi.2005.01.001.
Ryu et al., "Expression in yeast of secreted lignin peroxidase with improved 2,4-dichlorophenol degradability by DNA shuffling", Journal of Biotechnology, vol. 135, No. 3, Jun. 30, 2008, pp. 241-246, doi: 10.1016/j.jbiotec.2008.04.007.
Sainsbury et al., "PEAQ: versatile expression vectors for easy and quick transient expression of heterologous proteins in plants", Plant Biotechnology Journal, vol. 7, No. 7, Sep. 2009, pp. 682-693, doi: 10.1111/j.1467-7652.2009.00434.x.
Sheen, "Peroxidases in the Genus *Nicotiana*", Theoretical and Applied Genetics, vol. 40, Jan. 1970, pp. 18-25, doi: 10.1007/BF00280982.
Shusta et al., "Yeast Polypeptide Fusion Surface Display Levels Predict Thermal Stability and Soluble Secretion Efficiency", Journal of Molecular Biology, vol. 292, No. 5, Oct. 8, 1999, pp. 949-956, doi: 10.1006/jmbi.1999.3130.
Sigoillot et al., "Fungal Strategies for Lignin Degradation", Advances in Botanical Research, vol. 61, 2012, pp. 263-308, doi: 10.1016/B978-0-12-416023-1.00008-2.
Smith et al., "Multiple Molecular Forms of Peroxidases and Esterases Among *Nicotiana* Species and Amphiploids", Journal of Heredity, vol. 61, No. 5, Sep. 1970, pp. 203-212, doi: 10.1093/oxfordjournals.jhered.a108085.
Smith et al., "Substrate binding and catalysis in heme peroxidases", Current Opinion in Chemical Biology, vol. 2, No. 2, Apr. 1998, pp. 269-278, doi: 10.1016/S1367-5931(98)80069-0.
Sollewijn Gelpke et al., "Homologous Expression of Recombinant Lignin Peroxidase in Phanerochaete chrysosporium", Applied and Environmental Microbiology, vol. 65, No. 4, Apr. 1, 1999, pp. 1670-1674, doi: 10.1128/AEM.65.4.1670-1674.1999.
Tang et al., "Engineering Protein Folding and Translocation Improves Heterologous Protein Secretion in *Saccharomyces cerevisiae*", Bio-

(56) References Cited

OTHER PUBLICATIONS technology and Bioengineering, vol. 112, No. 9, Sep. 2015, pp. 1872-1882, doi: 10.1002/bit.25596.
Tang et al., "Engineering vesicle trafficking improves the extracellular activity and surface display efficiency of cellulases in *Saccharomyces cerevisiae*", Biotechnology for Biofuels, vol. 10, No. 53, Feb. 27, 2017, 13 pgs., doi: 10.1186/s13068-017-0738-8.
Tien et al., "Lignin Peroxidase of Phanerochaete chrysosporium", Methods in Enzymology, vol. 161, 1988, pp. 238-249, doi: 10.1016/0076-6879(88)61025-1.
Ulmer et al., "Rapid Degradation of Isolated Lignins by Phanerochaete chrysosporium", Applied and Environmental Microbiology, vol. 45, No. 6, Jun. 1983, pp. 1795-1801, doi: 10.1128/aem.45.6.1795-1801.1983.
Van Zyl et al., "Overexpression of native *Saccharomyces cerevisiae* ER-to-Golgi SNARE genes increased heterologous cellulase secretion", Applied Microbiology and Biotechnology, vol. 100, No. 1, Oct. 8, 2015, pp. 505-518, doi: 10.1007/s00253-015-7022-2.
Vina-Gonzalez et al., "Functional expression of aryl-alcohol oxidase in *Saccharomyces cerevisiae* and Pichia pastoris by directed evolution", Biotechnology and Bioengineering, vol. 115, No. 7, 2018, 9 pgs., doi: 10.1002/bit.26585.
Wang et al., "Exploring the potential of *Saccharomyces cerevisiae* for biopharmaceutical protein production", Current Opinion in Biotechnology, vol. 48, Dec. 2017, pp. 77-84, doi: 10.1016/j.copbio.2017.03.017.
Wariishi et al., "In Vitro Depolymerization of Lignin by Manganese Peroxidase of Phanerochaete Chrysosporium", Biochemical and Biophysical Research Communications, vol. 176, No. 1, Apr. 15, 1991, pp. 269-275, doi: 10.1016/0006-291X(91)90919-X.
Wariishi et al., "Lignin Peroxidase Compound III. Mechanism of Formation and Decomposition", The Journal of Biological Chemistry, vol. 265, No. 4, Feb. 5, 1990, pp. 2070-2077, doi: 10.1016/S0021-9258(19)39941-7.
Wariishi et al., "Manganese(II) Oxidation by Manganese Peroxidase from the Basidiomycete Phanerochaete chrysosporium. Kinetic Mechanism and Role of Chelators", The Journal of Biological Chemistry, vol. 267, No. 33, Nov. 25, 1992, pp. 23688-23695, doi: 10.1016/S0021-9258(18)35893-9.
Wen et al., "A R2R3-MYB Gene LfMYB113 is Responsible for Autumn Leaf Coloration in Formosan sweet gum (*Liquidambar formosana* Hance)", Plant and Cell Physiology, vol. 58. No. 3, 2017, pp. 508-521, doi: 10.1093/pcp/pcw228.
Wentz et al., "A Novel High-Throughput Screen Reveals Yeast Genes That Increase Secretion of Heterologous Proteins", Applied Environmental Microbiology, vol. 73, No. 4, Feb. 2007, pp. 1189-1198, doi: 10.1128/AEM.02427-06.
Wittrup, "Protein engineering by cell-surface display", Current Opinion in Biotechnology, vol. 12, No. 4, Aug. 2001, pp. 395-399, doi: 10.1016/s0958-1669(00)00233-0.
Wittrup et al., "Existence of an Optimum Expression Level for Secretion of Foreign Proteins in Yeast", Annals of the New York Academy of Science, Nov. 1994, vol. 745, No. 1, Nov. 1994, pp. 321-330, doi: 10.1111/j.1749-6632.1994.tb44385.x.
Zollner et al., "Molecular cloning and characterization of the *Saccharomyces cerevisiae* CYT2 gene encoding cytochrome-cl-heme lyase", European Journal of Biochemistry, vol. 207, No. 3, Aug. 1992, pp. 1093-1100, doi: 10.1111/j.1432-1033.1992.tb17146.x.

* cited by examiner

METHODS AND SYSTEMS TO SECRETE LIGNIN-MODIFYING ENZYMES AND USES THEREOF

CROSS-REFERENCE TO RELATED APPLICATIONS

This application is a national stage of PCT Patent Application No. PCT/US2021/036248, entitled "Methods and Systems to Secrete Lignin-Modifying Enzymes and Uses Thereof" to Khlystov, filed Jun. 7, 2021, which claims priority to U.S. Provisional Application Ser. No. 63/035,172, entitled "Methods and Systems to Secrete Lignin-Modifying Enzymes and Uses Thereof" to Khlystov, filed Jun. 5, 2020, which is incorporated herein by reference in its entirety.

STATEMENT REGARDING FEDERALLY SPONSORED RESEARCH OR DEVELOPMENT

This invention was made with Governmental support under Grant No. DE-SC0014112 awarded by the U.S. Department of Energy. The government has certain rights in the invention.

SEQUENCE LISTING

This application hereby incorporates by reference the material of the electronic Sequence Listing filed concurrently herewith. The material in the electronic Sequence Listing is submitted as a text (.txt) file entitled "06788_SeqList_ST25.txt" created on May 26, 202, which has a file size of 138,423 bytes and is herein incorporated by reference in its entirety.

FIELD OF THE INVENTION

The present invention is directed to lignin-modifying enzyme secretion, including methods of synthesis and applications thereof. More particularly, embodiments are directed to organisms designed to secrete lignin-modifying enzymes.

BACKGROUND OF THE INVENTION

Lignocellulose is the most abundant raw material on Earth, consisting of primarily two components: carbohydrate polymers collectively termed as cellulose and hemicellulose; and the random heterogeneous polymer that encapsulates them from pathogenic attack, lignin. Together, lignin and cellulose represent an attractive renewable source for commodity chemicals and fuels. Extensive efforts are underway to achieve lignin deconstruction through inorganic catalytic means; these processes however rely on aggressive chemical treatment and remain difficult to tune and engineer for the capture of valuable intermediate breakdown products. While the conversion of cellulosic biomass has been readily achieved in the industry, scalable and tunable valorization of lignin remains elusive.

SUMMARY OF THE INVENTION

Systems and methods to produce lignin-modifying enzymes in accordance with embodiments of the invention are disclosed. In one embodiment, a vehicle for gene expression includes an organism capable of expressing a gene transformed with an expression vector containing a lignin-modifying enzyme.

In one embodiment, a transgenic organism includes a mutant of a native gene and an expression cassette encoding for a lignin-modifying enzyme.

In a further embodiment, the native gene is selected from cyt2, pmt2, vps30, vps38, vta1, and pom152.

In another embodiment, the native gene is cyt2 or pmt2.

In a still further embodiment, the transgenic organism further includes a deletion of a second native gene.

In still another embodiment, the native gene is cyt2 and the second native gene is pmt2.

In a yet further embodiment, the lignin-modifying enzyme is a heme peroxidase.

In yet another embodiment, the lignin-modifying enzyme is encoded by one of SEQ ID NOs: 1-78.

In a further embodiment again, the expression cassette further encodes for a scaffold protein and a surface display protein, where the surface display protein is linked to the lignin-modifying enzyme, such that a hybrid peptide is produced with the lignin-modifying enzyme and the surface display protein.

In another embodiment again, the scaffold protein is AGA1 and the surface display protein is AGA2.

In a further additional embodiment, the scaffold protein is encoded by SEQ ID NO: 80 and the surface display protein is encoded by SEQ ID NO: 81.

In another additional embodiment, the expression cassette further encodes for an inducible promoter operatively linked to the lignin-modifying enzyme.

In a still yet further embodiment, wherein the inducible promoter is a Gal10-Gal1 promoter.

In still yet another embodiment, the inducible promoter is encoded by SEQ ID NO: 79.

In a still further embodiment again, an expression cassette includes DNA encoding a gene of interest encoding a functional peptide of interest, a promoter operatively linked to the gene of interest, a scaffold protein, and a surface display protein operatively linked to the gene of interest, such that a hybrid peptide is produced linking the functional peptide of interest and the surface display protein.

In still another embodiment again, the functional peptide of interest is a heme peroxidase.

In a still further additional embodiment, the functional peptide of interest is encoded by one of SEQ ID NOs: 1-78.

In still another additional embodiment, the scaffold protein is AGA1 and the surface display protein is AGA2.

In a yet further embodiment again, the scaffold protein is encoded by SEQ ID NO: 80 and the surface display protein is encoded by SEQ ID NO: 81.

In yet another embodiment again, the promoter is an inducible promoter.

In a yet further additional embodiment, the promoter is a Gal10-Gal1 promoter.

In yet another additional embodiment, the promoter is encoded by SEQ ID NO: 79.

In a further additional embodiment again, a method for screening surface display of a protein includes transforming a library of mutant cells with an expression cassette encoding a functional peptide of interest, where the library contains a collection of cells deficient in one or more native genes, identifying a cell from the library that surface displays the functional peptide of interest, and identifying a mutant in the cell from the library of mutants that surface displays the functional peptide of interest.

In another additional embodiment again, the method further includes identifying a cell from the library that possesses activity of the functional peptide of interest.

In a still yet further embodiment again, identifying the activity of the functional peptide of interest includes providing a reactant to the transformed library and detecting the reactant.

In still yet another embodiment again, the reactant is biotinyl tyramide and hydrogen peroxide.

In a still yet further additional embodiment, the biotinyl tyramide and hydrogen peroxide are provided at a concentration of 100 μM.

In still yet another additional embodiment, the library has a cell density of 106 cells per mL.

In a yet further additional embodiment again, identifying surface display of the functional peptide of interest includes providing a fluorophore conjugated antibody specific to the functional peptide of interest to the transformed library and detecting the fluorophore.

In yet another additional embodiment again, providing a fluorophore conjugated antibody specific to the functional peptide of interest to the transformed library is performed at 4° C. for 1.75 hours.

In a still yet further additional embodiment again, identifying the mutant includes sequencing the genome of the cell that surface displays the functional peptide of interest.

In still yet another additional embodiment again, the functional peptide of interest is a heme peroxidase.

In another further embodiment, the functional peptide of interest is encoded by one of SEQ ID NOs: 1-78.

In still another further embodiment, the expression cassette further encodes for a scaffold protein and a surface display protein, where the surface display protein is linked to the functional peptide of interest, such that a hybrid peptide is produced with the functional peptide of interest and the surface display protein.

In yet another further embodiment, the scaffold protein is AGA1 and the surface display protein is AGA2.

In another further embodiment again, the scaffold protein is encoded by SEQ ID NO: 80 and the surface display protein is encoded by SEQ ID NO: 81.

Another further additional embodiment, the expression cassette further encodes for an inducible promoter operatively linked to the functional peptide of interest.

Yet another further additional embodiment, the inducible promoter is a Gal10-Gal1 promoter.

Again another further additional embodiment, the inducible promoter is encoded by SEQ ID NO: 79.

BRIEF DESCRIPTION OF THE DRAWINGS

These and other features and advantages of the present invention will be better understood by reference to the following detailed description when considered in conjunction with the accompanying drawings where.

DETAILED DISCLOSURE OF THE INVENTION

Figures 1A, 1B:
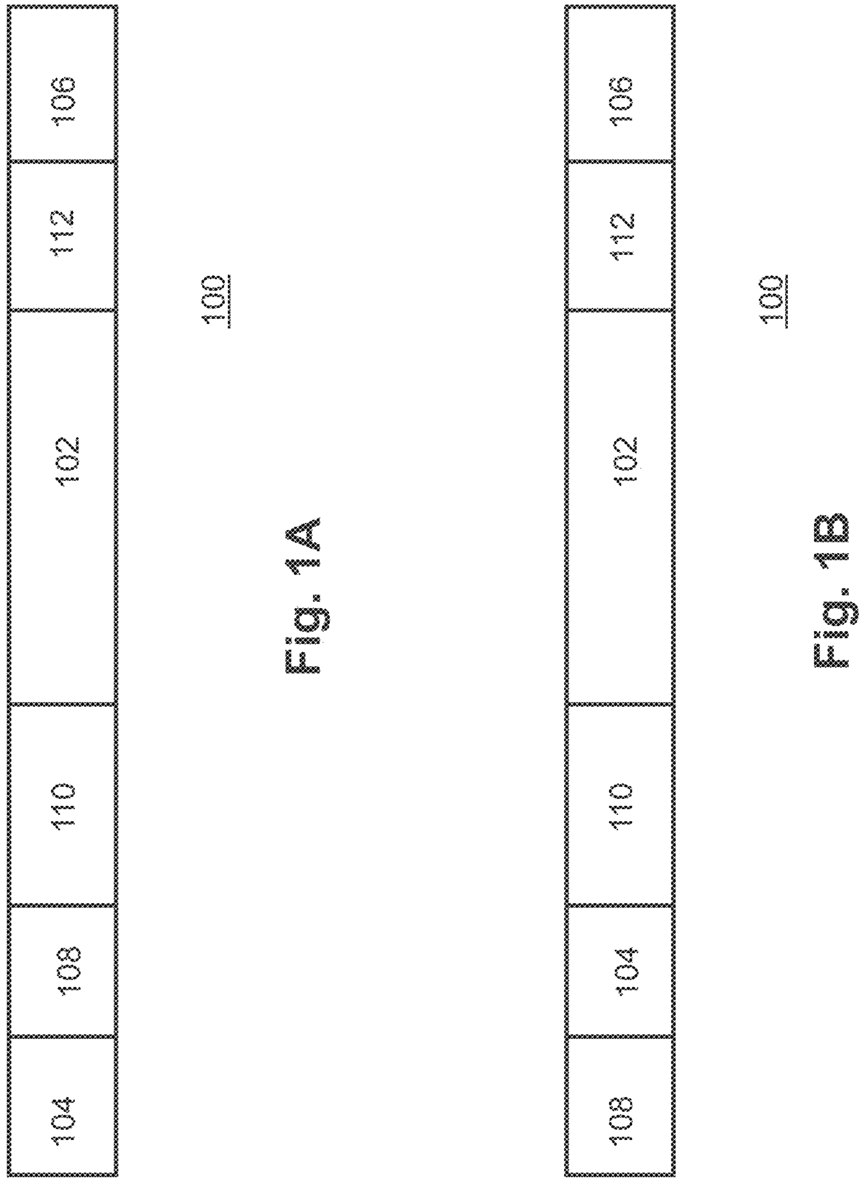
FIGS. 1A-1B illustrate gene expression constructs in accordance with various embodiments.

Nature has evolved a biological path to lignin valorization through bacteria and especially basidiomycete fungi. Several bacterial species have been shown to be capable lignin metabolizers but are dwarfed by the lignin degradation rates of fungi. (See Ahmad et al., Development of novel assays for lignin degradation: comparative analysis of bacterial and fungal lignin degraders, Mol. BioSyst., 2010, 6, 815-821; the disclosure of which is incorporated herein by reference in its entirety.) Thanks to recent major advances in genetics and bioinformatics, previous studies have elucidated the genomic origins of fungal lignin mineralization. (See Riley et al., Comparative genomics of biotechnologically important yeasts, Proc. Nat'l Acad. Sci. August 2016, 113 (35) 9882-9887; the disclosure of which is incorporated herein by reference in its entirety.) Several key enzyme families have been identified, and their lignin-degrading activity has been demonstrated through in vitro experiments. (See Hammel et al., Ligninolysis by a Purified Lignin Peroxidase, J. Biol. Chem., June 1993, 268 (17), 12274-81; and Warishii et al., In vitro depolymerization of lignin by manganese peroxidase of *Phanerochaete chrysosporium*, Biochem Biophys Rsch Comms, 1991 176(1) 269-75; the disclosures of which are incorporated herein by reference in their entireties.)

By far the greatest roadblock to accelerating the study of biological lignin degradation is the production of fungal lignin-modifying enzymes, particularly heme peroxidases. Previous research has relied primarily on enzymes purified from the native basidiomycete host or refolded from recombinant *E. coli*. Limited progress has been achieved in genetic engineering of basidiomycetes to homologously over-express lignin-degrading enzymes, but these hosts remain largely genetically intractable and more difficult to cultivate relative to microbial platforms. (See Lopez et al., Homologous and Heterologous Expression of Basidiomycete Genes Related to Plant Biomass Degradation, Homologous and Heterologous Expression of Basidiomycete Genes Related to Plant Biomass Degradation. In: Schmoll M., Dattenböck C. (eds) Gene Expression Systems in Fungi: Advancements and Applications. Fungal Biology. Springer, 2012; and Gelpke, et al., Homologous Expression of Recombinant Lignin Peroxidase in *Phanerochaete chrysosporium*, Applied and Enviro Microbio., 1999, 65(4), 1670-74; the disclosures of which are incorporated herein by reference in their entireties.) Moreover, any expression strategy in basidiomycete hosts suffers from the background of natively-produced lignin-degrading enzymes, requiring extensive purification to study individual members of the enzymatic milieu. (See Lambertz et al., Progress and obstacles in the production and application of recombinant lignin-degrading peroxidases, Bioengineered 2016 7(3); the disclosure of which is incorporated herein by reference in its entirety.) Their study by traditional methods such as reverse genetics also remains inaccessible due to the lack of genetic tools for basidiomycetes. Lignin-modifying enzymes produced from *E. coli* commonly suffer misfolding problems and must be refolded in vitro, an inherently lengthy and inefficient process with yields of at most 28%.

Heterologous production of proteins remains a significant bottleneck in biotechnology despite decades of research. Heterologous secretion is particularly important for the production of biotechnologically and medically relevant proteins such as enzymes and antibodies, representing multi-billion-dollar industries. Factors governing successful secretion of foreign proteins are however still poorly understood despite existing significant knowledge about the secretory pathway of common eukaryotic heterologous hosts. Engineering efficient secretion in these hosts is a long-sought goal with potentially far-reaching implications from pharmaceutical development to biomass valorization. (See e.g., Wang, G., et al. Exploring the potential of *Saccharomyces cerevisiae* for biopharmaceutical protein production. Current Opinion in Biotechnology (2017). doi:10.1016/j.copbio.2017.03.017; Delic, M., et al. Engineering of protein folding and secretion—Strategies to overcome bottlenecks for efficient production of recombinant proteins. Antioxidants and Redox Signaling (2014). doi:10.1089/ars.2014.5844; and Hou, J., et al. Metabolic engineering of recombinant protein secretion by *Saccharomyces cerevisiae*. FEMS Yeast Research (2012). doi:10.1111/j.1567-1364.2012.00810.x; the disclosures of which are hereby incorporated by reference herein in their entireties.) A common approach of improving heterologous secretion involves directed evolution campaigns aimed at identifying protein sequence variants that enable greater levels of production. (See e.g., Roodveldt, C., et al. Directed evolution of proteins for heterologous expression and stability. Current Opinion in Structural Biology (2005). doi:10.1016/j.sbi.2005.01.001; the disclosure of which is hereby incorporated by reference herein in its entirety.) However, secretion is marred by a strong dependence on the screening method involved, often resulting in unintentional and sometimes undesirable alteration to molecular properties of the protein target. This holds especially true for enzymes, where evolution directed at a particular screening substrate is reflected in changes in enzyme kinetic properties and substrate affinities. Other approaches have relied on tailoring genetic components to minimize metabolic impact and cellular toxicity resulting from the production and secretion of a foreign protein. Balancing protein overexpression with the limits of the host's native secretory capacity is typically achieved through judicious selection of promoters and expression cassettes along with well-tolerated endoplasmic reticulum (ER) signal peptides. (See e.g., Wittrup, K. et al. Existence of an Optimum Expression Level for Secretion of Foreign Proteins in Yeasta. Ann. N. Y. Acad. Sci. (2006). doi:10.1111/j.1749-6632.1994.tb44385.x; and Rakestraw, J. A., et al. Directed evolution of a secretory leader for the improved expression of heterologous proteins and full-length antibodies in *Saccharomyces cerevisiae*. Biotechnol. Bioeng. (2009). doi:10.1002/bit.22338; the disclosures of which are hereby incorporated by reference herein in their entireties.)

Modification of the protein sequence to accomplish efficient secretion requires individual development of variants for each protein of interest, an inherently time-consuming process. Optimization of the genetic over-expression platform is likewise a constrained approach limited by the native capacity of the host's secretory pathway. Developing a super-secreting heterologous host would circumvent both of these long-standing issues. With the abundance of genetic tools and wealth of knowledge available, *Saccharomyces cerevisiae* presents an attractive candidate for a proof-of-concept super-secreting platform. The secretory pathway of this yeast has been extensively characterized and the secretion of numerous foreign proteins has been studied in this host. (See e.g., Idiris, A., et al. Engineering of protein secretion in yeast: Strategies and impact on protein production. Applied Microbiology and Biotechnology (2010). doi:10.1007/s00253-010-2447-0; the disclosure of which is hereby incorporated by reference herein in its entirety.) Functional genomic screens as well as targeted gene editing approaches have been successfully employed in engineering improved secretion of heterologous proteins. Gene deletion and cDNA overexpression libraries have revealed that modulating expression of native secretory components can result in enhanced secretion. (See e.g., Wentz, A. E. & Shusta, E. V. A novel high-throughput screen reveals yeast genes that increase secretion of heterologous proteins. Appl. Environ. Microbiol. (2007). doi:10.1128/AEM.02427-06; Hoshida, H., et al. N-glycosylation deficiency enhanced heterologous production of a *Bacillus licheniformis* thermostable α-amylase in *Saccharomyces cerevisiae*. Appl. Microbiol. Biotechnol. (2013). doi:10.1007/s00253-012-4582-2; Rodriguez-Limas, W. A., et al. Blocking endocytotic mechanisms to improve heterologous protein titers in *Saccharomyces cerevisiae*. Biotechnol. Bioeng. (2015). doi:10.1002/bit.25360; Van Zyl, J. H. D., et al. Overexpression of native *Saccharomyces cerevisiae* ER-to-Golgi SNARE genes increased heterologous cellulase secretion. Appl. Microbiol. Biotechnol. (2016). doi:10.1007/s00253-015-7022-2; Tang, H. et al. Engineering protein folding and translocation improves heterologous protein secretion in *Saccharomyces cerevisiae*. Biotechnol. Bioeng. (2015). doi:10.1002/bit.25596; Tang, H. et al. Engineering vesicle trafficking improves the extracellular activity and surface display efficiency of cellulases in *Saccharomyces cerevisiae*. Biotechnol. Biofuels (2017). doi:10.1186/s13068-017-0738-8; de Ruijter, J. C., et al. Enhancing antibody folding and secretion by tailoring the *Saccharomyces cerevisiae* endoplasmic reticulum. Microb. Cell Fact. (2016). doi:10.1186/s12934-016-0488-5; and Wang, T. Y. et al. Systematic screening of glycosylation- and trafficking-associated gene knockouts in *Saccharomyces cerevisiae* identifies mutants with improved heterologous exocellulase activity and host secretion. BMC Biotechnol. (2013). doi:10.1186/1472-6750-13-71; the disclosures of which are hereby incorporated by reference herein in their entireties.) Reverse metabolic engineering screens have demonstrated that whole-cell random mutagenesis by UV is another powerful approach in developing strain backgrounds with improved secretion. (See e.g., Huang, M. et al. Microfluidic screening and whole-genome sequencing identifies mutations associated with improved protein secretion by yeast. Proc. Natl. Acad. Sci. U.S.A. (2015). doi:10.1073/pnas.1506460112; and Liu, Z. et al. Improved production of a heterologous amylase in *Saccharomyces cerevisiae* by inverse metabolic engineering. Appl. Environ. Microbiol. (2014). doi:10.1128/AEM.00712-14; the disclosures of which are hereby incorporated by reference herein in their entireties.) Biotechnologically relevant foreign proteins such as antibodies, T-cell receptors, cellulases, and amylases have all been shown to have improved secretion in the context of these engineered strains. However, these strategies suffer from low-throughput screening methods and expensive whole-genome sequencing to identify strain modifications resulting in secretion enhancement.

Turning now to the diagrams and figures, embodiments of the invention are generally directed to lignin-modifying enzymes and systems and methods of their production and/or synthesis. In many embodiments, yeast strains, including *S. cerevisiae*, are used to produce and secrete lignin-modifying enzymes Further embodiments are directed to methods to screening peroxidase-producing yeast strains, including *S. cerevisiae*. In various embodiments, secreting is includes surface-display, such that a protein or enzyme being produced is placed on an outer surface of a cell.

Yeast Strains for Secreting Proteins

Turning to FIGS. 1A-1B, many embodiments are directed to methods and systems to express and secrete one or more proteins of interest. FIG. 1 illustrates an expression cassette 100 in accordance with many embodiments. In many embodiments, expression cassette 100 comprises a gene of interest 102. In various embodiments, the gene of interest 102 encodes for a functional peptide of interest, such as a protein or enzyme. In certain embodiments, the functional peptide of interest is a full-length protein or enzyme, while in several embodiments the functional peptide of interest is a truncated and/or modified peptide or protein that retains the functionality (e.g., full, increased, decreased functionality) of a full-length protein, enzyme, or other peptide. In some embodiments, the gene of interest 102 encodes for a heme peroxidase. In certain embodiments, the heme peroxidase is encoded by a DNA sequence selected from SEQ ID NOs: 1-78.

Additional embodiments are directed to transcript expression modifiers that are operatively linked to a gene of interest, including, 5' elements 104 and/or 3' elements 106, such as promoters, enhancers, terminators, etc., that assist with gene transcription and/or translation. Many types of promoters, enhancers, and terminators are known in the art, including constitutive and inducible promoters. Various embodiments include a constitutive promoter, such as cauliflower mosaic virus 35S (CaMV 35S) or cauliflower mosaic virus 19S (CaMV 19S). Certain embodiments include a galactose inducible promoter. In some embodiments, the galactose inducible promoter is a Gal10/Gal1 promoter. In certain embodiment, the Gal10/Gal1 promoter is selected from SEQ ID NO: 79. Various other embodiments use a copper inducible promoter, such as CUP1, and/or an ethanol inducible promoter, such as ADH2. Some embodiments include multiple expression modifiers, 5' elements 104 and/or multiple 3' elements 106 to further enhance gene transcription.

Additional embodiments include one or more scaffold proteins 108 and/or one or more proteins allowing for surface display (also referred to as a surface display protein) 110. In certain embodiments, the scaffold protein 108 is selected from AGA1 (SEQ ID NO: 80) and/or the protein allowing for surface display 110 is selected from AGA2 (SEQ ID NO: 81). In various embodiments, the position of one or more scaffold proteins 108 and/or one or more proteins allowing for surface display 110 are varied within cassette 100 to optimize expression and/or secretion of gene of interest 102. For example, some embodiments place one or more scaffold proteins 108 5' to a 5' element 110, such as illustrated in FIG. 1B. In such embodiments, the surface display protein 110 is linked to the gene of interest, such that the resultant protein is a linked peptide of a surface display protein and the protein of interest. Various embodiments maintain the expression vector as part of a plasmid or extrachromosomal/extragenomic DNA for expression, while further embodiments include sequences or other components to integrate the expression vector into genomic or chromosomal DNA of the organism.

Further embodiments include one or more tags 112, labels, or other peptides that can be used to identify a protein of interest. For example, some cassettes include a His tag, a Myc tag, or other peptide tag that allows for identification of a protein of interest.

Various embodiments include a cell transfected with an expression cassette, such as expression cassette 100. In various embodiments, the cell is a plant cell, mammalian cell, fungal cell, bacterial cell, archaeal cell, etc. In some embodiments, a yeast cell is used to express and secrete the protein of interest. Various embodiments utilize cells from the *Saccharomyces* genus (e.g., *S. cerevisiae, S. pombe*, etc.) as well as the *Pichia* (*Komagataella*) genus (e.g., *P. pastoris*, etc.). Yeast strains, in accordance with many embodiments, are from *S. cerevisiae*. In typical expression systems, AGA1 must incorporated into genomic DNA of yeast, while AGA2 is included in an expression cassette. By including both AGA1 and AGA2 into an expression cassette, many embodiments allow for functional surface display of a protein of interest independent of a yeast cell's genetic background.

Various embodiments transfect a cell that contains one or more genetic knockouts, deletions, or mutations in yeast genomic DNA. FIGS. 2A-2B illustrate exemplary data of yeast strains containing a knockout for various genes (X-axis labels) that have been transfected with an expression construct containing PE-vp12 (SEQ ID NO: 22) (FIG. 2A) or AR-hrp (SEQ ID NO: 78) (FIG. 2B). FIGS. 2A-2B illustrate that certain knockout strains have higher enzymatic activity from the PE-vp12 and AR-hrp transgenes over a silent deletion strain (Δho), which is generally accepted as a wildtype control, indicating that cells deficient in certain genes (e.g., cyt2, pmt2, etc.) allow for greater enzymatic activity of certain transgenes. As such, various embodiments transfect a cell that contains one or more genetic knockouts, deletions, or mutations in yeast genomic DNA. Additionally, FIGS. 3A-3B illustrate exemplary data of growth measurements of various exemplary embodiments exhibiting increased surface display of PE-vp12 (SEQ ID NO: 22) (FIG. 3A) and AR-hrp (SEQ ID NO: 78) (FIG. 3B), as normalized to Δho. As such, various embodiments include yeast with a knockout and/or deletion in one or more of YBP2, CYM1, CYT2, MBB1, QDR2, VPS30, VPS38, BTA1, POM152, SCS2, SSH1, and PMT2.

Figure 4:
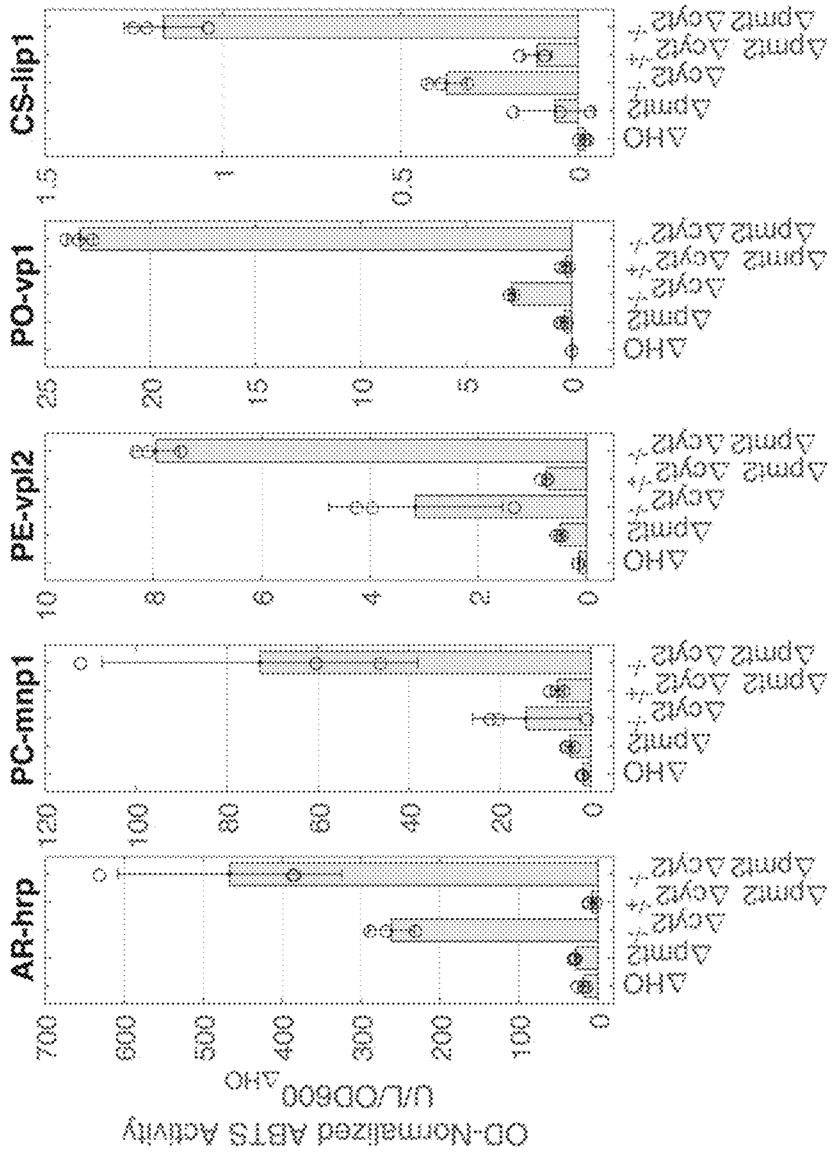
FIG. 4 illustrates epistatic effects in transgenic yeast in accordance with various embodiments.

Additionally, many embodiments include knockouts and/or deletions in one or more genes. Turning to FIG. 4, exemplary data showing deletions in two genes (e.g., Δcyt2 and Δpmt2). Specifically, FIG. 4 illustrates the activity of AR-hrp (SEQ ID NO: 78) PC-mnp1 (SEQ ID NO: 11), PE-vp12 (SEQ ID NO: 22), PO-vp1 (SEQ ID NO: 45), and CS-lip1 (SEQ ID NO: 33) expressed in various mutant backgrounds are illustrated. In particular, the mutant backgrounds include a Δho control, Δpmt2, Δcyt2, and Δpmt2Δcyt2$^{-/+}$ (e.g., heterozygous for Δcyt2), and Δpmt2Δcyt2$^{-/-}$ (e.g., homozygous for Δcyt2), indicating that many embodiments of double deletion strains further increase activity and secreted protein levels of lignin-modifying enzymes.

Figure 2:
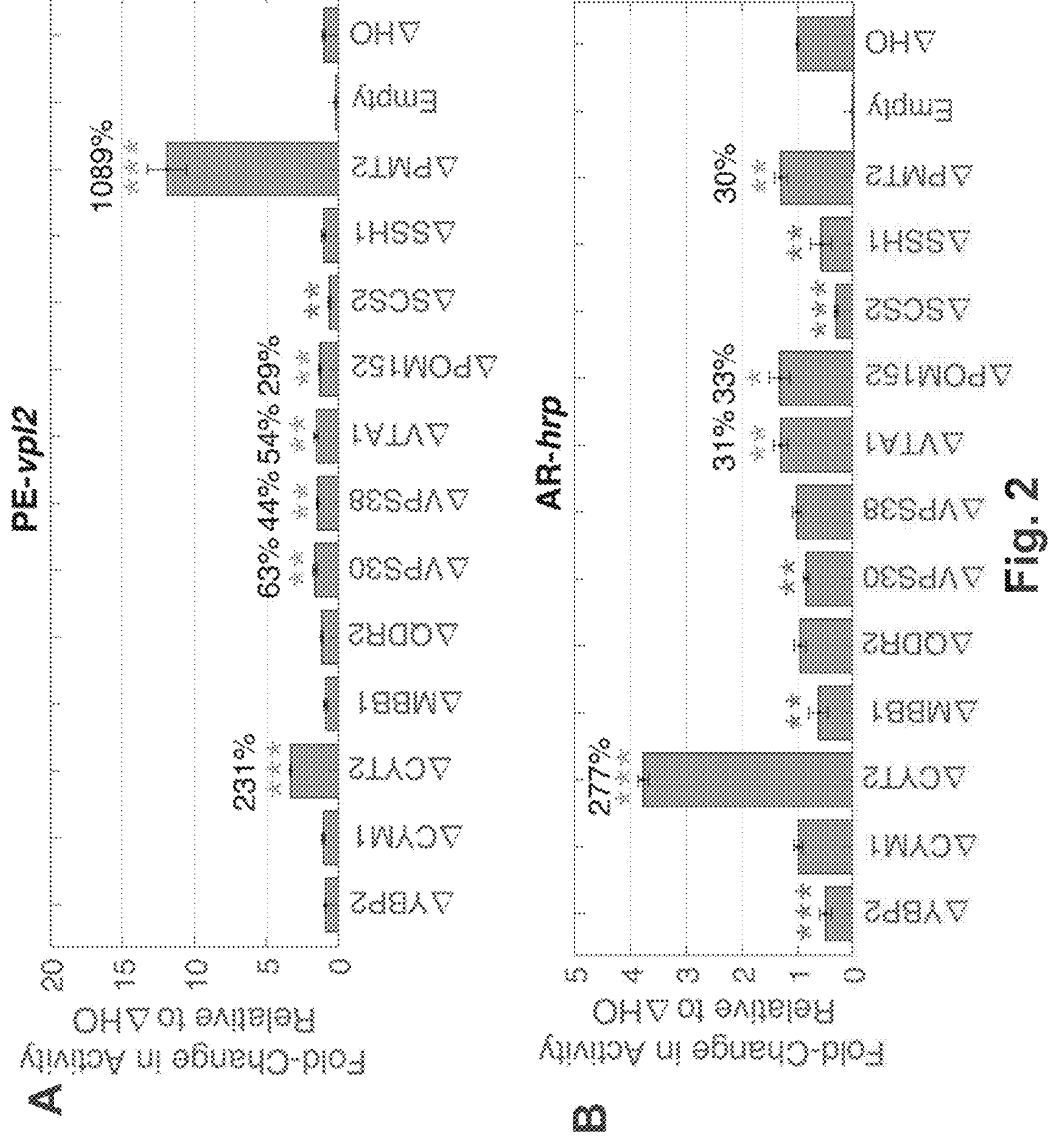
FIGS. 2A-2B illustrate enzyme activity levels of transgenic yeast in accordance with various embodiments.
Figure 3:
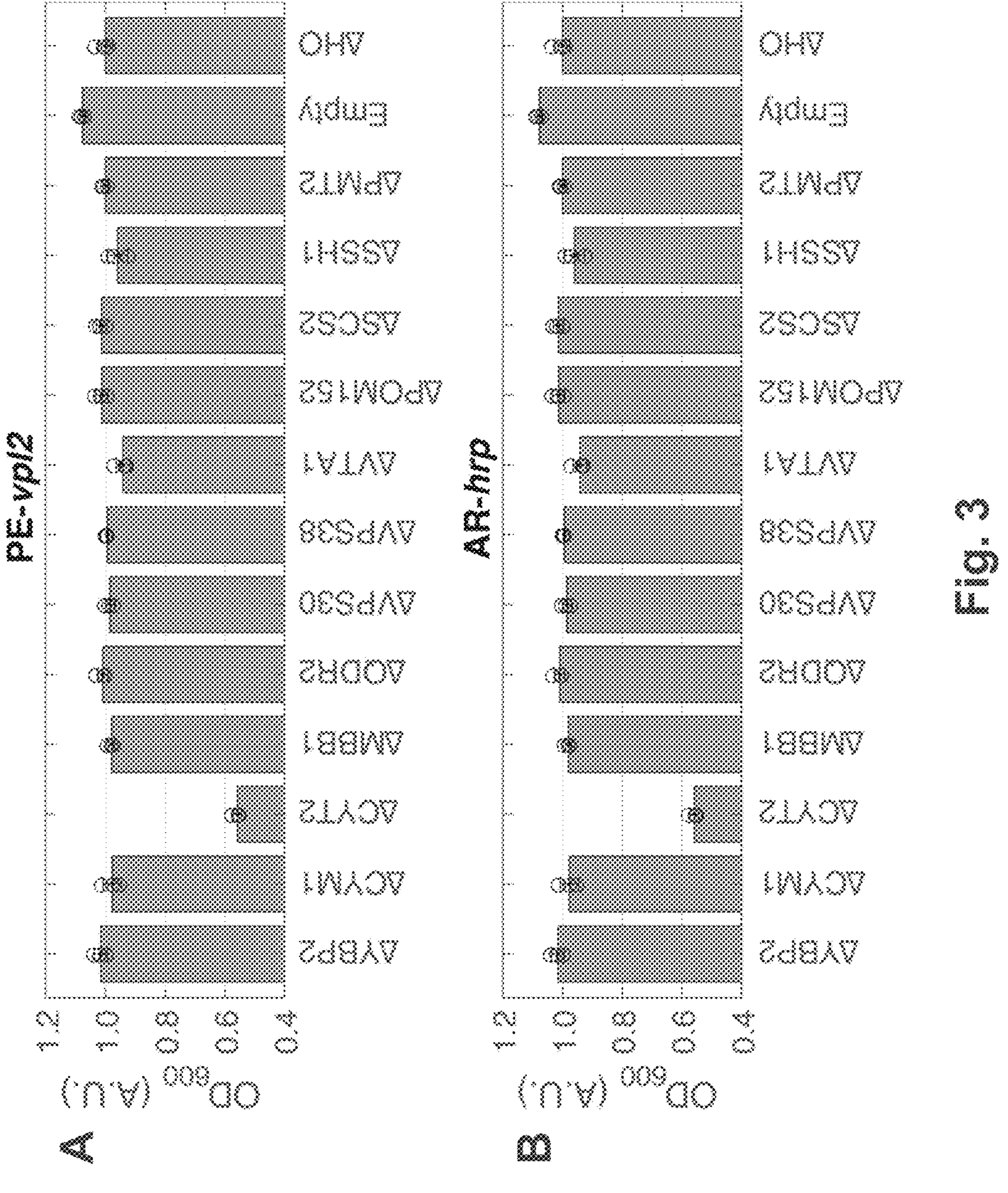
FIG. 3A-3B illustrate growth measurements of transgenic yeast in accordance with various embodiments.

It should be noted that the FIGS. 2-4 illustrate exemplary data of enzyme activity as a proxy for enzyme secretion or surface display, where a linear relationship can be assumed between enzyme level and activity level. However, certain embodiments obtain measurements of secreted and/or surface-displayed enzyme or protein level via another method or mechanism to show that various embodiments secrete and/or display more protein rather than increase activity level or efficacy of a target protein.

Methods to Screen Enzyme Secretion

Figure 5A:
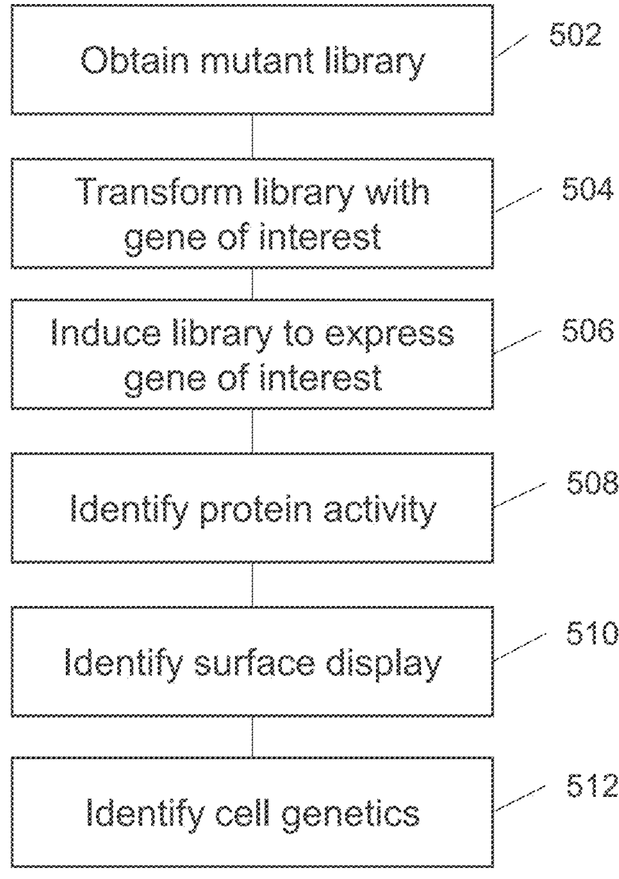
FIG. 5A illustrates a flow chart of a method to screen for protein expression in accordance with various embodiments.

Turning to FIG. 5A, an exemplary method 500 to screen a library of yeast strains for production and secretion of lignin-modifying enzymes is illustrated in accordance with many embodiments. In various embodiments, a library of mutants is obtained at 502. The library can be of various organisms suitable for protein expression and/or production. In many embodiments, the organism is a fungus, such as a yeast. Various embodiments use *S. cerevisiae*. In many embodiments, the library is a mutant and/or deletion collection, where individual colonies, cells, or organisms are deficient for one or more genes and/or contain a mutant in one or more genes, such as described in FIGS. 2-4 and associated text.

At 504, many embodiments transform or transfect the library with a gene of interest. In certain embodiments, the gene is a protein, while in additional embodiments the protein is an enzyme. In further embodiments the enzyme is a heme peroxidase. In various embodiments, the gene of interest is contained within an expression cassette, such as describe in FIGS. 1A-1B and associated text. Various methods exist in the art for transforming/transfecting an organism, including electroporation, biolistics, viral-mediated transformation, bacterial-mediated transformation (e.g., *Agrobacterium* transformation), heat shock, monovalent cation transformation (e.g., lithium acetate transformation), and/or any other suitable method for introducing an expression cassette and/or gene of interest into an organism. In certain embodiments, a lithium acetate method is used to transform the library, which are plated on synthetic defined media plates lacking leucine to select for transformants. In various embodiments, the transformants are pooled for further analysis.

Numerous embodiments induce the library to express the gene of interest at 506. In some embodiments, no action may be necessary, if a gene of interest is under a constitutive promoter. However, if a gene of interest is under an inducible promoter, an introduction of a compound, chemical, and/or other stimulus, such as galactose, can induce expression of a gene under control of an inducible promoter. Such inducers can be introduced as a buffer or medium containing the inducer. Many inducible promoters are known in the art, and one of skill in the art will understand to choose the appropriate inducer for the appropriate promoter.

Further embodiments identify protein activity or function at 508. In various embodiments, assays for protein function or activity are highly specific to the specific protein of interest. In various embodiments, identifying protein activity includes providing a reactant to the transformed library. For embodiments expressing heme peroxidases, the reactant includes a label that can be identified via an antibody (e.g., biotin). In certain embodiments biotinyl tyramide is used. In such embodiments, tyramide reacts with a peroxidase, which allows the tyramide to bind to a cell surface (e.g., cell membrane and/or cell wall). The biotin moiety allows for streptavidin labelling, antibody labelling, click chemistry or other assay to identify cells or colonies that have enzymatic function. Numerous methods are known in the art to identify tagged moieties, including chromatography (e.g., pulldown assays), fluorescent tagging, growth assays, among others. Fluorescence assays can include plate readers, fluorometry, fluorescence assisted cell sorting, and any other known method.

Additional embodiments identify surface display of a protein of interest at 510. In some embodiments, identification can include using an antibody specific for the protein of interest, an epitope of the protein of interest, and/or a tag attached to the protein of interest (e.g., His and/or Myc). Numerous methods are known in the art to identify proteins, including chromatography (e.g., pulldown assays), fluorescent tagging, growth assays, among others. Fluorescence assays can include plate readers, fluorometry, fluorescence assisted cell sorting, and any other known method.

In numerous embodiments, detection assays, such as fluorescence assays, can be multiplexed using different fluorophores for each moiety (e.g., streptavidin-phycoerythin (PE) conjugate for biotinylated molecules, AF647 conjugated anti-Myc antibody). With different colors, a detector, such as a flow cytometer or plate reader can obtain multiple measurements from a cell to identify and/or differentiate cells that secrete/display protein and which cells have functional enzyme. Further embodiments also allow for quantification of secretion, expression, and/or activity/function based on the level of fluorescence.

At 512, many embodiments identify the genetics of the cells that display the gene of interest and/or have gene activity. Such embodiments include any method to identify the underlying genetics, such as sequencing, genotyping, microarray, and/or any other method for screening the cells for the underlying genetic issues, such as which gene is deleted, knocked out, or mutated.

Figure 5B:
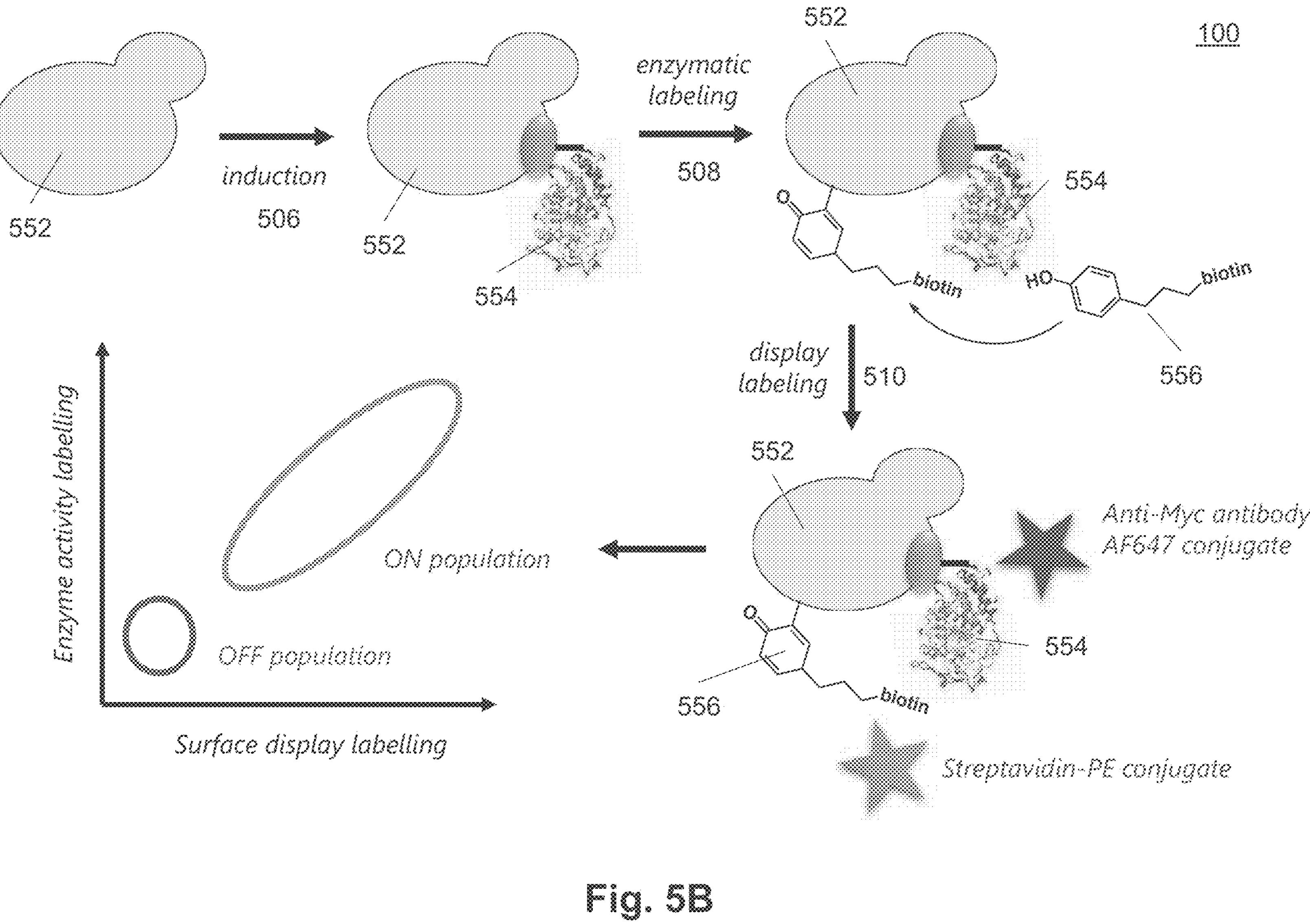
FIG. 5B illustrates a graphical illustration of an exemplary screening method in accordance with various embodiments.

Turning to FIG. 5B, an exemplary schematic of method 500 is illustrated for display of a heme peroxidase. For example, transformed yeast 552 are induced (506) to display a heme peroxidase 554 on the surface of the yeast 552. Enzyme activity is identified (508) by introduction of biotinyl tyramide 556, which reacts with a peroxidase and binds to a cell surface. Identification of the surface display (510) of the peroxidase 554 and biotinyl tyramide 556 are labeled with fluorescently conjugated molecules (anti-Myc antibody and streptavidin, respectively). With differential labelling to identify surface displaying cells and cells that have enzyme activity, it is possible to identify cells that are "on" (e.g., displaying and active) versus cells that are "off" (e.g., not displaying and/or not active).

Figure 6:
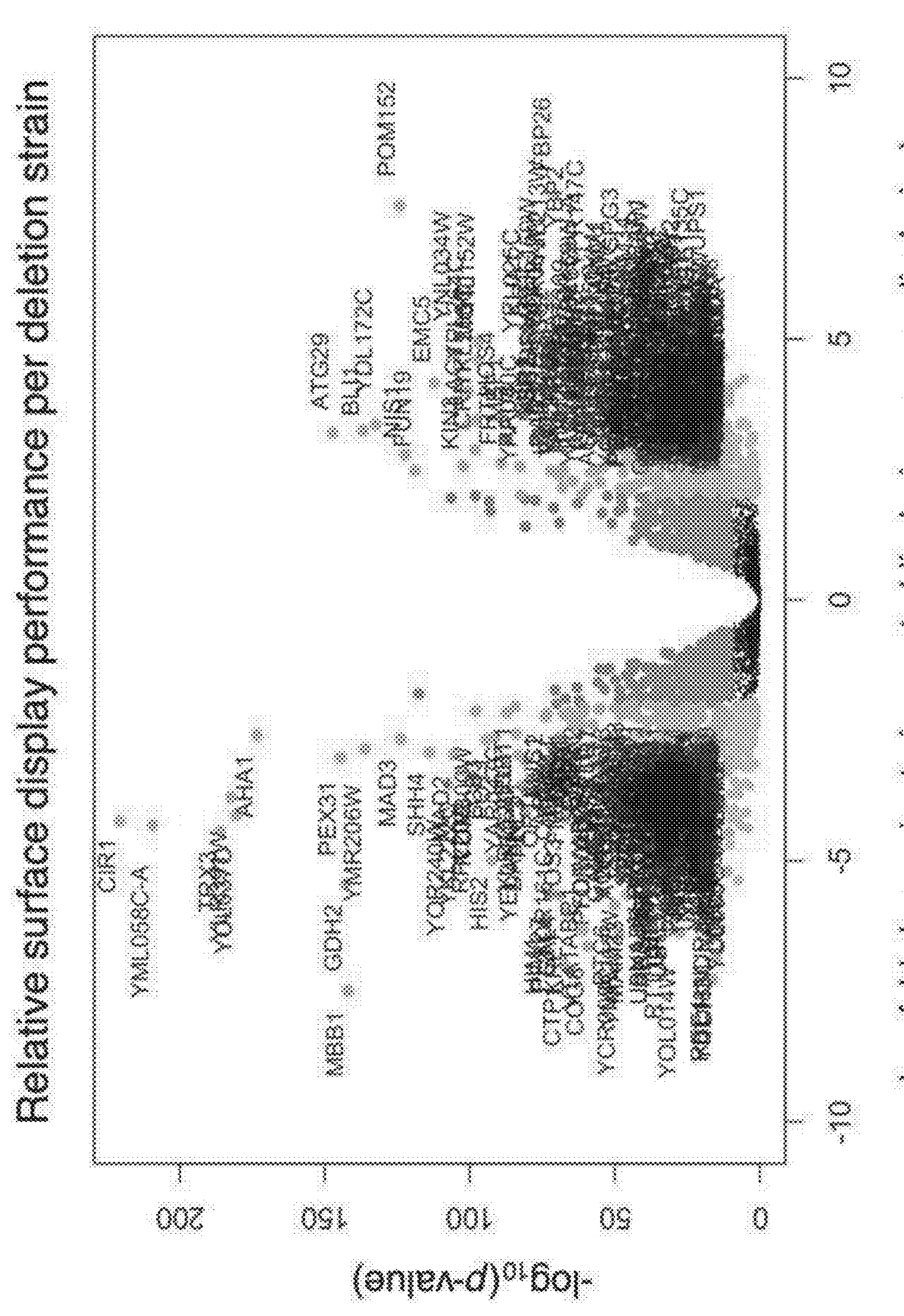
FIG. 6 illustrates a volcano plot illustrating exemplary embodiments that exhibit displaying and non-displaying organisms in accordance with various embodiments.

FIG. 6 illustrates a volcano plot of an exemplary embodiment illustrating calculated certainty levels (p-values) across four independent sorts against the relative abundance of each mutant strain between "displaying" and "non-displaying" sort bins, taken as a $\log_2$ fold change.

EXEMPLARY EMBODIMENTS

Although the following embodiments provide details on certain embodiments of the inventions, it should be understood that these are only exemplary in nature, and are not intended to limit the scope of the invention.

Example 1: Expressing Lignin-Modifying Enzymes in *S. cerevisiae*

Methods: The homozygous diploid yeast deletion collection was kindly provided in pooled format by the Stanford Genome Technology Center and propagated as previously described in YPD. Transformation of the peroxidase-surface display fusion vector pL158A-HRP was carried out by the lithium acetate method and plated on synthetic defined media plates lacking leucine to select for transformants. Transformants were pooled from 8 plates into YPD+15% w/v glycerol giving at least 36000 transformants for pL158A-HRP and were frozen at −80° C.

27 μl of library stock was used to start a 2 ml non-inducing, non-repressing synthetic defined medium containing 2% raffinose and 1% sucrose lacking leucine for auxotrophic selection. After 20 hours growth (30° C., 300 rpm), 100 ul culture was diluted into 2.9 ml synthetic defined medium containing 4% galactose and lacking leucine. After 16 hours induction (20° C., 300 rpm), 10 million cells were harvested in quadruplicate and labeled as previously described31. Briefly, cells were washed twice with 1 ml buffer (PBS+0.1% BSA) before being resuspended in biotinyl tyramide reaction buffer (100 μM biotinyl tyramide, 100 μM hydrogen peroxide, PBS+0.1% BSA, pH 7.4) at cell density of 106 cells per ml in 15-ml conical centrifuge tube. Cells were labeled statically on ice for 5 minutes before quenching with 0.5 ml buffer containing Trolox™ (6-hydroxy-2,5,7,8-tetramethylchroman-2-carboxylic acid) (10 mM Trolox™ in PBS+0.1% BSA). Cells were pelleted into a 1.5-ml microcentrifuge tube and washed twice with buffer. Samples were labelled using a 1/50 dilution of anti-Myc-AlexaFluor647 conjugate (Cell Signaling Technologies™) and a 1/10 dilution of streptavidin-phycoerythin conjugate (Jackson Laboratories™) in 200 μl buffer for 1.75 hours at 4° C. in the dark with rotation. Samples were washed twice with 200 μl buffer and immediately use for cell sorting.

Fluorescence-assisted cell sorting was performed on a Sony SH800 cell sorter with compensation for PE and AlexaFluor647™ channels. 1.2 to 1.4 million events were sorted in total for the four replicates, collecting cells in 3 ml synthetic defined medium containing 2% glucose and lacking leucine. "Unsorted" control samples were prepared by collecting all events into a single culture. Genomic DNA was extracted using a YeaStar Genomic DNA Kit™ (Zymo Research™) after 21 hours outgrowth (30° C., 300 rpm). "Non-displaying", "displaying", and "unsorted" samples showed comparable final cell densities. Cultures were backdiluted into inducing growth media as above after 26 hours outgrowth to validate sorting. Biotinyl tyramide labeling was performed as above, and fluorescent labeling was performed at 1/100 and 1/50 dilutions, respectively.

2 μl of genomic DNA was used to amplify strain barcodes by PCR (Q5® NEB master mix, 22 cycles) using primers containing sequence-optimized spacers to maximize nucleotide diversity in Illumina™ sequencing. DNA amplification was performed with two different spacer primers as technical duplicates to minimize PCR amplification bias due to primer sequence. PCR products were gel-purified and used for a second round of PCR amplification (Q5® NEB master mix, 7 cycles) using custom primers to attach Illumina read sequences. PCR products were gel purified and their concentration quantified using a Qubit™. Products were pooled and sequenced using an Illumina™ HiSeq 4000 2×75 bp. Strain-barcode matching and counting were performed using a Levenshtein distance of 2 and neglecting barcodes appearing only once. Statistical analysis was performed using the edgeR software package in R, taking raw count data from replicate sort samples as data input. An adjusted counts per million of more than 10 in at least 6 samples was used to filter out strains with low abundance. Log fold change of strain counts between "displaying" and "non-displaying" samples were used to assess gene deletion effect on secretion.

Individual single null mutant strains pom152, ybp2, cym1, vps30, cyt2, pmt2, qdr2, vps38, ssh1, scs2, ssb1 and ho were propagated on YPD plates. Double knockout strains were constructed by homologous recombination in the pmt2 mutant background using his3 and ura3 as selectable markers to replace cyt2. Transformation of pL158A vectors was performed using the lithium acetate method with selection on synthetic defined plates lacking leucine. Transformants were picked into 96-well plates with synthetic defined growth medium containing 2% glucose and lacking leucine and grown overnight (24 hours, 30° C., 450 rpm). Cultures were diluted 1/10 into YP medium containing 2% galactose and 3% glycerol and induced for 4 days (20° C., 450 rpm). Peroxidase activity was assayed using a Synergy™ HTX plate reader at 25° C. using 10 mM ABTS, 100 μM hydrogen peroxide, and one of the following: 50 mM potassium phosphate, pH 6.0, for horseradish peroxidase; 50 mM sodium tartrate, pH 3.5, for versatile and lignin peroxidases; and 50 mM sodium malonate, pH 4.5, and 1 mM MnSO4 for manganese peroxidases.

Results: Since most lignin-degrading peroxidases have limited heterologous secretion in yeast, the focus of this embodiment was on horseradish peroxidase (AR-hrp) as a model heme peroxidase with structural similarity to lignin-degrading peroxidases and has detectable secretion by *S. cerevisiae*. In order to rapidly screen strains for secretion ability, yeast surface display was chosen as a reliable proxy for secretion to enable pooled library screening by FACS. Previously described labeling methods involving biotinyl tyramide were adapted to screen based on both enzyme production as well as activity, ensuring that the enzyme is properly folded and functional in yeast strains displaying greater protein levels.

A homozygous deletion collection background containing barcoded knockouts of each non-essential gene in yeast was used. A galactose-inducible vector that allowed plasmid-based expression of both the AGA1 scaffold protein and AGA2 fusion protein for surface display of horseradish peroxidase was cloned. After binning based on the presence or absence of displayed functional enzyme ("productive" versus "non-productive" cells), a barcode counting approach was employed to quantify the abundance of each deletion strain in the two bins by next-generation sequencing. Impact on secretion was determined using the log fold change in abundance between the two bins (FIG. 6). 546 strains showed statistically significant improvement in surface display (log fold change >2, p-value <1e-10), of which 12 were manually selected for subsequent characterization based on ontological relation to the secretory pathway.

Production of horseradish peroxidase was compared in these 12 mutant strains to that in a silent deletion strain (Δho) generally accepted as a wildtype control. Even with a growth defect resulting from an inability to utilize nonfermentable carbon sources (FIGS. 3A-3B), BY4743Δcyt2, consisting of the deletion of cytochrome c1 heme lyase, showed significant improvement in horseradish peroxidase secretion (3.38-fold greater than wildtype after OD600 normalization), especially in the absence of heme supplementation in culture media (9.10-fold) (FIGS. 2A-2B). Without heme and calcium media supplementation, BY4743Δqdr2 and BY4743Δpom152 also showed statistically significant enhancement in secretion (1.75- and 1.31-fold, respectively). The heterologous production of a versatile peroxidase was also from the lignin-degrading fungus *Pleurotus eryngii* (PE-vp12) with low levels of secretion in *S. cerevisiae*. The results indicated that secretion improvements due to deletion of cyt2 were translatable to this peroxidase as well, resulting in a 4.65-fold improvement in secretion with media supplementation (FIGS. 2A-2B). However, deletion of the 0-glycosyltransferase pmt2 had the strongest effect on secretion of PE-vp12, improving secretion 9.45-fold with media supplementation and 2.68-fold without.

Based on these results, heme cofactor incorporation and proper glycosylation appeared to be important yet sequential steps in the folding and processing of PE-vp12. It was hypothesized that the effects of deleting cyt2 could be epistatic to those of deleting pmt2 and constructed a double knockout BY4743Δcyt2Δpmt2 to test this hypothesis. In attempt to help mitigate the growth defect caused by a homozygous cyt2 knockout, a double knockout heterozygous in the cyt2 locus (BY4743Δcyt2$^{-/+}$Δpmt2$^{-/-}$) was also constructed. Normal growth was observed in this heterozygous double knockout but surprisingly secretion of either peroxidase was reduced to that of wildtype both with and without media supplementation. The homozygous double knockout BY4743Δcyt2Δpmt2 displayed growth defect but significantly outperformed either single knockout in secretion of either peroxidase, confirming an epistatic hypothesis (AR-hrp, 25.2-fold relative to wildtype; PE-vp12, 57.0-fold; values after OD600 normalization) (FIG. 4). Given the substantial improvements in secretion afforded by these two gene knockouts, it was asked whether these effects were applicable to lignin-degrading peroxidases more broadly. Secretion testing was expanded to include another versatile peroxidase from a different lignin-degrading fungus *Pleurotus ostreatus* (PO-vp1), a lignin peroxidase from *Gelatoporia subvermispora* (GS-lip1), and a manganese peroxidase from *Phanerochaete chrysosporium* (PC-mnp1). Almost undetectable levels of secretion were observed in wildtype BY4743. Remarkably, deletion of cyt2 and pmt2 individually enabled detectable levels of secretion for all three lignin-degrading peroxidases (FIG. 4). Moreover, the homozygous double mutant showed strong epistatic effects, particularly for PO-vp1 (8.3-fold increase relative to Δcyt2 alone). These results indicate the BY4743Δcyt2Δpmt2 significantly improves heterologous secretion of both class II fungal and class III plant heme peroxidases, and even enables secretion of lignin-degrading peroxidases having no detectable levels in wildtype BY4743.

Western blotting of culture supernatants and whole cell extracts was performed to better understand the effects of the gene knockouts on the molecular properties of PE-vp12 (FIGS. 7A-7B). Western blotting of whole cell extracts showed bands specific to PE-vp12 in all strains tested, indicating transcription and translation are not rate-limiting in the secretion of this peroxidase (FIG. 7A). BY4743Δho displayed bands at and above the expected unglycosylated molecular weight of PE-vp12 (36 kDa), with higher molecular weight bands presumably corresponding to increasingly glycosylated forms of the enzyme. Surprisingly, deletion of pmt2 did not result in a noticeable effect on the molecular weight of the bands observed, although an increased amount of protein is evident. Deletion of cyt2 resulted in a greater abundance of lower molecular weight bands, while the double deletion strain reflected a band pattern similar to the single pmt2 deletion with greater protein levels as in the case of the single cyt2 deletion. Bands at molecular weights lower than the expected size of the enzyme were also evident in strains deleted in cyt2, suggesting possible proteolysis. Blotting of extracellular protein revealed a single predominant band at molecular weight much higher than the dominant bands evident from intracellular blotting (FIG. 7B). This suggests that at steady state, the majority of the produced PE-vp12 is held up within the cell as evidenced by major bands at lower molecular weight, and only a heavily glycosylated form of the enzyme is secreted into the culture supernatant. Extracellular blotting also revealed that deletion of pmt2 results in a decrease in molecular weight of the secreted enzyme glycoform, while deletion of cyt2 enables increased secreted protein levels. Protein levels in extracellular blotting correlated well with observed activity towards ABTS in the context of single and double mutant testing focused on pmt2 and cyt2 (FIG. 4), with the latter deletion displaying both highest activity levels as well as extracellular protein levels in the case of PE-vp12. Differences in growth due to cultivation conditions for the slow-growing, respiratory-deficient cyt2 strain may explain the difference in observed activity levels between screening of the 12 selected mutants (FIGS. 2A-2B) versus that of pmt2 and cyt2 mutants (FIG. 4). Taken together, these data indicate that deletion of pmt2 and cyt2 result in increased secreted protein levels, resulting in greater observed extracellular ABTS activity levels, and that the deletion of both genes yields further improvements.

Discussion: The improvement in secretion due to deletion of cyt2, cytochrome c heme lyase, reveals that heme biosynthesis and/or trafficking is a limiting factor. *S. cerevisiae* does not have any known transporters specialized for exogeneous heme, yet media supplementation with free hemin was shown to be beneficial in this study. In the production of cytochromes P450, heme biosynthesis has been shown to be an engineering target for protein yield improvements and previous studies have achieved improved peroxidase production through supplementation with heme precursors and upregulation of the heme biosynthetic pathway. Cyt2 however is not directly involved in heme biosynthesis but utilizes heme for maturation of cytochrome c143. This suggests that reducing heme demand through deletion of cyt2 yields more available heme for the production of heterologous heme peroxidases. Greater heme availability may also allow greater production of native peroxide-detoxifying enzymes such as cytochrome c peroxidase and catalase, mitigating possible oxidative effects of heterologous peroxidase expression in the secretory pathway. This deletion however results in an inability for the strain to grow on non-fermentable carbon sources, meaning that while cellular productivity is increased, cell density under inducing, protein-producing conditions is limited. Nevertheless, this result indicates that cyt2 presents an important candidate for further strain engineering efforts. For example, complementation by cyt2 homologs or evolution of cyt2 variants having reduced function would mitigate growth defects while increasing the supply of heme available for heterologous proteins. Moreover, factors involving the transport of heme into the secretory pathway remain unknown and could further enhance peroxidase secretion in conjunction with cyt2 expression modulation.

Figure 7:
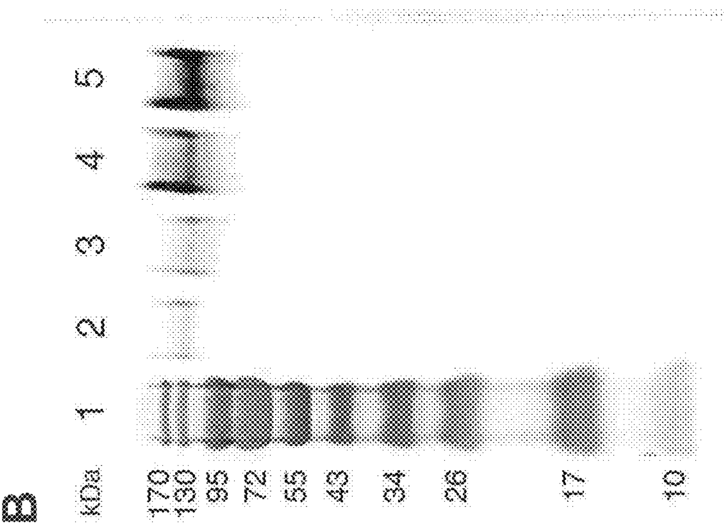
FIGS. 7A-7B illustrate exemplary western blots of enzymes produced in accordance with various embodiments.
Figure 7:
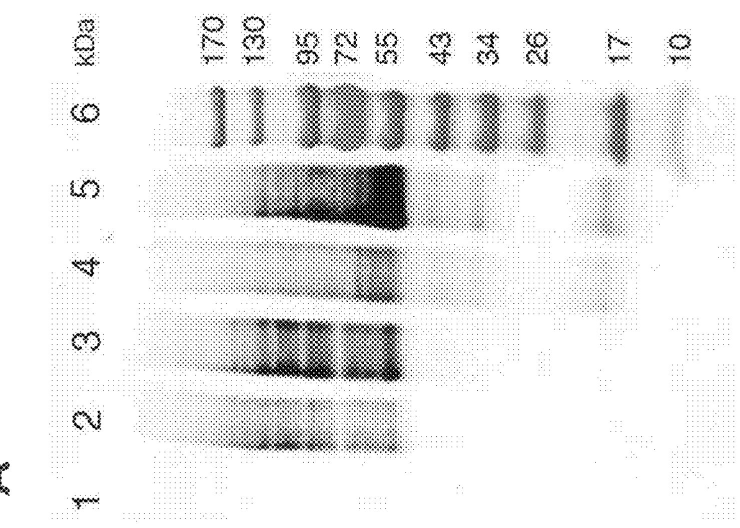

This screen revealed that deletion of pmt2 had the greatest positive impact on secretion of fungal lignin-degrading peroxidases of the mutants tested. This effect was notably observed for multiple members from different lignin-degrading peroxidase classes from a variety of fungal species, suggesting that a general feature of this enzyme class results in misprocessing in yeast. Pmt2 is a member of the family of 0-mannosyltransferases involved in ER protein quality control. Fungal lignin-degrading peroxidases are known to have both N- and O-linked forms of glycosylation of the simple mannose type. Western blotting of intercellular as well as extracellular protein fractions revealed bands presumably corresponding to glycoforms of PE-vp12 at very high molecular weight (FIG. 7). Hyperglycosylation is a previously characterized challenge in secretion of heterologous proteins in *S. cerevisiae*, including that of horseradish peroxidase. Repeated mannosyl transfer would yield a sterically hindered protein that may pose greater difficulty in export through the yeast peptidoglycan cell wall matrix. Why pmt2 appears to target fungal lignin-degrading peroxidases in particular for excessive glycosylation is unclear. Despite their structural and glycosylation similarities, the effect of pmt2 deletion was significantly greater for this class enzymes compared to horseradish peroxidase. This suggests protein sequence determinants for misprocessing by pmt2. As an ER protein quality control component, targeting by pmt2 also seems to indicate protein misfolding issues. Incubation of PE-vp12-expressing cells in the presence of colorimetric peroxidase substrates (e.g. ABTS) gave no color change. As these substrates could be expected to diffuse into the yeast cell wall, this suggests that the enzyme is either trapped but inactive within the cell wall matrix, or otherwise does not reach the cell periphery.

Conclusion: The combination of cyt2 and pmt2 deletions revealed synergistic effects on secretion of all peroxidases tested. This study demonstrates that single null mutant screening affords significant improvements in heterologous protein production and more importantly serves as a proof-of-concept to enable subsequent screens focusing more on epistatic effects of gene expression modulation. Deletion and/or overexpression of other native yeast genes in the context of the cyt2/pmt2 deletion strain background would almost certainly yield further secretory improvements, which may have had only modest effects in the context of the wildtype strain background. Variable gene expression modulation using, for example, plasmid-based CRISPRi/a libraries would greatly expand the scope by enabling screening of essential yeast genes, facilitating rapid testing of library member combinations, and identify optimal levels of gene expression. While this study searched for components native to yeast that prevented successful production of lignin-degrading peroxidases, it may be that yeast lack components present in lignin-degrading fungi required for proper folding and processing of these enzymes. These may be identified for example by screening strains co-expressing genomic cDNA libraries from lignin-degrading fungi using the same strategy described in this study. Finally, we anticipate this study to serve as the first step towards directed evolution of cellular components rather than of proteins of interest to improve heterologous production. The genomic targets identified here can be mutagenized and screened for variants with greater secretion enhancement than by deletion of those targets alone while minimizing impacts on cell growth. Methods involving in vivo mutagenesis and continuous selection currently being developed would further accelerate this approach. The results of these efforts would help augment our understanding of factors implicated in heterologous protein production, expanding our ability to reliably and efficiently produce valuable protein-based therapeutics and catalysts at scale.

DOCTRINE OF EQUIVALENTS

Although specific methods of producing lignin-modifying enzymes are discussed above, many production methods can be used in accordance with many different embodiments of the invention, including, but not limited to, methods that use other plant hosts, other bacterium, and/or any other modification as appropriate to the requirements of specific applications of embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A transgenic yeast organism comprising:

a knockout of a first native gene and a knockout of a second native gene, wherein the first native gene is cyt2 encoding cytochrome c heme lyase and the second native gene is pmt2 encoding protein O-mannosyltransferase 2; and an expression cassette comprising a nucleotide sequence encoding for a lignin-modifying enzyme.

2. The transgenic yeast organism of claim 1, wherein the lignin-modifying enzyme is a heme peroxidase.

3. The transgenic yeast organism of claim 1, wherein the nucleotide sequence encoding the lignin-modifying enzyme is one of SEQ ID NOs: 1-78.

4. The transgenic yeast organism of claim 1, wherein the expression cassette further comprises a nucleotide sequence encoding a scaffold protein and a surface display protein, wherein the surface display protein is linked to the lignin-modifying enzyme, such that a hybrid peptide is produced with the lignin-modifying enzyme and the surface display protein.

5. The transgenic yeast organism of claim 1, wherein the expression cassette further comprises an inducible promoter operatively linked to the nucleotide sequence encoding the lignin-modifying enzyme.

* * * * *

```
                         SEQUENCE LISTING

<160> NUMBER OF SEQ ID NOS: 81

<210> SEQ ID NO 1
<211> LENGTH: 1032
<212> TYPE: DNA
<213> ORGANISM: Phanerochaete chrysosporium

<400> SEQUENCE: 1

gctacctgtt ctaacggtaa gactgtcggt gacgcttcct gttgtgcttg gtttgatgtt      60

ttggacgaca ttcaacaaaa cttgttccac ggtggtcaat gtggtgctga agctcatgaa     120

tctattcgtt tggttttcca cgactctatc gctatttccc cagctatgga agctcaaggt     180

aaattcggtg gtggtggtgc tgatggttca attatgatct tcgacgacat cgaaaccgct     240

ttccatccaa acattggttt ggacgaaatt gttaagttgc aaaagccatt cgtccaaaag     300

cacggtgtta ctccaggtga ctttattgcc ttcgctggta gagttgcttt gtctaactgt     360

ccaggtgctc cacaaatgaa cttcttcacc ggtagagctc cagctaccca accagctccc     420

gacggtttgg tcccagaacc attccacact gttgaccaaa ttatcaacag agttaacgac     480

gctggtgaat ttgacgaatt ggaattggtt tggatgttga gcgctcactc cgtcgctgct     540

gttaacgacg tcgacccaac cgttcaaggt ttgccattcg actccacccc aggtatcttc     600

gactcccaat tcttcgttga aacccaattg agaggtaccg cttttccagg ttccggtggt     660

aaccaaggtg aagtcgaatc cccattacca ggtgaaatta gaatccaatc cgaccacacc     720

attgctagag attctagaac tgcctgtgaa tggcaatcct tcgttaacaa ccaatctaag     780

ttggtcgatg actttcaatt cattttcctt gcccttactc aactgggtca ggacccaaac     840
```

```
gctatgactg attgttctga tgttattcca caatccaagc caattccagg taacttgcca    900

ttctccttct tcccagctgg taagaccatc aaggacgttg aacaagcttg tgctgaaacc    960

ccattcccaa ccttaactac cttgccaggt ccagaaacct ccgttcaaag aatcccacca   1020

ccaccaggtg ct                                                        1032
```

<210> SEQ ID NO 2
<211> LENGTH: 1032
<212> TYPE: DNA
<213> ORGANISM: Phanerochaete chrysosporium

<400> SEQUENCE: 2

```
gctacttgtt ctaacggtgc caccgttggt gacgcctcct gctgtgcttg gttcgacgtt     60

ttggacgata ttcaacaaaa cttgtttcaa ggtggtcaat gtggtgccga agctcacgaa    120

tccatcagat tggttttcca cgatgccatt gctatttctc cagctatgga agctcaaggt    180

aagttcggtg gtggtggtgc tgatggttct atcatgatct ttgatgacat cgaaccaaac    240

ttccacccaa acatcggttt ggacgaaatt atcaacttac aaaagccatt cgttcaaaag    300

cacggtgtca ctccaggtgc cttcattgct ttcgccggtg ctgtcgcctt gtccaactgt    360

ccaggcgccc cacaaatgaa cttctttact ggtagagctc cagccactca accagctcca    420

gatggtttgg tccctgaacc attccacacc gttgaccaaa ttatcgccag agtcaacgac    480

gccggtgaat tcgatgaatt ggaattggtt tggatgttgt ctgcccactc tgttgctgcc    540

gttaacgacg tcgaccctac tgttcaaggt ttgccatttg attctacccc tggtatcttc    600

gactctcaat tctttgtcga aactcaattc agaggtattt tgttcccagg ttccggtggt    660

aaccaaggtg aagttgaatc cggtatggct ggtgaaatca gaattcaaac tgatcacacc    720

ttggccagag attctagaac cgcttgtgaa tggcaatctt tcgtcaacaa ccaatccaag    780

ctggttagtg acttccaatt catcttcttg gcgttaactc aattgggtca ggacccaaac    840

gctatgactg attgttctga cgttatccct atttctaagc caatcccagg taacttgcct    900

ttctccttct tcccaccagg taagtccatg aaggacgttg aacaagcctg tgctgaaacc    960

cctttcccat ctttggtcac tttgccaggt cctgctacct ccgttgctag aatcccacca   1020

ccaccaggtg cc                                                        1032
```

<210> SEQ ID NO 3
<211> LENGTH: 1032
<212> TYPE: DNA
<213> ORGANISM: Phanerochaete chrysosporium

<400> SEQUENCE: 3

```
gctacttgtt ctaacggtaa ggttgttcca gctgcctcct gttgtacctg gtttaacgtt     60

ttgtctgaca ttcaagaaaa cttgttcaac ggtggtcaat gtggtgctga ggctcacgaa    120

tctatccgtt tggttttcca tgatgctatc gctatctccc cagctatgga accccaagcc    180

tcctctgtca gaggtgctga cggttccatt atgatcttcg atgaaattga aactaacttc    240

cacccaaaca tcggtttgga tgaaatcgtt agattgcaaa agccattcgt tcaaaagcat    300

ggtgttaccc caggtgattt cattgctttc gctggtgctg tcgctttgtc caactgtcca    360

ggtgctccac aaatgaactt cttcactggt agagccccag ctactcaacc agccccagac    420

ggtttggtgc cagaaccatt ccactcagtt gaccaaatca tcgatagagt tttcgacgcc    480

ggtgagttcg atgaattgga attggtctgg atgttgtccg ctcacagcgt tgctgctgct    540
```

```
aacgacatcg atccaaacat ccaaggtttg ccattcgatt ccactccagg tattttcgac    600

tcccaattct tcgtcgaaac tcaattggct ggtaccggtt tcaccggtgg ttccaacaac    660

caaggtgaag tttcctctcc attgccaggt gaaatgagat tgcaatccga tttcttgatc    720

gctcgtgacg ctagaaccgc ttgtgaatgg caatctttcg tcaacaacca atcaaagttg    780

gtttccgatt tccaattcat cttcttggct ttgactcaat tgggtcaaga ccctgacgct    840

atgaccgatt gttctgctgt tattccaatc tccaagccag cccctaacaa cactccaggt    900

ttctccttct tcccaccagg tatgactatg gatgacgttg aacaagcttg tgctgaaacc    960

ccattcccaa ctttaagcac tttgccaggt ccagccacct ctgttgctag aattccacca   1020

ccaccaggtg ca                                                        1032
```

<210> SEQ ID NO 4
<211> LENGTH: 1032
<212> TYPE: DNA
<213> ORGANISM: Phanerochaete chrysosporium

<400> SEQUENCE: 4

```
gttgcttgtc cagacggtgt tcacaccgct tcaaacgctg cctgttgcgc ttggttccca     60

gttttggatg acatccaaca aaacttgttc cacggtggtc aatgtggtgc tgaagctcac    120

gaagctttga gaatggtttt tcatgactcc attgccattt ctccaaagtt gcaatctcaa    180

ggtaagttcg gtggtggtgg tgctgatggt tccatcatta ctttctcctc tatcgaaacc    240

acctaccacc caaacattgg tttggacgaa gtcgttgcca ttcaaaagcc attcatcgct    300

aagcatggtg ttactagagg tgacttcatc gccttcgctg gtgctgttgg tgtctccaac    360

tgtccaggtg ctccacaaat gcaatttttc ttgggtagac cagaagctac tcaagctgct    420

ccagacggtt tggttccaga accattccac actattgacc aagtcttggc tagaatgttg    480

gacgctggtg gttttgacga aattgaaact gtttggttgt tgtctgccca ctccatcgct    540

gctgccaacg atgtcgaccc aaccatttct ggtttaccat tcgactccac cccaggtcaa    600

tttgactctc aattcttcgt tgaaactcaa ttgagaggta ccgctttccc aggtaagacc    660

ggtatccaag gtactgtcat gtctccattg aagggtgaaa tgagattgca aactgatcac    720

ttattcgcca gagactccag aaccgcttgt gaatggcaat cctttgtcaa caaccaaacc    780

aagttgcaag aagattttca attcattttc actgccctat ctactttggg tcacgacatg    840

aacgctatga ccgactgttc tgaagttatt ccagccccaa agccagttaa ctttggtcca    900

tccttcttcc cagctggtaa gacccatgct gacattgaac aagcctgtgc ctctactcct    960

ttcccaacct tgatcaccgc tccaggtcca tccgcttctg ttgccagaat tccaccacca   1020

ccatctccaa ac                                                        1032
```

<210> SEQ ID NO 5
<211> LENGTH: 1029
<212> TYPE: DNA
<213> ORGANISM: Phanerochaete chrysosporium

<400> SEQUENCE: 5

```
gctacttgtg ccaacggtaa gaccgttggt gacgcttctt gttgtgcttg gttcgacgtc     60

ttggatgaca tccaagctaa catgttccac ggtggtcaat gtggtgccga agcccacgaa    120

tccatcagat tggttttcca cgactccatc gctatctctc cagctatgga agccaagggt    180

aagttcggtg gtggtggtgc cgacggttct atcatgatct tcgatactat cgaaaccgct    240

ttccacccaa acatcggttt ggacgaagtt gtcgctatgc aaaagccatt cgttcaaaag    300
```

```
cacggtgtta ctccaggtga cttcattgct ttcgccggtg ctgttgcctt gtcaaactgt    360

ccaggtgctc cacaaatgaa cttcttcact ggtagaaagc cagccaccca accagctcca    420

gacggtttgg tcccagaacc atttcacacc gtcgatcaaa tcattgctag agttaacgac    480

gctggtgaat tcgacgaatt ggaattggtt tggatgttgt ccgcccactc tgttgctgcc    540

gtcaacgacg ttgacccaac cgttcaaggt ttgccattcg attctactcc aggtatcttc    600

gactctcaat tcttcgttga aactcaattc agaggtacct tgttcccagg ttccggtggt    660

aaccaaggtg aagtcgaatc cggtatggcc ggtgaaatta gaatccaaac tgatcacacc    720

ttggctagag attctagaac tgcttgtgaa tggcaatcct tcgttggtaa ccaatctaag    780

ttggtcgacg atttccaatt catcttcttg gctttgactc aattgggtca agatccaaac    840

gctatgactg actgttctga tgttatccca ttgtctaagc caatcccagg taacggtcca    900

ttctccttct tcccacctgg taagtctcac tccgatattg aacaagcttg tgccgaaact    960

ccattccctt ccttggtcac cttgccaggt ccagctacct ctgttgctag aatcccacca   1020

cacaaggct                                                          1029
```

<210> SEQ ID NO 6
<211> LENGTH: 1029
<212> TYPE: DNA
<213> ORGANISM: Phanerochaete chrysosporium

<400> SEQUENCE: 6

```
gccacctgtt ccaacggtgc taccgtcggt gacgcttcca gctgtgcttg gttcgatgtt     60

ttggacgaca ttcaacaaaa cttatttaac ggtgctcaat gtggtgctga agctcacgaa    120

tccattagat tggttttcca cgatgctatc gccatttctc cagctttgga atctcaaggt    180

aagtttggtg gtggtggtgc cgacggttcc atcattttgt tcgatgacat tgaaactaac    240

ttccacccaa acatcggttt ggatgaaatc gtcaacttgc aaaagccatt tattcaaaag    300

cacggtgtca ccccaggtga cttcatcgct ttcgctggtg ctgtcgctat gtccaactgt    360

ccaggtgccc cacaaatgaa cttctttacc ggtcgtgctc cagccactca agctgctcca    420

gatggtttag tcccagaacc attccatact gtcgatcaga tcatttctag agtcaacgac    480

gctggtgaat tcgacgaatt ggaattggtt tggatgttgt ccgctcactc cgttgctgcc    540

gctaacgacg ttgatccaac cattcaaggt ttggctttcg actctactcc aggtgtattc    600

gactcccagt tttttgttga aacccaattg cgtggtactg ctttcccagg ttccggtggt    660

aaccaagggg aagttgaatc tccattgcca ggtgaaatga gattgcaatc cgattcttcc    720

attgccagag attctagaac cgcttgtgaa tggcaatcct tcgttaataa ccaatctaag    780

ttagtctccg atttccaatt cattttcttg gccttgaccc aattgggtga aaacccagat    840

gctatgaccg attgttctga cgtcatccca atctccaagc cagtcccaaa caacgtccct    900

ttctctttct tcccagctgg taagactatg gctgatgttg aacaagcctg tgctgaaact    960

ccatttccaa ctttgaccac cttgccaggt ccagaaacct ccgtccaaag aattccacca   1020

ccaggtgcc                                                          1029
```

<210> SEQ ID NO 7
<211> LENGTH: 1032
<212> TYPE: DNA
<213> ORGANISM: Phanerochaete chrysosporium

<400> SEQUENCE: 7

```
gctacctgtt ctaacggtgc aactgtctct gacgcttcct gttgtgcttg gttcgatgtc     60

ttggacgata tccaacaaaa cttgttccaa ggtggtcaat gtggtgctga agctcatgag    120

tctatcagat tggtttttca cgactccatc gctatctctc cagctatgga agctcaaggt    180

aagttcgggg gtggtggtgc tgatggttcc atcatcatct tcgacaccat cgaaactgct    240

ttccacccaa acatcggttt ggatgaaatc gtcaacttgc aaaagccatt catcgctaag    300

catggtgtca ccccaggtga cttcatcgct tttgctggtg ctgttgcttt gtccaactgt    360

ccaggttccc cacaaatgaa cttctttacc ggtagagctc ctgccaccaa ggctgcccct    420

gacggtttgg tcccagaacc attccacacc gttgatcaat tgattgaaag agtcaacgac    480

gctggtcaat tcgacgaatt agaattggtt tggatgttgt ccgctcattc tgttgctgct    540

gtcaacgacg tcgatccaac cgtccaaggt ttgccattcg actccactcc aggtattttc    600

gattctcaat tttcgtcga aacccaattg cgtggtttga ctttcccagg ttccggtggt    660

aaccaaggtg aagttacctc cccattgcca ggtgaaatca gaatccaaac cgatcacact    720

ttggctcgtg actccagaac cgcttgtgaa tggcaatctt tcgtcgccaa ccaatccaag    780

ctggtcagtg acttccaatt cattttctta gctttgaccc agttgggtca agacccaaac    840

gctatgaccg actgttccga cgtcattcca atttccaagc caatcccagg taacttgcct    900

ttctctttct tcccagctgg taagaccatg aaggacgtcg aacaagcctg tgctgaaact    960

ccattcccat ccttgaccac cttgccaggt ccagaaactt ctgttcaaag aatcccacca   1020

cctccaggtg ca                                                        1032
```

<210> SEQ ID NO 8
<211> LENGTH: 1032
<212> TYPE: DNA
<213> ORGANISM: Phanerochaete chrysosporium

<400> SEQUENCE: 8

```
gctacctgtt ctaacggtgc caccgttggt gacgaatctt cctgcgcttg gtttgatgtt     60

ttagatgata tccaagaaaa cttgttccaa ggtgctcaat gtggtgccga ggctcacgaa    120

tccattagat tggttttcca tgacgctatc gccatttccc cagctatgga agcccaaggt    180

caattcggtg gtggtggtgc tgatggttct atcattatct tcgacaccat tgaaaccgcc    240

ttccacccaa acatcggttt ggatgaaatt gttaatttgc aaaagccatt cattgctaag    300

cacggtgtca ccccaggtga cttcattgct ttcgctggtg ctgtcgcttt gtcaaactgt    360

ccaggtaccc cacaaatgaa cttcttcact ggtagagctc cagctaccca agccgcccca    420

gacggtttgg tccctgaacc attccacacc gtcgatcagt tgatcaacag agttaacgac    480

gctggtcaat tcgacgaatt ggaattggtc tggatgttgt ctgctcattc cgttgccgct    540

gtcaacgacg ttgatccaac tattcaaggt ttggcttttg actccactcc tggtatcttc    600

gattctcaat tcttcgttga aacccaattg agaggtactg ctttcccagg ttctggtggc    660

aaccaaggtg aagttgaatc tccattgcca ggtgaaatta gaatccaaac cgaccacact    720

ttggctagag atccaagaac cgcctgtgaa tggcaatcct tcgttgccaa ccaatctaag    780

ttagttagtg atttccaatt catcttcttg gccctaactc aattgggtca agacccaaac    840

gctatgaccg attgttccga tgttatccca atctccaagc caattccagg tgacttgcca    900

ttctctttct tcccagctgg taagaccgcc gctgatgtcg aacaagcttg tgccgaaact    960

ccattcccat ccttgaccac cttgccaggc ccagaaactt ctgttcaaag aatcccaccc   1020

ccaccaggtg cc                                                        1032
```

<210> SEQ ID NO 9
<211> LENGTH: 1020
<212> TYPE: DNA
<213> ORGANISM: Phanerochaete chrysosporium

<400> SEQUENCE: 9

```
gctacttgtg ctaacggtgt cactgttggt gatgcttcct gttgcgcctg gtttgatgtt     60

ttggacgata tccaagaaaa cttgttccac ggtggtcaat gtggtgccga agctcacgaa    120

tccattagat tggttttcca tgactccatc gcaatttctc cagctatgga agcccagggt    180

aagttcggtg gcggtggtgc tgatggttct attatgatct tcgacgacat cgaaaccgct    240

ttccacccaa atatcggttt ggacgaaatt gtcaagttgc aaaagccatt cgttcaaaag    300

cacaacgtca ccccaggtga ttttatcgct ttcgctggtg ctgttgcctt gtccaactgt    360

ccaggtgccc cacaaatgaa cttcttcact ggtagagctc cagccccaga cggtttggtc    420

ccagaaccat tccacaccgt cgatcaaatt atctctagag ttaacgatgc tggtcaattc    480

gatgaattgg aattggtttg gatgttatct gctcactctg ttgctgccgt taacgacgtt    540

gacccaaccg tccaaggttt gccattcgat tccactccag gtattttcga ctctcaattc    600

ttcgttgaaa cccaattgag aggtaccgct tttccaggtt ccggtggcaa ccaaggtgaa    660

gtcgaatccc cattgcctgg tgaattcaga atccaatcag atcacaccat cgctagagat    720

tctagaaccg cttgtgaatg gcaatccttc gtcaacaacc aaagcaagct ggtgagtgac    780

ttccaattca tcttcttggc cttgactcaa ttaggtcaag acccaaacgc tatgaccgac    840

tgttcagacg ttattccaca atctaagcca atcccaggga atttaccatt ctctttttc     900

ccagctggta agaccattaa cgatgttgaa caagcttgtg ccgaaacccc attcccaact    960

ttgactacct tgccaggtcc agaaacctcc gttcaaagaa tcccaccacc accaggtgct   1020
```

<210> SEQ ID NO 10
<211> LENGTH: 1026
<212> TYPE: DNA
<213> ORGANISM: Phanerochaete chrysosporium

<400> SEQUENCE: 10

```
gccacctgtt ccaacggtaa aactgtctct tctgctgctt gttgtgcttg gttcccaatt     60

ttgcaagaca tccaagaaaa cttgtttaac ggtggtcaat gtggtgctga agctcatgaa    120

tccttgcgtt tggtttttca cgatgctatt gctatctccc cagcattgga agctcaaggt    180

aagttcggtg gtggtggtgc tgacggttcc atcatggttt tcgatactat tgaaaccaac    240

ttccacccaa acatcggttt ggacgaaatt gtccgtctgc aaaaaccatt cgttcaaaag    300

cacggtgtca ctcctggtga tttcatcgct ttcgctggtg ctgttggttt gtccaactgt    360

ccaggtgccc cacaaatgaa tttcttcttg ggtagacctg ctccaactaa ggctgctcca    420

gacggtttgg tcaccgaacc attccactct gttgaccaaa ttttggctag aatggctgac    480

gctggggaat tcgatgaatt ggaaactgtt tggttgttgt ccgctcactc tgtcgctgct    540

gctaacgatg ttgacccaac tagaaacggt ttaccattcg actccacccc aggtatcttc    600

gatacccaat tcttcgttaa gactcaattg gctggtacca ctttcccagg ttccggtggt    660

aaccaaggtg aagttatgtc ccccttggcc ggtgaaatgc gtttacaaag tgacttcttg    720

attgctagag acactagaac cgcttgtgaa tggcaatcct ttgttaacaa ccaatctaag    780

ttgacttccg atttccaatt catcttcgct gctttgtcta ccttgggtca tgatatgact    840
```

accatgaccg attgttccga cgttatccca atttccaagc cattgagagg tgactctgct 900
agatttccag ctggtaaatc tatgaaggac gttgaacctg cttgtgctga aactccattc 960
ccaactttgg ctactgctcc aggtccagcc acttccgttg ctagagttcc accaccacca 1020
ggtgct 1026

<210> SEQ ID NO 11
<211> LENGTH: 1071
<212> TYPE: DNA
<213> ORGANISM: Phanerochaete chrysosporium

<400> SEQUENCE: 11
gctgtctgtc cagacggtac cagagtttcc cacgctgctt gttgtgcttt catccctttg 60
gctcaagatt tgcaagaaac cattttccaa aacgaatgtg gtgaagatgc ccatgaagtc 120
atcagattga ctttccacga cgctatcgcc atctcccgtt ctcaaggtcc aaaggctggt 180
ggtggtgctg acggttccat gttattgttc ccaaccgttg aaccaaactt ctccgccaac 240
aacggtattg acgactccgt taacaacttg atcccattca tgcaaaagca caacactatt 300
tctgctgctg atttggtcca atttgctggt gctgttgctt tgtccaactg tccaggtgct 360
ccaagattgg aattcttggc cggtcgtcca aacaagacta ttgctgctgt cgacggtttg 420
atcccagaac cacaagattc tgtcactaag attttacaaa gattcgagga tgctggtggt 480
ttcaccccat tcgaagtcgt cagcttgttg gcttctcatt ctgtcgcccg tgctgacaag 540
gttgaccaaa ccatcgatgc tgctccattc gactccactc cattcacttt cgacacccaa 600
gtctttttgg aagtcttatt gaagggtgtc ggtttcccag gttccgctaa caacaccggt 660
gaagttgctt ctccattgcc attgggttcc ggttctgata ccggtgaaat gcgtttgcaa 720
tccgatttcg ccttggctca cgatccaaga accgcttgta tctggcaagg tttcgtcaac 780
gaacaagctt tcatggccgc ttcttttcgt gctgctatgt ctaagttggc tgttttaggt 840
cacaacagaa actccttgat tgactgctca gacgtcgtcc cagtcccaaa gccagctact 900
ggtcaaccag ctatgttccc agcttctacc ggtccacaag atttggaatt gtcttgtcca 960
tccgaaagat tcccaacctt gaccacccaa ccaggtgctt cccaatcttt gatcgcccac 1020
tgtccagacg gttctatgtc ctgtccaggt gtccaattca acggtccagc t 1071

<210> SEQ ID NO 12
<211> LENGTH: 1074
<212> TYPE: DNA
<213> ORGANISM: Phanerochaete chrysosporium

<400> SEQUENCE: 12
gctgtttgtc cagacggtac tagagtcacc aacgctgctt gctgtgcttt cattccattg 60
gcccaagatt tgcaagaaac tttgttccaa ggtgactgtg gtgaggatgc tcatgaagtt 120
atccgtttga cctttcacga tgctattgct atctctcaat ccttgggtcc acaagccggt 180
ggtggtgccg acggttcgat gttgcacttc ccaaccatcg aacctaactt ctccgccaac 240
aacggtattg acgattccgt caacaacttg ttgccattca tgcagaagca cgacactatt 300
tccgctgccg atcttgtcca attcgccggt gctgttgcct tgtctaactg tccaggtgct 360
ccaagattgg aattcatggc tggtagacca aacaccacca tcccagccgt cgaaggtttg 420
attccagaac cacaagactc cgtcaccaag atcttgcaaa gattcgaaga tgccggtaac 480
ttctccccat tcgaagttgt ctccttgttg gcttctcaca ctgtcgcaag agctgataag 540
gttgatgaaa ctattgacgc cgctccattc gattctaccc cattcacttt tgatacccaa 600

```
gttttcttgg aagtcttgtt gaagggtacc ggtttcccag gttccaacaa caacaccggt    660

gaagtcatgt ccccattgcc attgggttcc ggttctgata ccggtgaaat gagattgcaa    720

tctgacttcg ccttggctag agatgaaaga accgcctgtt tctggcaatc cttcgtcaac    780

gaacaagaat tcatggctgc ttcttttaag gctgccatgg ctaagttggc tattttgggt    840

cattccagat cttccttgat cgattgctct gacgttgtcc cagtcccaaa gccagccgtc    900

aacaagcctg ctactttccc agctaccaaa ggtcctaagg atttggatac cttgacttgt    960

aaggctttga agttcccaac cttaacctct gacccaggtg ctaccgaaac cttgattcca   1020

cactgttcta acggcggtat gtcttgtcca ggtgttcaat tcgatggtcc agcc         1074
```

<210> SEQ ID NO 13
<211> LENGTH: 1071
<212> TYPE: DNA
<213> ORGANISM: Phanerochaete chrysosporium

<400> SEQUENCE: 13

```
gctacttgtc cagacggtac caaggttaac aacgccgctt gttgtgcctt cattccattg     60

gctcaagact tgcaagaaac tatcttccaa aatgattgtg gtgaagatgc ccacgaagtc    120

attagattga ccttccatga tgctattgct atttctcaat ctaagggtcc ctctgccggt    180

ggtggtgctg acggttccat gttgttgttc ccaaccattg aaccaaactt ctctgcaaac    240

aacggtattg acgattccgt caacaacttg atcccattca tgcaaaagca cgacactatt    300

tctgctggtg atatcgtcca attcgctggt gctgtcgcct tgaccaactg cccaggtgct    360

ccacaattgg aattcttggc cggtcgtcca aacaagacta ttccagctat cgatggtttg    420

attccagaac cacaagattc tgtcacctcc atcttagaac gtttcaagga tgccggtaac    480

ttctctccat tcgaagtcgt ttctttgttg gcttcccatt ctgtcgccag agctgacaaa    540

gtcgacgaaa ccattgacgc cgctccattc gatactaccc catttgtttt tgacactcaa    600

atcttcttgg aagtcttgtt gaagggtgtc ggtttcccag gtaccgctaa caacactggt    660

gaagtcgcct ccccattgcc attaacctcc ggttccgaca ctggtgaatt gagattacaa    720

tccgactttg ccttggctag agatgaaaga actgcctgca tttggcaagg tttcgtcaac    780

gaacaagcct tgatggctgc ttctttcaag gccgctatgg ctaagttggc cgttttgggt    840

cacgatagaa acaccttggt cgactgctcc gatgtcgttc cagctccaaa gccagccgtc    900

aacaaaccag cttccttccc agctactacc ggtccacaag acttggaatt gtcctgtaac    960

actaagcctt tcccaagttt gtccgttgat gctggtgctc aacaaacctt gattccacac   1020

tgttccgacg gtgatatgac ctgtcaatcc gtccaattca acggtccagc t            1071
```

<210> SEQ ID NO 14
<211> LENGTH: 1071
<212> TYPE: DNA
<213> ORGANISM: Phanerochaete chrysosporium

<400> SEQUENCE: 14

```
gctgtttgcc cagacggtac cagagtttcc aacgctgctt gttgtgcttt cgttccattg     60

gcccaagact tgcaagaaac tttgtttatg ggtgattgtg gtgaagatgc tcacgaagtc    120

atcagattaa ctttccacga cgctatcgcc atttctcaat ctcaaggtcc agaagctggt    180

ggtggtgctg acggttccat gttgttgttt ccaactatcg aaccaaactt cgaagccaac    240

aacggtattg acgactctgt taacaactta attccattca tgcaaaaaca taacaccatc    300
```

```
tctgctgccg acttggttca attcgctggt gctgttgctt tgtccaactg tccaggtgcc    360

ccaagattgg aattcttagc tggtagacca aacactacta tcccagctgt tgaaggtttg    420

attcctgaac cacaagattc tgttaccaag atcttgcaaa gattcgagga cgccggtaac    480

ttctctccat ttgaagttgt ttccttgttg gcctcccact ctatcgctag agccgacaag    540

gtcgatgaaa ctattgacgc cgctccattc gactccaccc ctttcacctt cgatacccaa    600

gtgttcttag aagttttgct aaagggtact ggttttccag gtaccgctaa caacactggt    660

gaagtcgcct cccctttgcc attgggttcc ggtactgaca ctggtgaaat gagattgcaa    720

tctgacttcg ctttagctcg tgattccaga actgcctgta tctggcaatc tttcgtcaac    780

caacaagaat tcatggccgc ctctttcaag gctgctatgt ccaagttggc tattttaggt    840

cattccagat ctaatttgat cgattgttcc gacgttgtcc cagttccaaa gccagctgtt    900

aacaagcctg ccaccttccc agctactaag ggtccacaag acttggaatt gacttgtact    960

tctgaaaagt ttccaacttt gaccactgac ccaggtgcca ccgaaacctt aatcccacac   1020

tgctctaacg gtggtatgtc ttgcccagct gtccaattcg acggtccagc t            1071
```

```
<210> SEQ ID NO 15
<211> LENGTH: 1062
<212> TYPE: DNA
<213> ORGANISM: Phanerochaete chrysosporium

<400> SEQUENCE: 15

gccgtttgtc cagacggtac ccgtgtctcc cacgccgctt gttgtgcttt cattccatta     60

gctcaagact tgcaagaaac tatcttccaa aatgaatgtg gtgaagatgc tcatgaagtt    120

atcagattga cttttcacga cgctatcgct atttccagat ctcaaggtcc aaaggctggt    180

ggtggcgctg atggttctat gttgttattc ccaaccgtcg aaccaaactt ctccgctaac    240

aacggtatcg acgattccgt taacaacttg attccattta tgcaaaaaca caacaccatt    300

tccgctgctg acttggtcca attcgctggt gccgttgctt tgtccaactg tccaggtgct    360

ccaagattgg aattcttggc cggtagacca aacaagacca ttgctgctgt cgacggtttg    420

atcccagaac cacaagattc tgttactaag attttgcagc gtttcgagga tgctggtggt    480

ttcactccat tcgaagtcgt tagtttgttg gcttcccact ccgttgctag agctgataag    540

gttgaccaaa ccattgacgc tgctccattt gattcagttt ttttggaagt cttgttaaag    600

ggtgttggtt tcccaggttc tgctaacaac actggtgaag tcgcttctcc actaccattg    660

ggctcaggtt ccgacaccgg tgaaatgaga ttgcaatccg acttcgcttt ggctcacgat    720

ccacgtactg cttgtatttg gcaaggtttc gttaacgaac aagcttttat ggctgcctcc    780

tttagagctg ccatgtccaa gttagctgtt ttgggtcaca acagaaacag cttgatcgac    840

tgttccgacg ttgtcccagt cccaaagcca gctactggtc aaccagccat gtttccagct    900

tccaccggtc cacaagattt agaattgtcc tgtccatctg aaagattccc aaccttaacc    960

acccaattaa gatgtactga agctggtgct tcccaatctt tgatcgctca ttgtccagac   1020

ggttccatgt cttgtccagg tgttcaattc aacggtccag cc                      1062
```

```
<210> SEQ ID NO 16
<211> LENGTH: 2265
<212> TYPE: DNA
<213> ORGANISM: Phanerochaete chrysosporium

<400> SEQUENCE: 16

caatccgctt ctcaattcac tgacccaact accggtttcc aattcaccgg tattaccgat     60
```

```
ccagtccacg acgttactta cggtttcgtt ttcccaccat tggccacctc tggtgcccaa    120
tctaccgaat tcatcggtga agtcgttgcc ccaattgctt ccaagtggat cggtattgct    180
ttgggtggtg ctatgaacaa cgatttgtta ctggtcgcct gggctaacgg taaccaaatt    240
gtctcttcta ccagatgggc caccggttac gttcaaccaa ccgcttacac cggtaccgct    300
actttgacca ccttgccaga aaccaccatt aatagtaccc attggaagtg ggtctttaga    360
tgtcaaggtt gtactgaatg gaacaacggt ggtggtatcg acgtcacctc cccaaggtgtt   420
ttggcttggg ctttctctaa cgtcgccgtt gatgacccat ctgacccaca atccaccttc    480
tccgaacata ctgatttcgg tttcttcggt atcgactact ccaccgctca ctcagccaac    540
taccaaaatt acttgaacgg tgactctggt aacccaacca ctacctctac taagccaacc    600
tccacctcct cctccgtcac caccggtcca actgtctccg ccactccata cgattacatt    660
atcgtcggtg ctggtccagg tggtatcatc gctgctgacc gtttgtctga agccggtaag    720
aaggtcttgt tgttggaaag aggtggtcca tctactaagc aaaccggtgg tacctacgtt    780
gctccatggg ctacctcttc cggtttgact aagttcgaca tcccaggttt gttcgaatct    840
ttgttcaccg attctaaccc attctggtgg tgtaaggaca tcactgtctt tgctggttgt    900
ttggtcggtg gtggtacctc cgttaacggt gctttgtact ggtacccaaa cgatggtgac    960
ttctctagct ctgtcggttg gccatcctcc tggaccaacc atgccccata cacctccaag   1020
cttagcagta gattgccatc caccgatcac ccatccactg acggtcaaag atacttggaa   1080
cagtccttta acgttgtctc ccaattgttg aagggtcaag gttacaacca agctaccatt   1140
aacgataacc caaactacaa agaccacgtt ttcggttact ctgccttcga cttcttgaac   1200
ggtaaaagag ccggtccagt cgctacctac ttgcaaactg ctttggctag accaaacttc   1260
accttcaaga ccaacgttat ggttagtaac gtcgttagaa acggttccca aattttaggt   1320
gtccaaacca acgacccaac tttgggtcca aacggtttca ttccagttac cccaaaaggt   1380
agagtcatct tgtctgctgg tgctttcggt acttccagaa ttttgttcca atcaggtatc   1440
ggtccaactg acatgatcca aaccgttcaa tctaacccaa ctgccgctgc tgctttgcca   1500
ccacaaaacc aatggatcaa cttgccagtc ggtatgaacg cccaagacaa cccatccatc   1560
aacttggttt tcacccaccc atccatcgac gcttacgaaa actgggccga cgtttggtct   1620
aacccaagac cagctgacgc cgctcaatac ttggctaacc aatccggtgt ctttgctggt   1680
gcttccccaa agctaaactt ctggagagca tactctggtt ccgacggttt taccagatac   1740
gctcaaggta ccgtccgtcc aggtgctgct tccgtcaact cctccttgcc atacaacgcc   1800
tctcaaattt tcaccattac tgtttacttg tctaccggta tccaatccag aggtcgtatt   1860
ggtatcgacg ctgctttgag aggtactgtc ttgaccccac catggctagt caaccctgtc   1920
gacaagaccg ttttgttgca agccttgcac gacgtcgttt ccaacatcgg ttccattcca   1980
ggtttaacta tgattacccc agatgtcacc caaactttgg aagaatacgt cgacgcttac   2040
gatccagcga ctatgaactc aaaccattgg gtcagttcca ccaccatcgg ttcctctcca   2100
caatccgctg tcgttgactc taatgttaag gttttcggta ctaacaacct attcattgtc   2160
gacgccggta tcattccaca cttgcctacc ggtaacccac aaggtacttt gatgtctgct   2220
gctgaacaag ctgctgctaa gatcttggcc ttagctggtg gtcca                     2265
```

<210> SEQ ID NO 17
<211> LENGTH: 1011
<212> TYPE: DNA

<213> ORGANISM: Phlebia radiata

<400> SEQUENCE: 17

```
gccacatgtc cagatggtac tcaattgatg aacgctgaat gttgtgctct attggctgtt      60
cgtgacgact tacaaaacaa catgttcaac aacgaatgtg gtgacgaagc ccacgaagct     120
ttgagattga ctttccatga cgccattgct atctccccag ctatggaagc taccggtcaa     180
ttcggtggtg gtggtgctga cggttctatc atgatcttct cagacatcga aactaagttc     240
cacccaaaca tcggtttgga tgaagtcgtc gaatccttca gaccatttca acaacgttct     300
ggtatgggtg ttgccgactt catccaattc tccggtgctg ttggtacttc taactgtcca     360
ggtgccccaa ctttgaacgc tttcatcggt agaaaggacg ctacccaagc tgctccagat     420
ggtttagtcc cagaaccatt ccatgacgtc aacaccattt tggctagatt taacgacgct     480
ggtgacttcg acgagttaga aaccgtctgg ttcttaatcg ctcactccgt cgctgctcaa     540
aacgatatcg acccagctgt ctctcacgct ccattcgatt ccaccccatc cgtcatggac     600
ggtcaatttt tcatcgaaac ccaattgcgt ggtgtcgaat tcatcggtag tggtggtatc     660
gaaggtgttg ctgaatctcc agtcaagggt gaattcagat tgatgagtga ccaacaaatc     720
gctagagata acagaaccgc ttgtgaatgg caatcctttg gtactgacca agccaagttg     780
caaaaccgtt tccaattcat cttcgaagct atgggtcaat tgggtaccga cccaaccacc     840
ttgatcgatt gctctgacgt cttgccagtt ccaccacctt tgtccactgt tccacacttc     900
ccagctggta tcaccattaa cgatgttgaa ccagcttgtg ctgaaacccc atttccaacc     960
ttgccaaccg acccaggtcc tgctactgct gttgctgccg ttccaagaga c             1011
```

<210> SEQ ID NO 18
<211> LENGTH: 1101
<212> TYPE: DNA
<213> ORGANISM: Phlebia radiata

<400> SEQUENCE: 18

```
aagaccactt gttccaacgg tgttgtcgtc ccagacgctg tctgttgtga cttcgttcct      60
ttggcctctg ctttgcaatc tgaagtcttg atgggtgatt gcggtgagga tgctcatgaa     120
ttggttagat tgattttcca cgacgctatc gctattagcc aatccatggg tccatctgct     180
ggtggcggtg ccgatggttc aatgttgatt ttcccaaccg ttgaaccagc tttttttccca     240
aacttgggta ttgctgactc tgttaacaac ctaattccat tcttgtctca attcccaacc     300
atctctgctg gtgacttggt ccaattcgct ggggctgtcg ctatttccaa ctgtccaggt     360
gctccacaat tggaattcct tgctggtaga ccaaacgcta ctgctccagc tatcgacggt     420
ttgatcccag aaccacaaga cgatgttacc aagattttgg ctagattcaa ggatgccggt     480
aacttctccc cagctgaggt tgtcgctttg ttggcttccc attctatcgc tagagctgac     540
cacgttgatc caactttgga cgccgctcca ttcgactcta ccccattcga tttcgatacc     600
caaattttct tggaagtttt gttgaagggt gtcggtttcc caggtttagc caacaacact     660
ggtgaagtta gctccccatt gccagtcacc gatggtaccg atgttggtga attgcgtttg     720
caatctgact tcgctttggc tagagatgaa agaactgctt gtgcttggca atccttcgtc     780
aacgaacaag aagctatggc taccgctttc aagaacgctg ttaagaagtt ggccgttttg     840
ggtcacaaca gaaacgattt ggttgactgt tctgctgtcg tcccagttcc aaagccagct     900
accggtactc cagctacctt ccctgcttcc accggtccac aggatttgga attgacctgt     960
actaccgaac cattccctac cttgtctact gctcctggtg ctcaacaaac cttgattcca    1020
```

cactgttctg acggtaccat gacttgtaac tctgtccaat tcgatggtcc agctaccaac 1080
ttcggtggtg ccgacgattc a 1101

<210> SEQ ID NO 19
<211> LENGTH: 1017
<212> TYPE: DNA
<213> ORGANISM: Phlebia radiata

<400> SEQUENCE: 19
gtcgcttgtc cagatggtgt caacactgcc accaacgctg tttgctgttc tttgttcgct 60
gtcagagatt tgatccaaga ccaattgttc gatggtggtg aatgtggtga agaagttcac 120
gaatccttga gacttacttt ccacgacgcc attggtatct ctccaaccat cgcttctact 180
ggtgttttcg gtggtggtgg tgctgacggt tccatcgcta ttttcgctga aatcgaaacc 240
aacttccacg ccaacaacgg tgtcgatgaa atcatcggtg aacaagcacc attcatccaa 300
atgaccaaca tgactactgc tgacttcatc caatttgctg gtgctgttgg tgtttctaac 360
tgtccaggtg ctccagcctt gcctgttttc gttggtagac cagacgctac tcaaccagcc 420
cctgacaaga ctgtcccaga accattcgac accgttgact ccatcttggc cagattcgct 480
gatgccggtg gtttctcttc cgctgaagtc gtcgctttgt tggcctctca cactattgcc 540
gctgctgacc acgtcgatcc atctattcct ggtaccccat tcgacagcac cccagaaatc 600
ttcgatactc aattcttcat tgaaacccaa ctacgtggta tcttgttccc aggtaccggt 660
ggtaaccaag gtgaagtcga atccccatta cacggtgaaa ttagattgca atccgactcc 720
gaattggcta gagattctag aactgcctgt gaatggcaaa gcttcgtcaa caaccaagct 780
aagatccaat ccgccttcaa ggccgctttc agaaaaatga ctatcttagg tcactctgaa 840
tcctctttga tcgaatgttc tgaagtcatc caaactccac cagccttgga aggtaacgct 900
cacttgccag ccggtcaaac tatgaacgac atcgaacaag cctgcgctac taccccattc 960
ccatctttgt ccgctgatcc aggcccagct acctctgtcg cccctgtccc accatct 1017

<210> SEQ ID NO 20
<211> LENGTH: 1503
<212> TYPE: DNA
<213> ORGANISM: Phlebia radiata

<400> SEQUENCE: 20
actaactctg gtattggtcc agttaccgac ttgagaatct ccaacgccgt tgtctctcca 60
gacggttttt ctcgtgacgc cgtcgttgtc caaggtcaat tcccatcccc attaatcaag 120
ggtaacaagg gtgacatgtt taagttgaac gtcattaacc aattacaaga tactgcctta 180
aacacttcta cttccatcca ctggcatggt ttgttccaac acggtaccaa ctgggctgac 240
ggtccagctt tcgtgactca atgtccaatc gtcaccggtg attccttcgt ttacgacttc 300
actgttccag accaagctgg taccttctgg taccactccc acttggcttt acaatactgt 360
gatggtttga gaggtccatt ggtcgtttac gacccacacg atccatacgc tcacttatac 420
gacgtcgatg acgaatctac tgttattact ttagccgaat ggtaccacac tgctgccgac 480
aacttacgtc caccagaaga agctaactcc actttgatca acggtttagg tagatacgct 540
ggtggtccag cctctccatt gtccgttatc actgttgaac acggtaagag atacagattc 600
agactggtta gtatggcttg tgacccttcc tacaacttca ctatcgacgg tcacaacatg 660
accgttattg aagtcgacgg tgtcaaccac ttgccattga ctgttgacaa gatccaaatt 720
tttgttgctc aaagatactc tttcatcttg gatgctaacc aaccaattgg taactactgg 780
atccatgcta tcccaaacgg tcaatctcaa ttggttggtg tcgctaacgg tatcaactcc 840
gccatcttga gatacgttgg tgctccaaac aaggaaccaa ctactcaaac cccaccatcc 900
gttgccccat tgcaagaagt caacttacac ccattggtta acgctgccgc tcctggtaag 960
ccattcccag gtggtgctga ccaagtcatc ccattcaact tgtctttgtt gggtgctaac 1020
ttcttgatca acaacgctac tttctcccct ccaaccgttc cagttttgtt gcaaatcttg 1080
tctggtgcta agactcctca acaattgttg ccaccaggtt ctatctactc cttgaagaga 1140
aactctgtta ttgaaatcgt cattccacca ggtaccgctc caggtggtcc acaccctttc 1200
cacttgcacg gtcacacttt ctctgtcgtt agatccgctg gttcttctgt ttacaacttt 1260
aagaacccag ttcaacgcga cgttgtttcc atcggtactg gtgctaacga ttccgttacc 1320
atcagattcg ttactgacaa cccaggtcca tggttcatcc actgtcacat cgacttccac 1380
ttgaacgctg gtttggctgc tgttatggct gaggacattc cagacattaa gttggctaac 1440
cctgttccag ccgaatggga acaattgtgt ccaatttacg accaaaaggt cttgcatgaa 1500
cac 1503

<210> SEQ ID NO 21
<211> LENGTH: 993
<212> TYPE: DNA
<213> ORGANISM: Pleurotus eryngii

<400> SEQUENCE: 21
gccacttgtg ctgacggtag aaccactgct aacgctgcct gttgcgtctt gttcccaatc 60
ttggatgata ttcaagaaaa cttgttcgac ggtgctcaat gtggtgaaga agtccacgaa 120
tccttgagat tgactttcca cgacgccatc ggtttctctc caaccttagg tggtggtggt 180
gctgatggtt ccattatcgc cttcgatact atcgaaacca acttcccagc taacgctggt 240
attgacgaaa ttgtttcagc tcaaaagcca ttcgttgcta agcataacat ttccgctggt 300
gatttcatcc aattcgccgg tgctgttggt gtttccaact gtcctggtgg tgttagaatt 360
ccattcttct tgggtagacc agatgccgtt gctgcctccc cagatcactt ggtcccagaa 420
ccattcgact ccgttgattc tatcttggct agaatgtctg acgccggttt cagcccagtc 480
gaggttgtct ggttattggc ttctcactcc attgctgctg ctgataaggt cgacccatct 540
attccaggta ctccattcga tagtactcct ggtgttttcg actctcaatt cttcatcgaa 600
acccaattaa agggtagatt gttcccaggt actgctgata acaagggtga agctcaatcc 660
ccattgcaag gtgagattcg acttcaaagc gaccacttgt tggctagaga tccacaaacc 720
gcctgtgaat ggcaatccat ggtcaacaac caaccaaaga ttcaaaacag attcgctgct 780
actatgtcca agatggcctt gttgggtcaa gacaagacca agttaattga ttgctccgat 840
gttattccaa ctccaccagc tttggtcggt gccgctcact taccagccgg tttcagtttg 900
tccgacgttg aacaagcttg tgctgctacc ccattcccag ctttaactgc tgacccaggt 960
ccagttactt ccgttccacc agtcccaggt tct 993

<210> SEQ ID NO 22
<211> LENGTH: 993
<212> TYPE: DNA
<213> ORGANISM: Pleurotus eryngii

<400> SEQUENCE: 22
gctacttgtg acgatggtag aaccactgcc aacgccgctt gttgtatctt gttcccaatt 60

-continued ttagacgaca ttcaagaaaa cctattcgac ggtgctcaat gtggcgaaga agtccatgaa 120
tctttgagat tgaccttcca cgatgctatt ggtttcagcc caactttggg tggtggtggt 180
gctgatggtt ctatcattgc tttcgacact atcgaaacta acttcccagc taacgccggt 240
atcgatgaaa ttgtctctgc tcaaaagcca ttcgtcgcta agcataacat ctccgctggt 300
gacttcatcc aatttgctgg tgctgttggt gtctctaact gtccaggtgg tgtcagaatc 360
cctttcttcc taggtagacc agacgctgtc gctgcttctc cagaccactt agttccagaa 420
ccattcgact ccgtcgactc tattttggct agaatgggtg acgctggttt ctctccagtt 480
gaagttgtct ggttgttggc ttctcacagt attgctgctg ctgataaggt cgacccatct 540
attccaggta ctccattcga ctctacccca ggtgttttcg attcccaatt cttcatcgaa 600
actcagttaa agggtagatt gttcccaggt accgctgaca acaagggtga agctcaatct 660
cctttacaag gtgaaattag attgcaatct gatcacttgt tggctcgtga tcctcaaact 720
gcctgtgaat ggcaaagcat ggtcaacaac caaccaaaaa tccaaaacag attcgctgct 780
accatgtcca agatggcctt gttgggtcaa gacaaaacca agttgattga ttgctctgac 840
gttatcccaa ctccaccagc tttggtcggt gcagctcact tgccagctgg tttctccttg 900
agcgatgttg aacaagcttg tgctgctacc ccattcccag ctttgactgc tgacccaggt 960
ccagtcacta gcgttccacc agttccaggt tcc 993

<210> SEQ ID NO 23
<211> LENGTH: 1539
<212> TYPE: DNA
<213> ORGANISM: Pleurotus eryngii

<400> SEQUENCE: 23
tctattggtc caagaggtac cttgaacatc gctaacgaag ttattaagcc agatggtttc 60
agcagatccg ctgtcttggc cggtggtagt tacccaggtc cattgatcaa gggtgaaact 120
ggtgacagat tccaaattaa cgtcgtcaac aagttggctg acacttcaat gcctgtcgat 180
acttctatcc attggcacgg tatttttgtt agaggtcaca actgggccga cggtccagct 240
atggtcaccc aatgtccaat cgtcccaggt cactccttct tgtacgactt tgaaattcca 300
gatcaagccg gtactttctg gtaccactct cacttgggta cccaatactg tgacggtttg 360
agaggtccat tcgttgtcta ctccaagaac gacccacaca aaagattgta cgatgtcgac 420
gacgaatcta ctgtcctaac cgttggtgac tggtatcacg ctccttcttt gtccttgtct 480
ggtgtcccac acccagactc cactttgttc aacggtttgg gtagatcctt gaacggtcca 540
gcctccccat tatacgtcat gaacgttgtc aagggtaaga gatacagaat cagattgatt 600
aacacttctt gtgattctaa ttaccaattt tccattgacg gtcacgcttt cactgtcatc 660
gaagctgatg gtgaaaacac ccaaccattg caagtcgacc aagtccaaat cttcgctggt 720
caacgttact ccttggtttt gaacgctaac caagctgttg gtaactactg gatcagagct 780
aacccaaact ctggtgatcc aggtttcgct aaccaaatga actccgctat cttgagatac 840
aagggcgcta gaaacgttga ccctactacc ccagaaagaa acgctactaa cccattgaga 900
gaatacaact tgcgtccatt gatcaaggaa ccagctccag gtaaaccatt cccaggtggt 960
gctgatcaca acatcaacct aaactttgcc ttcgacccag ctaccgtttt attcactgct 1020
aacaactata cctttgtccc acctactgtt ccagttctgt tgcaaatttt gtctggtact 1080
cgtgatgccc atgatttggc tccagctggt agtatctacg acatcaagtt gggtgacgtc 1140

```
gttgaagtta ctatgccagc cttggttttc gctggtccac acccaatgca tttgcacggc   1200

cactcctttg ccgtcgttcg ttctgctggt tcctccacct acaactacga aaacccagtc   1260

agacgtgatg ttgtttcaat tggtgacgat ccaactgata acgttactat cagattcgtc   1320

gctgacaacg ctggtccatg gttcttgcac tgtcacatcg actggcactt ggacttgggt   1380

tttgctgtcg tctttgctga aggtgttaac caaaccgctg tcgctaaccc agtccctgaa   1440

gcttggaacg atctttgtcc aatctacaac tcttccaacc catccaaatt gttgatgggt   1500

actaacgcta ttggtagatt gcacgcccca ttgaaggct                          1539
```

<210> SEQ ID NO 24
<211> LENGTH: 1698
<212> TYPE: DNA
<213> ORGANISM: Pleurotus eryngii

<400> SEQUENCE: 24

```
gccgacttcg attacgttgt cgtcggtgct ggtaacgccg gtaacgttgt cgctgccaga     60

ctaaccgagg acccagatgt ctctgtcttg gttttagaag ctggtgtttc tgacgaaaac    120

gttttgggtg ctgaagctcc attgttggcc ccaggtttag tcccaaactc tatcttcgat    180

tggaactaca ctaccaccgc tcaagctggt tacaacggtc gttccattgc ttacccaaga    240

ggtagaatgt tgggtggttc ttcctctgtc cactacatgg ttatgatgag aggttctacc    300

gaggatttcg atagatacgc cgctgtcacc ggtgatgaag gttggaactg ggacaacatc    360

caacaattcg ttagaaagaa cgaaatggtc gttccaccag ctgacaacca caacacttcc    420

ggtgaattca ttcccgctgt tcacggtact aacggttctg tctccatctc tttgccaggt    480

tttcctaccc cattggatga cagagttttg gccaccaccc aagaacaatc cgaagaattc    540

ttcttcaacc cagatatggg tactgggcat cctttgggta tctcatggtc cattgcttct    600

gtcggtaacg gtcaaagatc ctcctcttct accgcctact tgcgtccagc ccaatccaga    660

ccaaacttgt ccgttttgat caacgcccaa gtcaccaagt tggtcaactc cggtactacc    720

aacggtttgc ctgcttttag atgtgtcgaa tacgccgaac aagaaggtgc tccaactacc    780

actgtctgtg ctaagaagga agtcgttttg tctgctggtt ccgtcggtac cccaatcttg    840

ttgcaattgt caggtatcgg tgatgaaaac gacttgtcaa gtgtcggtat tgacaccatc    900

gtcaacaacc catctgttgg tagaaacttg tctgaccact tgttgttgcc agccgctttc    960

ttcgtcaact ccaaccaaac tttcgataac atttttcgtg actcttctga attcaacgtc   1020

gacttggacc aatggaccaa caccagaacc ggtccattga ctgctttgat cgctaaccac   1080

ttggcttggt tgagattgcc ttccaactct agtatcttcc aaactttccc agatccagcc   1140

gctggtccaa actccgctca ctgggaaacc atcttctcta accaatggtt ccacccagct   1200

atcccaagac cagacactgg ttccttcatg agcgttacca acgctttgat ctccccagtc   1260

gctagaggtg acatcaagtt ggccacctct aacccattcg ataagccatt gattaaccca   1320

caatacttgt ctactgaatt cgacattttt accatgattc aagctgttaa gtctaacttg   1380

agattcttgt ctggtcaagc ctgggctgat ttcgtcatca gaccattcga cccaagattg   1440

cgtgacccaa ctgacgatgc cgccatcgaa tcctacatta gagataacgc taacaccatt   1500

ttccacccag tcggtactgc ttctatgtct ccacgtggtg cttcttgggg tgtcgtcgat   1560

ccagacttga aggtcaaggg tgtcgacggt ttgagaattg ttgacggttc cattttgcca   1620

ttcgctccaa acgctcacac ccaaggtcca atctacttgg tcggtaagca aggtgccgat   1680

ttgatcaagg ctgatcaa                                                 1698
```

<210> SEQ ID NO 25
<211> LENGTH: 1092
<212> TYPE: DNA
<213> ORGANISM: Ceriporiopsis subvermispora

<400> SEQUENCE: 25

```
gtcacctgtt ccgacggtac cgtcgtccct gactctatgt gttgtgactt cattccattg     60
gcccaagact tgcaatccat ggtcttgcaa aacgaatgtg gtgaagatgc tcacgaaatc    120
atcagattga ctttccacga cgccatcgct atctctcaat ccttgcctcc atccgccggt    180
actggtgctg atggttccat gttgttgttc cctttggtcg aaccagaatt ccaagcctct    240
aacggtatcg acgattctgt taacaacttg atcccattct tgtccagcca cccaaacatt    300
actgctggtg acttggtcca attcgctggt gctgttgcct tgactaactg tccaggtgct    360
ccaagagaat tgttggctgg tagaaagaat gctgtcgctc cagctatcga cggtttgatt    420
cctgttccac aagataatgt tagtactatc ctagctagat tcgctgacgc cggtaacttt    480
tctccattcg aagttgtctc cttgttggcc tctcactctg tcgctagagc cgataaggtt    540
gacccaactt tggacgctgc cccatttgat actactccat ttactttcga cacccaaatc    600
tttttggaag tcttgttgaa gggtgttggt tttccaggtt tggacaacaa caccggtgaa    660
gtcgcctccc cattgccctt cggtgacact tccaccggtg gtaacgacac tggtatgatg    720
agattgcaat ccgactttgc tttggctaga gatgaacgta ccgcttgttt ctggcaaggt    780
ttcgtcgacc aacaagactt catggctcaa tctttccaag ctgctttcga aaagatggcc    840
atcttaggtt ccaacgctgc cgatttgatc aactgttctg ctgtcgttcc acaatctgtc    900
ggtccagtta ctgttccagc tactttccca gctaccactg gtccccaaga cttacaattg    960
aattgtacct ccgaaacctt cccatctttg tccattgacc caggtgctac cgaaactttg   1020
attccacact gtccagatgg tactgaagat tgtccatcct tgcaattctc tggtcctgcc   1080
actgactctc ca                                                       1092
```

<210> SEQ ID NO 26
<211> LENGTH: 1098
<212> TYPE: DNA
<213> ORGANISM: Ceriporiopsis subvermispora

<400> SEQUENCE: 26

```
accatttgtc cagatggtac tagagtctcc aaccacgttt gttgtgattt catcccattg     60
gctcaagcct tacaatccac tttgtacatg ggtgactgtg gtgaggatgc ccatgaaact    120
attagattga ctttccacga cgccatcgct atttctcaat cccaaggtcc atctgctggt    180
ggtggtgctg atggttccat gttcattttc ccaactgtcg aaccattctt ccacgctaac    240
gcaggtattg atgactccgt caacaacttg attccattct tgtctaagtt cccaaccatt    300
accgctggtg acttaatcca attcgctggt actgtcgctt tgtctaattg tccaggtgct    360
ccacaattgg aatttttggc tggtagacct aacgccaccg ctcctgccgt tgacggtttg    420
attccagaac cacaagacaa cgttactcat atcttggaaa gattcgctga tgctggtggt    480
ttcactccat tcgaagtcgt ttctttgttg gcttctcaca ccgtcgctag agctgacaag    540
gtcgacttga ccattgatgc tgctccattc gactccactc cattcacctt cgacactcaa    600
atcttcctag aagttttgtt gaagggtgtc ggtttcccag gtaccgacaa caacactggt    660
gaagttgaat ctccattgcc attgggtaac aacaagcaag gtggtaacga caccggtgaa    720
```

```
atgagattgc aatctgactt cgctttggcc cgtgacgaca gaaccgcatg tttctggcaa    780

ggtttcgtca acgaacaaga atacatgatg tccagcttca aagccgccat gtccaagttg    840

gctatcttgg gtcataacag aaacgacttg attgactgtt ctgaagttgt cccaactcct    900

aagccaccag tcggtaagcc agccactttc ccagctacca ctggtccaca agacttgcaa    960

ttgacttgta agtctgaaag attcccatcc ttgaccattg accacggtgc tagagaaacc   1020

ttgatcccac actgttccaa cgggggtcaa gactgtccaa ctgttcaatt caccggtcca   1080

gctggtgagg acgactct                                                 1098
```

<210> SEQ ID NO 27
<211> LENGTH: 1098
<212> TYPE: DNA
<213> ORGANISM: Ceriporiopsis subvermispora

<400> SEQUENCE: 27

```
accatttgtc ctgatggtac cagagtctct aaccacgttt gttgcgactt catccctttg     60

gctcaagctt tgcaatccac tttgtacatg ggtgactgtg gtgaagatgc ccacgaaact    120

attagattga ccttccacga cgctattgct atttcccaat ctcaaggtcc atctgccggt    180

ggtggtgctg atggttccat gttgattttc ccaactgtcg aaccattctt ccacgctaac    240

gctggtattg acgactctgt caacaacttg atcccattct tggataagtt cccaaccatt    300

actgctggtg acttgattca attcgccggt actgtcgcct tgtccaactg tccaggtgcc    360

ccacaattgg aatttttggc tggtcgtcca aacgctaccg ctccagctgt tgacggtttg    420

attccagaac cacaagataa cgtcactcac atcttggaaa gattcgctga cgccggtggt    480

ttcactccat tcgaagtcgt tagtttattg gcttctcaca ccgtcgccag agctgataaa    540

gttgacttga ctattgacgc tgctccattc gactctactc catttacttt cgacacccaa    600

atcttcttgg aagtcttgtt gaagggtgtt ggtttcccag gtaccgacaa caacactggt    660

gaagtcgaat ctccattgcc cttgggtaac aacaagcaag gtggtaacga aactggtgaa    720

atgagattgc aatccgactt cgccttggct cgtgatgaca gaactgcttg tttctggcaa    780

ggtttcgtca acgaacaaga atacatgatg tcatcattca aggctgctat gtccaagttg    840

gccattttgg gtcacaacag aaacgacttg atcgactgtt ctgaagttgt cccaacccca    900

aagccaccag ttggtaagcc agcttccttc ccagctacta ctggtccaca agacctacaa    960

ttaacttgta agtccgaaag attcccatct ttgaccattg accacggtgc ccaagaaacc   1020

ttgatcccac attgttccaa cggtggtcaa gattgtccaa ccgttcaatt cacgggtcca   1080

gctggtgaag atgactct                                                 1098
```

<210> SEQ ID NO 28
<211> LENGTH: 1095
<212> TYPE: DNA
<213> ORGANISM: Ceriporiopsis subvermispora

<400> SEQUENCE: 28

```
gttacctgct ctgatggtac tgctgttcca gacgctatgt gttgtgattt cattccattg     60

gctcaagatc tacaatcaat ggttttacag aatcaatgcg gtgaagatgc tcacgaaatc    120

attagattaa ccttccatga cgccattgct atctcccaat ccttgggtcc atccgccggt    180

accggtgccg atggttctat gttgttgttc ccattggtcg aaccagaatt cgctgcctcc    240

aacggtattg acgattccgt taacaactta atcccattct tgtcctctca cccaaacatt    300

tcagccggtg acttggtcca attcgctggt gctgttgctt tgactaactg cccaggtgcc    360
```

ccaagagtca acttcttggc tggtagaaag aacgctgttg ctccagctat cgatggttta 420
atcccagaac cacaagacaa cgtcacctct atcttggcta gattcgccga tgctggtaac 480
ttctccccat tcgaagttgt ctccttgttg gcttctcact ccgttgctag agctgacaag 540
gttgacccaa ccttagacgc tgctccattc gattccactc cattcacctt cgatacccaa 600
gttttcctag aagtcttgtt gaagggtgtt ggtttcccag gtactgacaa caatactggt 660
gaagtcgcct ccccattgcc attcggtgat acttccaccg gtgtcaacga tactggtatg 720
atgagattgc aatctgactt cgccttggct cgtgacgaaa gaactgcttg tttctggcaa 780
tccttcgttg atcaacagga cttaatggcc caaagtttcc aagctgcttt cgaaaagttg 840
gctatcttgg gttcctccgc agctgatttg gttaactgtt ccgctgtcgt tccattgtcc 900
gttggtccag tcaccgcccc agctaccttc cctgctacta ccggtccaca agacttgcaa 960
ttaacctgta ccactgaaac cttcccatcc ttatctattg atccaggtgc taccgaaacc 1020
ttgatcccac actgtccaga tggttccgaa gattgtccaa ctgtccaatt ctctggccca 1080
gctaccgact ctcca 1095

<210> SEQ ID NO 29
<211> LENGTH: 1068
<212> TYPE: DNA
<213> ORGANISM: Ceriporiopsis subvermispora

<400> SEQUENCE: 29
gccgtctgtg ctgacggtac cagagtttcc aacgctgctt gttgtgcctt cattccattg 60
gctcaagact tgcacgaaac cttgttcatg ggtgattgtg gtgaagatgc tcatgaagtc 120
atccgtttaa ctttccacga cgctgttgcc atttcctcct ctatgggtcc atccgccggt 180
ggtggtgccg atggttctat gttgttgttc ccaaccgtcg aaccaaactt ctctgctaac 240
aacggtatcg acgattccgt caacaactta atcccattct tgtccaagca cgctgtctct 300
gctggtgacc tagtccaatt cgctggtgct gtcgccttga ccaactgtcc aggtgctcca 360
caattggaat tcttggctgg tagaccaaac cacaccattg ctgctatcga cggtttgatc 420
ccagaaccac aagatgacgt caccaagatt ttggctagat tcgaagatgc cggtggtttt 480
tccccattcg aagttgttag tttgttggct tctcataccg ttgccagagc tgacaaggtt 540
gatggtacta tcgatgccgc tcctttcgac tctactccat tcactttcga tacccaagtt 600
tttttagaag tcttgttgaa gggtaccggt ttcccaggta ctaacaacaa cactggtgaa 660
gttgcttccc cattgccatt gacgtccggt aacgacactg gtgaaatgcg tctgcagagt 720
gatttcgcct tggctagaga tgaaagaacc gcttgtttct ggcaatcttt cgtcaacgaa 780
caagaattca tggctcaatc cttcaaggct gctatgtcca agttggccgt tttgggtcac 840
tcaagatcct ctttggtcga ctgttctgat gttgtcccag ctccaaagcc agccgttaac 900
aagccagcta ctttcccagc tactaccggt ccagatgatt tggaattgac ttgcaccgcc 960
gaaagattcc caaccttgtc cgtcgaccca ggtgctcaac aaactttgat cccacactgt 1020
tccgatggtg atcaagtttg tgccaccgtc caattcactg gtccagct 1068

<210> SEQ ID NO 30
<211> LENGTH: 1068
<212> TYPE: DNA
<213> ORGANISM: Ceriporiopsis subvermispora

<400> SEQUENCE: 30

```
gctgtttgtt ctgacggtac ccgtgtctcc aactctgctt gttgtgcctt tatcccattg     60
gctcaagatt tgcaagaaac tttgttcatg aacgactgtg gtgaagatgc tcacgaagtc    120
atcagattga ctttccacga cgctgttgcc atttctcgtt cccaaggtcc atccgccggt    180
ggtggtgctg atggttccat gctattgttc ccaaccgttg aaccaaactt ctccgccaac    240
aacggtattg acgattctgt caacaatttg atcccatttt tggctaagca ccctgtttcc    300
gctggtgacc tagtccaatt cgctggtgct attgctttga ctaactgtcc aggtgctcca    360
caattggaat tcttggctgg tagaccaaac cacaccattg ctgctgttga cggtttgatc    420
ccagaaccac aagacgatgt cactaagatc ttggctagat tcgacgacgc tggtggtttc    480
tctccattcg aagttgttag cttgttggct tcccataccg ttgctagagc tgataaggtc    540
gacgaaacta ttgacgctgc tccattcgac tctactccat tcactttcga tacccaagtt    600
ttcttggaag ttttgttgaa gggtgtcggt ttcccaggta ctgacaacaa caccggtgaa    660
gtcgcttccc cattgccatt gacttcaggt aacgacactg gtgaaatgag attgcaatct    720
gacttcgctt tggctagaga ttccagaact gcttgtttct ggcaaggttt tgttaacgaa    780
caagaattca tggctcaatc tttcaaagct gctatgtcca agttggctgt cttgggtcat    840
tctagatcag atttgatcga ctgttccgat gttattccaa ccccaaaacc agctgtcaac    900
aagccagcta ctttcccagc ctctaccggt ccaaaggact tggaattgtc ctgtttcgct    960
gaaagattcc caactctacc agtcacccct ggtgctactc aaactttgat cccacactgt   1020
tccaacggtg gtgaagattg tccaacggtt caattcactg gtccagcc               1068
```

<210> SEQ ID NO 31
<211> LENGTH: 1071
<212> TYPE: DNA
<213> ORGANISM: Ceriporiopsis subvermispora

<400> SEQUENCE: 31

```
accatctgtc cagacggtac cagagtttcc aaccacgcct gttgtgcttt cattccattg     60
gctgaggatt tgcaaaagac tatcttcatg aacgactgtg gtgaggatgc tcacgaagtc    120
attagattga ccttccacga cgctgtcgct atttctagaa aattgggtcc aaaggctggt    180
ggtggtgctg acggttctat gttgttgttc ccaaccgttg aaccaaactt ctccgctaac    240
aacggtatcg atgactctgt taacaacttg attccattca tggctagaca cccaacagtt    300
agcgctggtg acttggttca attcgctggt gccgttgctc tttctaactg tccaggtgct    360
cctcgtttgg aattcttggc tggtagacca aaccatacta tcgctgctat tgatggtttg    420
attccagaac cacaagatga cgtcactaag atcttggaaa gatttgatga tgctggtggt    480
ttcaccccat tcgaagttgt ctccttgttg gcttcccaca ccgttgccag agctgacaag    540
gtcgatgaaa ccatcgatgc tgctccattc gactccaccc ctttcacttt cgacacccaa    600
gtctttttgg aagtcttgtt aaagggtgtc ggcttccctg gtaccgataa caacactggt    660
gaagttgctt ccccattgcc aaaaggttcc ggtaacgata ccggtgaaat gagattacaa    720
tctgacttcg ctttggctag agatccaaga accgcttgtt tctggcaagg tttcgtcgac    780
gaacaagaat tcatggctga atctttcaag gccgctatgg ccaagttggc tattttgggc    840
cacaacagag cctccttgac cgactgttcc gatgttgtcc caattccaag accagctgtc    900
aaaaagcctg cctccttccc agctactacc ggtccaaagg acttggaatt gacttgtaga    960
gctgaaagat tcccaacttt gaccgttgat agaggtgctg tccaagcttt gatcccacac   1020
tgttccaacg gtggtcaaga ttgtccatcc gttcaattcg acggtccagc c            1071
```

<210> SEQ ID NO 32
<211> LENGTH: 1014
<212> TYPE: DNA
<213> ORGANISM: Ceriporiopsis subvermispora

<400> SEQUENCE: 32

```
gtcacttgcc cagacggttc catgaccgct aacgaagcct gttgtgtctt gttcccagtc     60
ttggaagata ttcaacaaaa cttattcgat ggtggtttgt gtggtgaaga agcccatgaa    120
tctttgagat tgactttcca cgacgctttc ggtttctccc cagccttgca agctcaaggt    180
caattcggtg gtggtggtgc tgatggttct gtcattgttt ttgaagaaac tgaagctaac    240
tttgctgcta acatcggtat cgacgaaatc attaatgccc aaaagccatt catcgctaga    300
cacaacatta ccccaggtga cttcgtccaa ttcgccggtg ctgtcggtgc tgccaattgt    360
ccaggtgctc cacaattgca attcatgttg ggtagaccaa tgccagtcgc ttcttctcca    420
gatggtttaa tccctgaacc attcgacact gttgattcta tcattgaaag attcgccgac    480
gctggtaact tcactgaaac cgaaattatc tggttgttga ctgctcactc cattgctgct    540
gctgacgaag ttgatccaac tatcccaggt actccattcg actctacccc aggtattttc    600
gacagccaaa tcttcattga agtccaattg agaggtacct ctttcccagg tactggtggt    660
aaccaaggtg aagttgaatc ccattgaga ggtgaattga gattgcaatc tgactccgaa     720
ttggctagag atagccgtac tgcttgtgaa tggcaagcct tcgtcgacaa cgtcccaaga    780
atgcaaactt tgttctctgc tgccatgtct accttggctg ttattggtca agacacttcc    840
caaatggtcg actgttctga tgttatccca gtcccaccac caccacaagg tactgcccat    900
attccagctg gtttgtctaa cgctgatatt gaacaagcct gtgctaccgc cgctttccca    960
tctttgccag tcgacccagg tccagctact tccgtcgccc cagttccacc agca         1014
```

<210> SEQ ID NO 33
<211> LENGTH: 1014
<212> TYPE: DNA
<213> ORGANISM: Ceriporiopsis subvermispora

<400> SEQUENCE: 33

```
gccacttgtc cagacggtaa caccgtcacc aacgaagcct gttgtttctt gttcccaatc     60
ttggaagata tccaagctaa cctgttcaac ggtggtgaat gtggttccga agctcacgaa    120
tctttgagat tgactttcca tgacgctatt ggtttctctc cagctttgac cgctcaaggt    180
caattcggtg gtggtggtgc tgatggttcc gttatcacct tcgcttctat cgaaactgct    240
tacgccgcta acgctggtat cgaggatatt gttgctgaac aagctcaatt cgtcgccaag    300
tacaatgtta gtgctggtga ctttgttcaa ttcgctggtg ctgtcggttt gtctaactgc    360
ccaggtgctc cacaattgga cttcgttatc ggtcgtccag ctgctactgc tgcttcccca    420
gacggtttgg ttccagaacc attcgacaac gtcacctcta tcttggctag attcaacgac    480
gctggtggtt tcgacccaca acacgttgtc tggttgctta gctcacactc cgtcgctgct    540
gctgaattgg ttgacccatc catcccaggc gctccattcg attctacccc aggtttgttc    600
gacactcaat tttcattga aacccaattg actggtacct tgtggccagg taccgctaac     660
aaccaaggtg aagtcgaatc cccattgcta ggtgagattc gtttgcaatc agacttctta    720
ttggctagag acaacagaac cgcttgtgaa tggcaatcct ttgctaacga cttgtctaga    780
caacaaactt tgttcaaggc cgctatgtcc actttggcta ccatcggtca agacacctcc    840
```

```
accttgactg attgttccga cgttatccca gttccagctg ctccagttgg tactccacac    900

ttcccagctg gtttgaccaa cgctgacgtt gaccaagcct gtaccactgc tgcttttcca    960

accttgtcca ccgacccagg tccagctact tccgttgctc cagtccctac tgca         1014


<210> SEQ ID NO 34
<211> LENGTH: 1494
<212> TYPE: DNA
<213> ORGANISM: Ceriporiopsis subvermispora

<400> SEQUENCE: 34

gccatcggtc cagttaccga tttggaaatt actgacgctt ttgtttcacc tgacggtcca     60

ggtttgggta gagaagctgt tttggccggt ggtacctttc caggtccctt aatccaaggt    120

aacaagggtg ataacttcca aatcaacgtt gtcaacaact tgaccaacca caccatgttg    180

aaaaccacct ccattcactg gcacggtttg tttcaacacg gtactacctg ggccgacggt    240

cctgctttcg tttctcaatg tccaattgct tctggtaact ccttcttgta caacttcaac    300

gtcccagatc aagccggtac cttctggtac cattctcact tggctactca atactgtgac    360

ggcttgagag gtcctttggt tgtctacgac ccaaacgacc cacacgctga cttgtacgat    420

gttgacgatg aatccaccgt catcaccttg tccgactggt accacgccgc cgcttctacc    480

ttgactttcc caacctttga taccacccta attaacggtt tgggtagatt cgctggtacc    540

ggtggtagtg actctaactt gaccgttatc actgtcgaac aaggtaagag atacagattc    600

agattagttt ctatttcttg tgatccaaac tgggtcttta gtatcgatca acacgaattg    660

accgttattg aagttgacgg tgttaacgcc gttcctttga ccgtcgatgc tattcaaatc    720

ttcgccgctc aaagatactc cttcgttttg aacgccaacc aaactgttga taactactgg    780

atcagagcta acccaaataa cggtaacatg ggtttcgcta acggtatcaa ctctgctatc    840

ttgagatacg ttggtgccga tgacgtcgaa ccaacttcta ccggtactac tgctaacttg    900

ttgaacgaag ctgacttgtc cccattggtt cctgctgccg ctccaggtgc cccaaaccag    960

gacttcgatg ccgttgatgt tcctatgaac ttgaacttca ccttcaacgg tactaacttg   1020

ttcattaacg gtgctacttt cgttccacca tccgttcctg ttttgactca aattttgtct   1080

ggtgccatga ctgctcaaga attgttgcca gccggttccg tttacacctt accaagaaac   1140

gctaccgttc aattgtcctt gcctggtaac atcattgctg gtccacaccc tttccacttg   1200

cacggtcata ccttctctgt cattagatcc gctggtcaat ctgactacaa ctacgtcgat   1260

ccaattcaaa gagatgtcgt ttccattggt ggtgctactg acaacgttac cattagattc   1320

actaccgata acccaggtcc atggttcttc cactgtcaca ttgattggca tttgcaagct   1380

ggtttcgcta tcgtttttgc tgaagaaact gccgacgttg cttccgctaa cccagttcca   1440

gctgactggt ctgccttgtg tccaacctac gatgctttgt ctgacgctga ccac         1494


<210> SEQ ID NO 35
<211> LENGTH: 2268
<212> TYPE: DNA
<213> ORGANISM: Ceriporiopsis subvermispora

<400> SEQUENCE: 35

caatccggtt cttcctacac tgacccagac aacggttttg ttttcaacgg tattaccgat     60

ccagtttacg gtgtcaccta cggtgttgtt ttcccagaac catcttcttc cggtacctac    120

ccagacgaat tcattggtga aattgtcgcc ccattgaccg ctgaatggat tggtgtttcc    180

tttggtggtg ctatgttaga ctgtttgttg ttggtcgctt ggccaaacca aaactccatt    240
```

```
gtcgcttcta ctagatacgc aaccgattac gtccaaccaa ctgaatacga cggtccagtt    300

ttgactactt tgccatcctc ctacgtcaac tccactcact ggaagtacgt ttacagatgt    360

caaaattgta ctacttggca aggtggtggt atctctttgg gtggtactgg tgttttggct    420

tgggcttact ccaacgtcgg tgtcgatgac ccatctgacc cagaatctaa cttcttagaa    480

cacaccgatt tcggtttctt cggtgaaaac ttcggtcaaa ctgaaaacgc taactacaat    540

aattacgtta acggtaatcc aggtacaccg acttcaaccc caccaactac ttctccaacc    600

ggtccaacta ctacttcacc agcttcccca ccaaccgctt ctgctacccc atacgactac    660

atcattgtcg gtgctggtgc cggtggtatc attgctgctg atagattgtc ccaaaacaac    720

aagaaggtct tgttgttgga aagaggtggt ccatccactg gtgaaaccgg tggtacttac    780

gttgccgact gggctgaagg taccaactta actaagttcg atattccagg tttgttcgaa    840

tctatgttcg acgatccaga tccatggtac tggtgttccg atgttacttt ctacgctggt    900

tgtttgttag gtggtggtac tagtgtcaac ggtgctttgt actggtaccc aaccgatacc    960

gatttctcta ctgctagagg ttggccatcc tcctggtcta accaccaagc ttacactaat   1020

gctatgactc agagattgcc atccactgac catccatcta ctgatggtga aagatacttg   1080

gaacaatctg cccaagttgc tatgcaatta ttgaacgctc aaggttatta ccaagctacc   1140

atcaacgatt ctccagattc caaggatcac gtctacggtt actctgcttt cgacttcatt   1200

aacggtaaaa gaggtggtgt cgttgctacc taccttcaaa ctgctaacca aagatctaac   1260

ttcgtctaca aggactacac tttggttagt tctgtcgtca gaaatggttc ccaaatcttg   1320

ggtgtccaaa ctaacaacac tgccattggt ccaaacggtt ttatcccttt gaacccaaac   1380

ggtagagtca tcttgtccgc tgggtctttc ggtactccaa gaatcttatt ccaatctggt   1440

attggtccta ctgacatgtt gcaaaccgtt caacaaaacg ctgctgtcgc tgccaacatg   1500

ccatccgaaa gcgactggat taacttgcca gtcggtatga acgtttccga caacccatct   1560

atcaacttgg tttttactca cccatccatc gacgcttacg ataactgggc tgacgtctgg   1620

actgacccac gtccagccga cgctgctcaa tacttggctt cccaatctgg ggttttcgcc   1680

ggtgcttctc caaaattgaa cttctggaga gattacgaag gttccgatgg tattcaaaga   1740

tccgctcaag gtactgtcag accaggtgct gcttctgtca acaccacttt gccatacaac   1800

gcttcccaaa tcttcactat taccgtttac ctgagtagtg gtatcacttc cagaggtcgt   1860

atcggtgtga ccgctggttt gaacgccgtc gctttggaaa acccatggtt gactgaccct   1920

gtcgataagg ttgtcttgat ccaagctttg gaagatgtta tctctacctt gccatccgtc   1980

ccagatttga ctatgatcac tccagattct ggtatgacct tggaagaata cgtcgatttg   2040

tacgacccat ctactatgtg ttccaaccac tgggttggtt ctgctaagat gggtacttcc   2100

tctgatactg ctgttgtcga cgaaaacgct aaggttttca acaccgataa tttgttcgtt   2160

attgacgctt ctatcgttcc atccttgcca gtcggtaacc cacacggtac tgtcatgtct   2220

gctgccgaac aagctgtcgc taacatcttg gctttgtccg gtggtcca                2268
```

<210> SEQ ID NO 36
<211> LENGTH: 996
<212> TYPE: DNA
<213> ORGANISM: Pleurotus ostreatus

<400> SEQUENCE: 36

```
gccacctgtg ctggtggtca agtcaccgct aacgctgctt gttgtgtctt gttcccatta     60
```

atggaagatt tgcaaaagaa cttgttcgac gatggtgctt gtggtgaaga tgctcatgaa 120
gctttaagat tgactttcca cgatgctatc ggtttctctc catccagagg tgtcatgggt 180
ggtgctgacg gttctgttat caccttctcc gacaccgaag tcaacttccc agctaactta 240
ggtatcgacg aaattgtcga agctgaaaag ccattcttgg ccagacacaa catttctgct 300
ggtgatttgg ttcacttcgc cggtactttg gctgtcacca actgtccagg tgccccaaga 360
atcccattct tcttgggtag accaccagct aaagccgctt ccccaattgg tttggtccca 420
gaaccattcg acactatcac cgatatccta gctagaatgg acgatgctgg tttcgttagt 480
gttgaagttg tctggttgtt gagcgctcat tccgttgccg ctgccgacca cgtcgacgaa 540
accatcccag gtactccatt cgactctacc cctaacttgt tcgactctca aatcttcatt 600
gaaacccaat tgcgtggtat ctcttttcca ggtaccggtg gtaaccacgg tgaagtccaa 660
tctccattga agggtgaaat gcgtttgcaa tccgatcatt tgttcgcccg tgacgaccgt 720
accagctgtg aatggcaatc tatgaccaac gaccaacaaa aatccaaga cagattctcc 780 gacaccttgt tcaagatgtc catgttaggt caaaaccaag acgctatgat cgactgttct 840
gacgttatcc cagtcccagc tgctttggtt accaagccac acttacctgc tggtaaatct 900
aagaccgatg tcgaacaagc ttgcgctacc ggtgctttcc cagctttggg tgctgaccca 960
ggtccagtca cctccgttcc aagagtccca ccagct 996

<210> SEQ ID NO 37
<211> LENGTH: 1011
<212> TYPE: DNA
<213> ORGANISM: Pleurotus ostreatus

<400> SEQUENCE: 37
gttacttgtg ctactggtca aactaccgct aacgaagcct gttgtgcttt gttcccaatt 60
ttggaagata tccaaactaa cttgttcgac ggtgctcaat gtggtgaaga agttcacgaa 120
tctttgagat tgaccttcca cgatgctatt gctttctccc cagccttgac taacgctggt 180
caattcggtg gtggtggtgc tgatggttct atgatcatct tctctgacac tgaaccaaac 240
ttccatgcta acttgggtat tgatgaaatc gttgaagctc aaaagccatt tatcgcaaga 300
cacaacatct ccgctgctga tttcatccaa ttcgccggtg ctatcggtgt cactaactgc 360
gccggtgctc caagattgaa cttcttcttg ggtagaccag acgctaccca aatcccacca 420
gacggtttag tcccagaacc attcgattcc gttgacaaga tcttgtctag aatgggtgat 480
gccggcttct ccactgtcga agtcgtgtgg ttgttgtcta gccacaccat cgctgctgct 540
gacttggttg acccatctat cccaggtact ccattcgact ctactccatc taccttcgat 600
agccaattct tcttggaaac tatgttgcaa ggtactgcct tcccaggtac tccaggtaac 660
caaggtgaag tcgaatctcc attggctggt gaaatgcgtt tgcaatccga cttcttattg 720
gctagagact ccagatccgc ttgtgaatgg caaagcatgg tcaacaacat gccaaagatt 780
caaaacagat tcactcaagt tatgagaaag ttgtccttgt tgggtcacaa ccaagctgac 840
ttgatcgact gttctgatgt tattccagtc ccaaagactt tgaccaaggc cgctaccttc 900
ccagccggta agtcccaagc tgacgtcgaa atcgttgtgg ccgctactcc attcccagcc 960
ttggcttctg atccaggtcc agtcaccgcc gttccaccag tcccaccatc t 1011

<210> SEQ ID NO 38
<211> LENGTH: 993
<212> TYPE: DNA
<213> ORGANISM: Pleurotus ostreatus

<400> SEQUENCE: 38
gctacctgtg ccgacggtag aaccactgcc aatgctgctt gttgtgtctt attcccaatt 60
ttggacgata tccaagaagc tctattcgat ggtgccgaat gcggtgaaga agtccacgaa 120
tccttgagat tgactttcca cgatgctatc ggtttctccc caaccaaggg tggtggtggt 180
gctgacggtt ccatcgttac ttttgacgaa attgaaactg ctttccacgc taacggtggt 240
atcgatgaca ttgtcgacgc tcaaaagcca ttcattgcca gacacaacat ctctgctggt 300
gacttcatcc aattcgccgg tgctgtcggt gtttccaatt gtccaggtgc tccaagattg 360
aacttcttat tgggtagacc accagctact gctgcctccc caaacggttt gattccagaa 420
ccattcgata ctgtcactga tattttggct agaatgggtg acgctggttt ctccccagaa 480
gaagttgttg ccttgttggc tagccatagc gtcgctgccg ctgaccacgt tgatgaaact 540
atcccaggta ccccattcga ctctactcca ggtgaattcg attcccaatt cttcattgaa 600
actcaattga gaggtaccgc tttccctggt gtcggtggta accaaggtga agtcgaatcc 660
ccattggctg gtgaaatcag aatccaatcc gatcatgact tagccagaga ttccagaact 720
gcttgtgaat ggcaatcttt cgtcaacaac caagctaagt tgcaatctgc cttcaaggct 780
gctatggata agttggctac tttgggtcaa gacagatcta agttaatcga ctgttccgat 840
gtcatccctg tcccaaagcc tttgcaatcc aaggcccact tcccagctgg tttgaccatg 900
aacaacatcg aacaagcttg tgcttctact ccattcccag ctttgactgc tgacccaggt 960
ccagtcacta ccgttccacc agtcccacca tcc 993

<210> SEQ ID NO 39
<211> LENGTH: 1011
<212> TYPE: DNA
<213> ORGANISM: Pleurotus ostreatus

<400> SEQUENCE: 39
gccaagtgtt ctaagggtag aactgcttcc aacgacgctt gttgtgtctg gttcgatgtt 60
ttggatgata tccaagaaaa cttgttcgac ggtggtgaat gtggtgaaga agtccatgaa 120
tctttaagat tgactttcca cgatgccatt ggtttctccc cagctttgac ccgtcaaggt 180
aaattcggtg gtggtggtgc tgacggttcc atcatgttgt tctctgacat tgaaactaac 240
ttcgccgcta acaacggtgt tgacgacatc gtcgaacaac aaaagccaat cgctatcaaa 300
caccaagttt cctttggtga cttcatccaa tttgctggtg ccgtcggttc ctctaactgt 360
gctggtggtc cacgtattca attcctggcc ggtagatcca acgtcaccaa gccatcccca 420
gatcacctag tcccagaacc ctttgactct gttacctcca tcttggctag aatgggtgat 480
gctggtttca agcctgacga ggttgttgct ttgttggcca gccattccgt tgctgcccaa 540
gataccatcg acccaaagtt ggctggtcac ccattcgact ctactccatc tgactttgac 600
agtcaattct ttgttgaaac cttgttaaag ggtaccttga ttccaggtga ctccttgcat 660
aagggtcaag tcaagtcccc attgccaggt gaattcagat tgcaatccga cgagttgttg 720
gctagagact ccagaacctc ttgtgaatgg caatccttta tttctaaccc aaactccatg 780
gtcccaaagt tcgaaagagc tatggctaag atggctacct tgggtcaaaa cccaaagaag 840
ttgattgatt gttctgaagt catcccagtc ccacgtggta gagttaagca accgacctta 900
cctgcgggta agactattaa ggacatcgaa gcctcctgta gaaaggctcc attcccacgt 960
ttgccaaccg acaagggtac tttcacctct atcttgccag tcccatcctc c 1011

<210> SEQ ID NO 40
<211> LENGTH: 1002
<212> TYPE: DNA
<213> ORGANISM: Pleurotus ostreatus

<400> SEQUENCE: 40

```
gctacctgtg ctgacggtaa cactgtcact aacgctgctt gctgtgtctt gttccctatc     60

ttggaagata ttcaaaccaa cttgttcgat ggtggtgaat gtggtgaaga agttcacgaa    120

tctttgagat tgaccttcca cgacgccatc ggtttctccc catctagagg tggtggtggt    180

gctgacggtt ccttaatcac cttctccgaa atcgaaaccc cattccatgc caacttgggt    240

atcgacgaaa ttgtcgaagc tcaaaagcca ttcgttgcta agcacaacat ctccgccggt    300

gatttcatcc aattcgctgg tgccgtcggt gtctctaact gtccaggtgc cccacgtcta    360

caattcttct tgggtagacc agacgctgtt gctccagctc cagatttgac ggtcccagaa    420

cctttcgaca gcgtcgactc catcttggct agattcgctg atgccggttt ctctccagct    480

gaagttgttg ctttgttggc ctcgcatacc atcgctgccg ccgacaacgt cgacccaact    540

atcccaggta ctccatttga ctctactcca tctgctttcg actcccaatt cttcgttgaa    600

acccaattgc gtggtacttc cttcccaggt accgctggta accaaggtga agttgaatcc    660

ccattgagag gtgaaatgag attgcaatct gactccgaat tggctagaga tccaagaacc    720

gcctgtgaat ggcaatcttt cgtcaacaac caatccaagt tgcaatccgc tttcaaggct    780

gctatgttaa agttgtcctt ggttgctcaa gacaagtcta agttggtcga ctgttctgac    840

gttatcccag tcccccaac cttgaacgcc gccgctcact tcccagctgg tttgaccaag    900

aacgatgttg aacaagcttg cgctgccacc ccattcccag ctttgactac cgacccaggt    960

ccagtcaccg ccgttccacc agttattcca gctttgttgc ca                      1002
```

<210> SEQ ID NO 41
<211> LENGTH: 1005
<212> TYPE: DNA
<213> ORGANISM: Pleurotus ostreatus

<400> SEQUENCE: 41

```
gctacttgtt ccggtggtag aaccaccgcc cacgcttctt gttgtatctg gttcgacgtc     60

ctggacgaca tccaagaaaa cttgtttgac ggtggtgaat gcggtgaaga agttcatgaa    120

tccttgagat tgaccttcca cgacgctatc ggtttctccc caaagttgtt cttgcaaggt    180

aagttcggtg gtttaggtgc tgacggttcc atcatggctc actctgaaat cgaaactgct    240

ttcccagcta acttgggtgt tgacgaaatc attgaagctc aaagaccatt cgccattaaa    300

cacaaagtta gctttggtga cttcatccaa ttcgccggtg ctgttggtgt ttccaactgt    360

gctggtggtg ctagaattcc attccacgct ggcagattga acgtttcttt gccatcccca    420

gatctattgg ttccagaacc atcggattct gttgacacca tcttggctag aatgggtgat    480

gctggtttct ccccaaacga agtcgttgac ttgttgatct ctcacaccgt tgctgctcaa    540

gacaacgttg acccaaccat cccaggtacc ccattcgatt ccactccaaa ctcttttgac    600

gcccaattct tcgtcgaaac cttgttgaag ggttctatta ctccaggtaa cggtaccaac    660

agaggtcaat ccttatcccc tatcccaggt gaattcagat tgacttctga cttcttgttg    720

gctcgtgacg cgagaactgc ctgtgaatgg caatccttca tcaccgacca tgcctccatg    780

gtttctaagt ttgaaaaggt catggataag atgtccacct tgggtcaaat tagagctttg    840

ttgactgact gttctgacgt cattccagtt ccaaaggttg ctttaaccaa gaccccaacc    900
```

ttgccagctg gtagaagctt ggctgacatc gaagctgctt gtcgtgctac tccattccca 960
gctttgaccg ccgacccagg tccagttacc accgtcccac cagtt 1005

<210> SEQ ID NO 42
<211> LENGTH: 1539
<212> TYPE: DNA
<213> ORGANISM: Pleurotus ostreatus

<400> SEQUENCE: 42
tctatcggtc caagaggtac cttgaacatc gccaacaagg tcattcaacc agacggtttc 60
tacagatcta ctgtcttggc tggtggttct tacccaggtc cattgattaa gggtaagact 120
ggtgatagat tccaaatcaa cgtcgtcaac aagttggctg acacttccat gccagttgac 180
acttccattc attggcacgg tttgttcgtc aagggtcaca attgggctga cggtccagct 240
atggtcaccc aatgtccaat cgttcctggt cactctttct tgtacgattt cgaagttcca 300
gaccaagccg gtactttctg gtaccactcc cacttgggta ctcaatactg cgacggtttg 360
agaggtccat tggtcgttta cagcaaaaac gatccacaca agcgtttgta cgatgttgac 420
gatgaatcta ccgttttgac tgtcggtgac tggtaccacg ctccatcctt gtctttgacc 480
ggtgttccac acccagactc caccctattt aacggtttgg gtagatcttt gaacggtcca 540
gcttccccat tgtacgtcat gaacgtcgtt aagggtaaga gatacagaat cagacttatc 600
aacacttcct gtgactccaa ctaccaattc tctattgacg gtcacacctt cactgttatc 660
gaagctgacg gtgaaaacac tcaaccattg caagttgatc aagttcaaat cttcgccggt 720
caaagatact ctttggtttt gaacgctaac caagctgttg gtaactactg gatcagagct 780
aacccaaact ctggtgaccc aggcttcgaa aaccaaatga actccgctat tttgagatac 840
aagggtgcta gatctatcga tccaaccact ccagaacaaa acgctaccaa cccactacac 900
gaatacaacc ttcgtccgtt gatcaagaaa ccagctccag gtaagccatt ccctggcggt 960
gctgatcata acattaattt gaacttcgct ttcgacccag ctaccgcttt gttcactgct 1020
aacaaccaca ctttcgtccc accaaccgtt ccagttttat tgcaaatttt gtccggtact 1080
cgcgacgccc atgacttggc cccagctggt tctatttacg atattaagtt gggtgatgtc 1140
gttgaaatca ccatgccagc tttggttttc gctggtccac acccaatcca cttgcatggt 1200
cacaccttcg ccgttgttag atccgccggt tcctctactt acaactacga aaacccagtc 1260
cgtcgtgatg tagtttccat tggtgacgac ccaactgaca acgttaccat tagattcgtc 1320
gctgacaacg caggtccatg gttcttgcac tgtcatatcg actggcactt ggacttgggt 1380
tttgccgttg tctttgctga aggtgttaac caaactgctg ctgctaaccc agttccagaa 1440
gcctggaata acttgtgtcc aatttacaac tcttccaacc catctaagtt gttgatgggt 1500
actaacgcta ttggtagatt gccagctcca ttgaaggct 1539

<210> SEQ ID NO 43
<211> LENGTH: 1518
<212> TYPE: DNA
<213> ORGANISM: Pleurotus ostreatus

<400> SEQUENCE: 43
gctatcggtc caaccggtga catgtacatt gttaacgagg atgtttcccc agacggtttc 60
acccgttccg ctgtcgtcgc cagatctgat ccaaccacta acggtaccag cgaaactttg 120
acgggtgttt tggttcaagg taacaagggt gacaactttc aattgaacgt tttgaaccaa 180

```
ttgtccgaca ccactatgtt aaagaccacc tctatccatt ggcatggttt cttccaatct    240

ggttccactt gggctgatgg tccagctttc gtcaaccagt gcccaatcgc ttctggtaac    300

tccttcttgt acgactttaa cgttccagac caagctggta ctttctggta tcactcccac    360

ttgtccaccc aatactgtga cggtttgaga ggtccattca ttgtttacga cccatctgat    420

ccacacttgt ctttgtacga cgttgataac gctgacacca tcatcacttt ggaagattgg    480

taccacgtcg ttgctccaca aaacgctgtc ttgccaaccg ctgactctac tttgatcaat    540

ggtaagggta gattcgccgg tggtccaacc tctgctttgg ccgttattaa cgtcgaatcc    600

aacaagagat acagattcag attgatctct atgtcctgcg atccaaactt taccttctcc    660

attgacggtc actccttgca ggttatcgaa gctgacgccg ttaacattgt tccaattgtc    720

gttgactcca tccaaatctt cgctggtcaa agatactctt tcgtcttgaa cgccaaccaa    780

actgttgaca actactggat cagagctgac ccaaacttgg gttccaccgg tttcgacggt    840

ggtattaact ctgccatttt gagatacgcc ggcgctaccg aggatgaccc taccaccact    900

tcctctacct ccactccatt ggaagaaacc aacttggttc cattggaaaa ccctggtgct    960

cccggtccag ccgttccagg tggtgctgac attaacatca acttggccat ggctttcgat   1020

gtcaccaact tcgaattgac catcaacggt tctccattca aggctcctac cgccccagtc   1080

ttgttgcaaa tcttgtctgg tgctaccacc gctgctagtt tgttgccatc cggttctatc   1140

tactccttgg aagccaacaa ggttgtcgaa atctccatcc cagctttggc tgttggtggt   1200

cctcacccat tccatttgca cggtcacact ttcgacgtca tcagatccgc tggttctacc   1260

acctacaact tcgacacccc cgctagaaga gatgttgtta acactggtac cgacgctaac   1320

gacaatgtta ccatcagatt cgttaccgat aaccctggtc cttggttttt gcactgtcac   1380

atcgattggc acttggaaat cggtttggct gtcgtttttg ctgaagatgt tacctccatt   1440

actgctccac cagccgcttg ggacgatttg tgcccaatct acgacgcttt gtctgattct   1500

gacaagggtg gtattgct                                                 1518
```

```
<210> SEQ ID NO 44
<211> LENGTH: 1530
<212> TYPE: DNA
<213> ORGANISM: Pleurotus ostreatus

<400> SEQUENCE: 44

gctattggtc cagctggtaa catgtacatt gtcaacgaag atgtttctcc agacggtttc     60

gcccgttctg ctgttgttgc tagatctgtt ccagctaccg atccaacccc agctaccgct    120

tctatcccag gtgtcttggt tcaaggtaac aagggtgata acttccaatt gaacgtcgtt    180

aaccaattgt ctgataccac tatgttaaaa actacttcta ttcattggca cggtttcttt    240

caagcgggca gtagttgggc tgatggtcca gctttcgtca cccaatgtcc agtcgcttcc    300

ggtgattcct tcttgtacaa cttcaacgtt ccagaccaag ccggtacttt ttggtaccac    360

tcccatttgt ccacccaata ctgtgacggt ttgcgtggtc cattcgtcgt ttacgatcca    420

tctgacccac atttgtcttt gtacgacatc gacaacgccg atactgtcat taccttggag    480

gattggtacc acattgttgc tccacaaaac gctgctatcc ctactccaga ttccaccttg    540

attaacggta agggtcgtta cgccggcggt cctacttccc cattggctat cattaacgtt    600

gaatctaaca agagatacag attcagattg gtttctatgt cctgtgaccc aaacttcacc    660

ttcagtatcg atggccactc tttgctagtc atcgaagccg acgctgttaa catcgtccca    720

attactgttg actctatcca aatttttgct ggtcaaagat actccttcgt tttgaccgct    780
```

aaccaagccg tcgataacta ctggattcgt gctaacccaa acttgggttc taccggtttc 840
gttggtggta tcaactccgc tattttgcgt tacgctggtg ccaccgaaga tgacccaacc 900
accacctctt ccacctctac cccattgttg gaaaccaact tagtcccatt ggaaaaccca 960
ggtgctccag gtccacctgt tccaggtggt gctgatatca acattaactt ggccatggct 1020
ttcgatttca ccaccttcga attgactatt aacggtgtcc cattcttacc accaaccgct 1080
cctgttttgt tgcaaatttt gtctggtgct tccactgctg cttccttgtt gccatccggt 1140
tccatctacg aattggaagc taacaaggtt gtcgaaatct ctatgccagc cctggctgtc 1200
ggtggtccac acccattcca cttgcatggt cacaccttcg acgttattag atccgctggt 1260
tctaccacct acaacttcga caccccagct agacgtgatg tcgttaacac tggtactggt 1320
gctaacgaca acgtgaccat cagattcgtt actgacaacc caggtccatg gttcttgcac 1380
tgtcacatcg actggcattt ggaaatcggt ttggccgttg ttttcgctga agatgttacc 1440
tctatttctg ccccaccagc tgcttgggac gacttgtgtc ccatctacaa cgccttgtca 1500
gacaacgata agggtggtat tgttccatcg 1530

<210> SEQ ID NO 45
<211> LENGTH: 993
<212> TYPE: DNA
<213> ORGANISM: Pleurotus ostreatus

<400> SEQUENCE: 45
gctacttgtg ctgacggtcg taccaccgct aacgctgctt gttgtgtctt gttcccaatt 60
ttggatgaca tccaagaaaa cttgttcgat ggtgctcaat gtggtgaaga agttcatgaa 120
tctttgagat tgacctttca cgacgctatt ggtttctctc caactttggg tggtggtggt 180
gctgacggtt ccatcattac cttcgatacc atcgaaacca actttccagc taacgctggt 240
attgatgaaa tcgtttccgc ccaaaagcca ttcgttgcta agcacaacat ttctgctggt 300
gacttcatcc aattcgctgg tgctgtcggt gtttctaact gtccaggtgg tgtcagaatc 360
ccattcttct tgggtagacc agatgctgtt gctgcttctc cagaccactt ggtcccagaa 420
ccattcgata gcgttgacac catcttggct agaatgggtg atgctggttt ttctgctgtc 480
gaagttgtct ggttgttggc ttctcattcc atcgccgccg ctgacaaggt cgacccaagc 540
atcccaggta ccccattcga ctctactcca ggtgtctttg actctcaatt tttcatcgaa 600
acccaattga agggtagatt gttccctggt accccagata acaagggtga agttcaatcc 660
ccattgcaag gtgaaatcag attgcaatct gaccacttgt tggcccgtga tccacaaacc 720
gcttgtgaat ggcaatctat ggtcaacaac caaccaaaga tccaaaacag atttgctggt 780
accatgtcta agatggcttt gttgggtcaa gataaatcta agttgatcga ctgttccgat 840
atcattccaa ctccaccagc tttggtcggt gctgctcatt tgccagctgg tttctcttta 900
tctgacgtcg aacaagcttg tgctgaaacc ccattccctg ctttgaccgc tgacccaggt 960
ccagttactt ctgttccacc agtcccaggt tct 993

<210> SEQ ID NO 46
<211> LENGTH: 1194
<212> TYPE: DNA
<213> ORGANISM: Pleurotus ostreatus

<400> SEQUENCE: 46
gtcacttgtg ccaccggtca aactaccgct aacgaagctt gctgtgcctt attcccaatt 60

```
ttggaggata ttcaaactaa cttgttcgac ggtgctcaat gtggtgaaga agtccacgaa    120

tctttgagat tgactttcca tgacgctatc gctttttccc cagccttgac taacgctggt    180

caattcggtg gtggtggtgc tgacggttcc atgattatct tctccgatac tgaaccaaac    240

ttccacgcca acttgggtat cgacgaaatc gttgaagctc aaaagccatt catcgctaga    300

cacaacattt ctgccgctga tttcatccaa ttcgctggtg ctattggtgt ctccaactgt    360

gctggtgctc caagattgaa cttcttcttg ggtagaccag acgctaccca aatcccacca    420

gacgggttgg tcccagaacc attcgacagc gttgacaaga tcctatctag aatgggtgac    480

gctggtttca gcactgtcga agtcgtttgg ttgttgagtt cacacaccat cgccgctgcc    540

gacttggtcg acccatctat tccaggtact ccattcgact ccactccatc taccttcgac    600

tctcaattct tcttggaaac catgttgcaa ggtaccgctt tcccaggtac tccaggtaac    660

caaggtgaag ttgaatcccc attggccggt gaaatgagat tacaatctga cttcttggtc    720

tactctcgtt ccgcttgtga atggcaatct atggtcaaca acatgccaaa aatccaaaac    780

agattcaccc aagtcatgag aaagttgagc ttgttgggtc acaatcaagc tgatttaatc    840

gactgctctg acgtcatccc tgttcctaag actttgacta aggccgccac cttccctgct    900

ggtaagtccc aagccgacgt tgaaatcgtc gtcgctgcca ctccattccc tgctttggct    960

tccgacccag gtccagttac tgctgttcca ccagtctacg cccctcactt ggctttgcac   1020

ttgtttaaca aattgactta ctgtgccgct cgtttgagaa agtgcctaga tagaatcttg   1080

tgttccagct tctcctttcc atccgaattc tctgtccaac cattatacaa gtgtaagatc   1140

tgttgtattt gttccatccc agaatacact gccttcccat gcgctagatt gcgt         1194
```

<210> SEQ ID NO 47
<211> LENGTH: 993
<212> TYPE: DNA
<213> ORGANISM: Pleurotus ostreatus

<400> SEQUENCE: 47

```
gctacctgtg ccggtggtca agtcactgcc aacgctgcct gttgtgtttt gttccccatc     60

ttggaagatt tgcaacaaaa cttattcgac ggtggtgaat gtggtgaaga agtccacgaa    120

tctttgagat taaccttcca cgacgctatc ggtttctctc caaccaaggg tggtggtggt    180

gctgacggtt ccgtcttgac cttctctgat ccagaagtta acttcccagc taacttaggt    240

attgacgaaa tcgtcgaagc tcaaaagcca ttcttggcta gacataacat ctccgctggt    300

gatttggtcc aattcgccgg tgctttaggt gtttccaact gtcctggtgc cccaagaatt    360

ccattcttct tgggtagacc accagccaag gccgcttctc caatcggttt ggtcccagaa    420

cctttcgaca ccgtcaccga catcttggac agaatgggtg acgctggttt cgctgccgtc    480

gaagttgtct ggttgttgtc ctctcacact atcgctgctg ccgaccacgt tgatgaatcc    540

atcccaggta ccccattcga ctccacccca agcatcttcg actcccaatt tttcattgaa    600

actcaattga gaggtacttc cttcccaggt tctggtggta accacggtga agtcgaatcc    660

ccattggctg gtgaaatcag attgcaatcc gatcacctat tggctagaga ctccagaacc    720

tcctgcgaat ggcaatctat ggttgacaac atgccaaaga ttcaaaacag atttgctgcc    780

accatgttga agatgtcttt gcttggtcaa aaccaagctg acttaattga ctgttctgat    840

gttatcccaa ctccaccagc cttggtcggt aaggctcatt taccagccgg taaggtccaa    900

tccgacgttg aacaagcttg cgccaccact ccattcccag ctattgccgc tgatccaggt    960

ccagttaccg ctgtccctcc agttccacca tcc                                 993
```

<210> SEQ ID NO 48
<211> LENGTH: 1701
<212> TYPE: DNA
<213> ORGANISM: Pleurotus ostreatus

<400> SEQUENCE: 48

```
aactctttcg actacgttgt cgttggtggt ggtaccgccg gcgctgttat cgctaacaga     60
ttaactgaaa acccaagagt cactgtttta ttgttggaag ctggtccatc caacattaac    120
gttaccaact ctatcgttcc attgttgcac aacttcttga ttccaaacac cccatacgac    180
tggaacttca ccacgactaa ccaagttggt ttcaacggta gaaacatcag cttcccacgt    240
ggtcacatgt tgggtggttc ttcttctgtt aacggtttgg ttttcaccag aggttcctct    300
gacgactggg atgcctacgc tgctattgct gaagatccat cttggacctg ggaaaacatc    360
caacgttact tgccattaat tgaacaattc accgaaccta tcgaaccata caacattacc    420
ggtgatttca ttccatcctt gcacggtacc gacggtaaaa tccaaacctc tgttgccaac    480
tacagaatcc cattggacga gcacatcatc gaagcttccc aagaattggg tgacgaattc    540
ccattcaacc cagatatggg tggtggtgaa aatgttttgg gtttgggttg gaccgtcagt    600
accatcggta gaggtgttag atcttcttcc gctaccggtt acttggcccc agaatacttg    660
tccagaccaa acttgcatgt cttggttcat gctcaagtta ccaagttgat tcaaaccggt    720
accagaaaca gattgccatc tttccactcc ttgcaattca cgtccacctt ggctgctcgt    780
ccaatcaccg tcaccggtcg tcgtgcggtt gttttgagcg ctggtgcagt cggtactcca    840
cacattttgc aattgtctgg gatcggtgac agatccttgt tagaatccgt tggtattaga    900
accattgttc acaacccatc tgttggtaga aacttgtctg atcacccatt gttggcttgt    960
gtttactcgg tccatgacaa ctcttcttac gacatcttat tcagagaacc agctgttttt   1020
caagccgcta tggaccaatg gaacgctaac cacaccggtc caggtgccgc cagtgtcttt   1080
aatcaagttg gtttcttcag attgccagac aacgctacca tttttgaaac cactccagac   1140
ccagcttccg gtccaaagtc cggtcacttc gaaatcatgt tctcaaactt ctacaactta   1200
ccaggtttgg ccgctccaac ctctggtacc accatctctt tcgacgtcgc tgttattcca   1260
gctacttcca gaggttctgt cgaattaacc tctaccgacc cattcgctgc tccagctatc   1320
gacccagctt acctacaatc cgaattcgat attttcacta tgttggaagc tgttaaggct   1380
gtcagaagat tcgccgaagc tcaaaccttc gacggttaca tcattgaacc attcggtgaa   1440
ttcggtgctg ctaccactga tgaattgttg gaaaccttcg ctagaggtaa cgccgccact   1500
gtttttcacc cagtcggtac ctcttccatg tctccaaaag gtgctaactg ggtgtcgtt    1560
gacccagatt tgagagttaa gggtgttgaa ggtttgttta tcattgacgc tggtgttatc   1620
aacaagttgc caaccgccca caccatggct ccaactttca tcgtcgctga aagaggtgct   1680
gaattactta aggctttgac c                                             1701
```

<210> SEQ ID NO 49
<211> LENGTH: 1107
<212> TYPE: DNA
<213> ORGANISM: Dichomitus squalens

<400> SEQUENCE: 49

```
gttacttgtt ctgacggtac cgttgttcca gactccgtct gttgtgaatt cattccattg     60
agagaagctt tgaacgacca agttattcaa tccgattgtg gtgaggatgc tcacgaatta    120
```

```
ttgagattga ctttccacga cgccatcgct atttcccaat ctttgggtcc ttccgctggg    180

ggtggtgctg acggttctat gttgttattc ccaaccgtcg aaccagcttt cttcgccaac    240

ttgggtatcg ctgactccgt taacaatttg atcccattca tgtcccaatt cccaaacatc    300

tccccaggtg acttggtcca attcgctggt gctgttgcca ttactaactg tccaggtgct    360

ccacaattgg aattcttggc tggtagacca aacggtactg caccagctat cgatggtttg    420

atcccagaac cacaagattc cattgacgat atcttggcta gattcgacga cgctggtggt    480

ttcactccat tcgaagttgt ttctctgttg gcttccccata ctgttgctag agctgaccac    540

gtcgacccaa ccttggacgc tgctccattt gactctaccc cattcacctt cgatacccaa    600

atcttcttgg aagttttgtt gaagggtacc ggtttcccag gtaccgacaa caacaccggt    660

gaggttgcca gcccaattcc agttactaac ggtaccgatg ttggtgaatt gagattgcaa    720

agcgacttcg gtttggctca cgattccaga accgcttgtt tctggcaagg tttcgtcaac    780

caacaagatt tcatggccca atctttcaag gctgctatgg ccaagttggc tgttttgggt    840

cacaacgctg ctgatttggt taactgttcc gccgttattc caaccccatt gccagctact    900

ggtaagccag ctaccttccc agctactttg ggtccagacg atttggaatt gtcttgtacc    960

accgaaccat tcccatctct aactaccgac ccaggtgccc aagaaacctt aattcctcac   1020

tgttctgatg gttccatgga ctgtgagtct gttcaatttg acggtccagc tactaacttc   1080

ggtggtgatg acgatgatga cgattct                                       1107


<210> SEQ ID NO 50
<211> LENGTH: 1095
<212> TYPE: DNA
<213> ORGANISM: Dichomitus squalens

<400> SEQUENCE: 50

accgtctgtt ccgatggtac cgtcgttcca gactctgtct gttgcgaatt cgtcccattg     60

gctcaagctt tgcaaaagga agttttgatg ggtgattgtg gtgaggatgc tcacgaatta    120

ttgagattga ctttccacga cgccatcgct atttccagat ctaagggtcc atccgctggt    180

ggtggtgccg acggttctat gttgatcttc ccaaccgtcg aaccagcttt cttcgctaac    240

ttgggtatcg ctgactctgt caacaatttg attccattct tgtcccaatt cccaaagatc    300

tctgctggtg acttggtcca attcgctggt gccgttgccg tcggtaactg tccaggtgcc    360

ccacaattgg aattccgtgc cggtagacca aacgccaccg ccccagctat cgaaggtttg    420

attccagaac cacaaaacaa cattaccgaa attttggaaa gattcgacga cgctggtggt    480

ttttccccat tcgaagtcgt ttctttgttg gcttcacata ctgtcgccag agccgatcac    540

gtcgacccaa ccttggatgc tgctccattc gactctactc ctttcacttt cgatacccaa    600

atttttttgg aagttttgtt gaagggtgtc ggtttcccag gtaccggtaa caacactggt    660

gaagtttcct ccccattgcc agtctcttct ggtaccgacg tcggtgaatt gagattgcaa    720

tccgacttcg gtttagctca cgatgaacgt actgcctgtt tctggcaagg tttcgttaat    780

gaacaagaat tcatggccca atccttcaaa gccgctatgg ctaagttggc tgtcttgggt    840

cacaacgccg acgatttggt cgactgttcc gctgtcgtcc caaagccaaa gccagccacc    900

ggtaagccag cttccttccc agcaaccaag ggtccaaagg acttggaatt gtcctgtact    960

tctaagaagt tcccaacctt gaccaccgac cacggtgctc aagaaacttt gatcccacac   1020

tgttccaacg gttccatgaa ttgtaccact gtccaattcg atggtccagc caccaacttc   1080

gacggtgatg actcc                                                    1095
```

<210> SEQ ID NO 51
<211> LENGTH: 1026
<212> TYPE: DNA
<213> ORGANISM: Trametes versicolor

<400> SEQUENCE: 51

```
gttgcttgtc cagacggtaa gaacactgct accaacgctg cttgttgttc tttgttcgcc     60

gtccgtgacg acattcaaca aaacttgttc cacggtgctc aatgtggtga aaacgctcac    120

gaatccttga gaattacttt ccacgatgct atctctttct ccccagctat ggaagctaga    180

ggtcaattcg gtggtggtgg tgctgacggt agtattgcta tcttccctga tattgaaacc    240

aacttccacg ctaacattgg tttggacgaa atcgttgccg aacaagctcc aattcaagct    300

agacataatt tgtcccacgc tgacttcatt atgtttgctg gtgctttggg tacctctaac    360

tgtccaggtg ctccacgttt ggatttcttc ttgggtagaa aggacgctac tagaccagcc    420

cctgatggtt tggttccaga accattcgat accttggaag atgtttttgc tagattggct    480

gacgcttctg ctggtgaatt cgatgaaatc ttaacggttt ggttattgac cgctcacacc    540

atcgctgcta ccgatcactt ggaccctact attccaggta ccccaatgga ttctacccca    600

cacatctggg acacccaatt cttcatcgaa acccaattga gaggtactgc cttcccaggt    660

accggtggta accacggtga agttatgtcc ccattgaagg gtgaaattcg tttgcaaacc    720

gatcacttat tggctcgtga ctctagaacc tcttgtgaat ggcaatcttt cgtcaacaac    780

caacaaaagg ctcaagatat gttcgccttt gttttccacg atctatccat gttgggtcaa    840

gacccagatt ctttgattga ctgttccgaa ttgatcccac agccagctcc agtcatcggt    900

aaggctcact tcccagctgg tttgaccaac aaggacattg aacaagcctg tgctgacact    960

ccattcccaa ccttgccaac cgacccaggt ccaaagacca ctgttgctgc agttccaatc   1020

aactcc                                                              1026
```

<210> SEQ ID NO 52
<211> LENGTH: 1023
<212> TYPE: DNA
<213> ORGANISM: Trametes versicolor

<400> SEQUENCE: 52

```
gtcgcttgtc cagacggtgt taacactgcc accaacgccg cttgttgtca attgttcgcc     60

gtccgtgacg acttgcaaga aaacttgttc cacggtggtt tgtgtaccgc tgaagcccac    120

gaatctttga gattaacttt ccacgatgct attgctatct ccccagcctt ggaacaacaa    180

ggtatttttg gtggtggtgg tgccgacggt tctatcgcta tcttctccga tatcgaaacc    240

gccttccatc caaacattgg tttggacgaa atcgttgaat tgcaaaagcc attcatcgct    300

agacacaatc tatctgttgc tgacttcatc caattcgctg gtgctatcgg tgcttctaac    360

tgtgccggtg ccccacaatt ggctgctttt gtcggtagag ttgacgccac ccaaccagct    420

ccagatggtt tggtcccaga accattccat actcctgacc aaatcttcgc cagattggct    480

gacgcttccc aaggtgaatt tgatgaaatt ttgaccgttt ggctattggt tgctcacacc    540

gttgccgctg ccaacgacgt tgacccaacc gtcccaggtt ccccattcga cagcacccca    600

gaagtctggg atactcaatt cttcgttgaa gttttattga acggtaccac tttcccaggt    660

actggtgaca accaaggtga agtcgcttcc ccaattgccg gtgaattccg tttgcaatct    720

gacttcgcta ttgctagaga ctcccgtagc gcctgtgaat ggcaatcctt tgttgataac    780
```

caaccaaagg ctcaggctat gttccaattc gttttccatg acttgtctat tttcggtcaa 840
gacattaact ccttggtcga ttgtactgaa gtcgttccaa tccctgctcc attgcaaggt 900
gtcactcact tcccagctgg tttgactgtt aacgacattg accaaccatg tgttgaaacc 960
ccattcccta ccctaccaac cgaccctggt ccagctacct ccgttgctcc agttcctcta 1020
cca 1023

<210> SEQ ID NO 53
<211> LENGTH: 1038
<212> TYPE: DNA
<213> ORGANISM: Trametes versicolor

<400> SEQUENCE: 53
gttgcctgcc cagacggtgt caacaccgct accaacgctg cttgttgtca attgttcgct 60
gtcagagaag atttgcaaca aaacttattc cacggtggtt tgtgtaccgc tgaagctcat 120
gaatctttga gattaacttt ccacgacgct attgccatct cccctgcttt ggaagctcaa 180
ggtattttcg gtggtggtgg tgccgacggt tctatcgcta ttttcccaga aatcgaaact 240
aacttccacc caaacatcgg tttagacgaa attatcgagt tgcaaaagcc tttcatcgct 300
agacacaaca tctccgttgc tgatttcatt caattcgccg gtgctatcgg tgctagcaac 360
tgtgctggtg ctccacaatt ggctgctttc gttggtagaa aggacgccac ccaaccagct 420
ccagatggtt tagttccaga accatttcat accccagatc aaatcttcga cagattggct 480
gatgcttctc aaggtgaatt cgacccaatt ctaaccgttt ggttgttgac tgctcacacc 540
gtcgccgctg ctaacgacgt tgatccaact aagtccggtt tgccattcga ctccacccca 600
gaattgtggg acacccaatt cttcttggaa acccaattga gaggtacttc tttcccaggt 660
tccggtggta accaaggtga ggttgaatct ccattagctg gtgaaatgag attgcaatcc 720
gaccacacca tcgctagaga ctctagaact gcttgcgaat ggcaatcttt cgtcgacaac 780
caaccaaagg cccaacaaat gttccaattc gttttccacg acttgtccat cttcggtcaa 840
gatatcaaca ccttggttga ttgtactgaa gtcgttccaa ttccagctga cccacaaggt 900
catacccact tcccagccgg tttgtccaac gctgatatcg aacaagcttg tgccgaaacc 960
cctttcccaa ccttcccaac tgacccaggt ccaaagaccg ctgtcgctcc agttccaaag 1020
ccaccagctg ctagaaag 1038

<210> SEQ ID NO 54
<211> LENGTH: 1008
<212> TYPE: DNA
<213> ORGANISM: Trametes versicolor

<400> SEQUENCE: 54
gctacctgtt ctggtggtca aaccactgcc aacgatgctt gttgtgtttg gttcgatgtc 60
ttggatgaca tccaatccaa cttgttccac ggtggtgaat gtggtgaaaa cgcccatgaa 120
agcttgagat tgattttcca cgatgctatt gccttctccc cagctctaac tgctgccggt 180
caattcggtg gtggtggtgc tgacggttct atcatggctc acaccgatgt cgaaattcaa 240
tacgctgcta acaacggttt ggacgaaatt atcgaagaac aaagaccatt cgctttgaag 300
cataacgttt ctttcgggga ttttattcaa ttcgccggtg ctgttggtgt cgctaattgt 360
aacggtggtc cacaaatcgg cttcttcgct ggtagatcca acgactctca accagctcca 420
gataaattgg ttccattgcc atccgattcc gtcactgaca ttttagcccg tgtcgccgat 480
gctggtttcg ctcctgtcga attggtctgg atgttaattt cccacaccgt cgccgctcaa 540

```
gataaggtcg atgacagcat tccaggtacc ccattcgact ctactccatc cgattttgac    600

gcccaattct tcgttgaatc tatgttgaat ggtactttaa ctccaggttc cgccttgcac    660

gacggtgagg tccaatcccc attgccaggt gaattcagat tgcaatccga cttcttaatc    720

ggtagagata gcagaacctc ctgtgaatgg caaaagatga ttgctgatag agccaacatg    780

ttgcaaaaat tcgaacaaac cgtcttgaag ttgttgggtt tctctcaatc cgccttgact    840

gattgctctg acgttattcc aattgctacc ggtaccgttg ccgatccatt cttgccagct    900

ggtaagacta tggctgatat cgaagccgct tgtgctgcta ccccattccc aactttgtcc    960

gccgcttccg gtccagaaac caccatccca gctgttccat tagactcc                1008


<210> SEQ ID NO 55
<211> LENGTH: 1017
<212> TYPE: DNA
<213> ORGANISM: Trametes versicolor

<400> SEQUENCE: 55

gtcgcttgtc cagacggtgt taacaccgct actaacgctg cttgttgtca attgttcgct     60

gtccgtgacg acattcaaaa gaacttgttt gataacggtg aatgtggtga agatgttcac    120

gaatccttga gattgacctt ccatgacgcc atcggtttct ccagatctgc tgaagctaat    180

ggtactttcg gtggtggtgg tgccgatggt tccatcagca tcttcgcttc cattgaaacc    240

aacttccacg cttccttggg tatcgatgaa atcgtcggtg aacaagctcc attcatcgct    300

agacacaatt taaccgttgg tgatttcatc caattcgctg gtgctgttgg tgtttctaac    360

tgcccaggtg ccccaagatt gcaattcttg ttgggtagac caaacgctac ccaaccagct    420

ccagacaaga ctatcccaga accattcgac accgttgatt ccatcttggc cagattcttg    480

gacgctgctg atttctctcc tgctgaagtt gttgctttat tggcttccca cactattgct    540

gctgctgacg aagtcgaccc aaccattcca ggtactccat tcgactccac cccagaattg    600

tttgatactc aattcttcat cgaaacccaa ttgagaggta ccggtttccc aggtaccgct    660

ggtaaccaag gtgaagtttt atccccattg ccaggtgaaa tgagattgca atctgactcc    720

gaattggcca gagactccag aaccgcttgt gaatggcaat ctatggttaa caaccaatct    780

aagatgatga ccgctttcgc cgctgccatg gctaagttgg ctgtcatcgg tcaagacgtt    840

tctcaattga ttgactgttc cgaagttatc ccaatgccac caccaccagc ttccgctgct    900

cacttcccag ccggtttatc caacgctgat gttgaacaag cctgtgctga aactccattc    960

ccaaccttgc aaaccgaccc tggtccagaa acctctgtcg ctccagttcc accatcc     1017


<210> SEQ ID NO 56
<211> LENGTH: 1014
<212> TYPE: DNA
<213> ORGANISM: Trametes versicolor

<400> SEQUENCE: 56

gtcacttgtg cttccggtca agttacctcc aacgctgctt gttgtgccct attcccagtc     60

atcgatgata ttcaagccaa tatgttcgac ggtggtgaat gtaacgaaga tgttcacgaa    120

tccctaagat tgaccttcca cgatgccatc ggtatttccc gtaaggctaa caaggccggt    180

gtctttggtg gtggtggtgc cgacggttcc atcgctattt tcgctgacat tgaaactaac    240

tttcacgcta acaacggtgt tgatgaaatc attgacaccc aagctccaat catcgctaga    300

cataacctaa ccactgctga cttcatccaa ttcgccggtg ctattggtgt ttctaactgt    360
```

```
ccaggtgccc caagattgga tgtctttttg ggtagaaagg atgctaccca accagcccca    420

gacttgaccg ttcctgaacc attcgatgac gtcactaaga ttttggctag attcgatgac    480

gccggtaagt tctcctctga cgaagttgtt gccttgttgg tttctcacac cattgctgct    540

gctgaccacg ttgatccaac tattccaggt accccattcg actccacccc agaattattc    600

gacacccaat tcttcatcga aacccaattg caaggtactt tgttcccagg taacggttcc    660

aaccaaggtg aagttatgtc cccattgaga ggtgaaatta gattgcaatc cgacttcttg    720

ttggctagag attctagaac cgcttgtgaa tggcaatcct tcgttaacaa ccaatacaaa    780

ttgcaatccg ctttcaaggc tgctttccgt aagatgacta tcttgggttc caaggaacac    840

aacttgattg attgttctga tgttgtccca actccaccag ccccagcttc taaagctcac    900

ttgccagccg gtttgaccag acaagatgtt caacaagctt gcaacaagaa ggccttccca    960

accttgccaa ccgacccagg tccagtcact tccgttgccc cagtcccacc ctcc         1014
```

<210> SEQ ID NO 57
<211> LENGTH: 1017
<212> TYPE: DNA
<213> ORGANISM: Trametes versicolor

<400> SEQUENCE: 57

```
gttgcttgtc cagatggtgt caacaccgct accaacgccg cttgttgtca attgttcgct     60

gttcgtgacg atatccaaca aaacttattc gacggtggtg aatgtggtga agaagttcac    120

gaatccttgc gtttaacctt ccacgacgct atcggtatct ccccttctat cgcttcccgt    180

ggtcaattcg gtggtggtgg tgctgacggg tccattgctt tgtttgaaga tattgaaact    240

aacttccacg ctaacttggg tgttgatgaa attatcgacg aacaaagacc attcatcgcc    300

agacacaact tgaccactgc tgacttcatt cagtttgccg gtgctatcgg tgtttccaac    360

tgtccaggtg ctccacaatt ggatgttttt attggtagac cagacgccac ccaaccagcc    420

ccagatttga ccgttccaga accatttgac accgtcgact ctattattga aagattctcc    480

gatgctggtg gtttcactcc agctgaaatc gttgctttgt tggtttctca caccatcgct    540

gcagctgacc acgtcgaccc atccatccca ggtaccccat tcgattccac cccagaagaa    600

ttcgacactc aattctttat cgaaactcaa ttgagaggta ccttgttccc aggtactggt    660

ggtaaccaag gtgaagttga atccccatta agaggtgaat tgcgtttgca atcagattcc    720

gaattggcca gagattccag aaccgcttgc gaatggcaat ccttcgtcaa caaccaagct    780

aagttgcaat ccgctttcaa ggctgctttc agaaagatga ctgttttggg tcacgacgaa    840

tccttgttga ttgaatgctc cgaattggtc ccaactccac caccagccac ctctgttgct    900

cacttccctg ctggtttgtc caacgctgac gtcgaacaag cctgtgctga aaccccattc    960

ccaactttac caaccgatcc aggtccagtt actactgttg ctccagttcc accatcc      1017
```

<210> SEQ ID NO 58
<211> LENGTH: 1494
<212> TYPE: DNA
<213> ORGANISM: Trametes versicolor

<400> SEQUENCE: 58

```
gccatcggtc ccgttactga cttgaccatc tctaacgctg atgtcagtcc agacggtttc     60

accagagctg ctgtcttggc caacggtgtt ttcccaggtc cattgattac tggcaacaaa    120

ggtgacaact tccaaatcaa cgtcattgat aacttgtcta acgaaaccat gttaaagtct    180

acttctatcc actggcacgg tttcttccaa aagggtacta actgggccga cggtgctgct    240
```

```
ttcgtcaacc aatgtccaat tgctaccggt aactctttct tatacgactt cactgctacc    300

gatcaagctg gtaccttctg gtaccactcc cacttgtcta ctcaatactg tgacggtttg    360

agaggtccaa tggtcgttta cgatccatcc gacccacatg ctgacttata cgatgttgac    420

gatgaaacta ctattatcac tttgtccgac tggtaccaca ccgctgcttc tcttggtgct    480

gctttcccaa ttggttccga ttccaccttg atcaacggtt taggtagatt cgccggtggt    540

gactccactg acttggctgt tattactgtc gaacaaggta agagatacag aatgagattg    600

ttatctttgt cttgtgaccc aaactacgtt ttctctatcg acggtcacaa catgaccatt    660

atcgaagctg acgctgtcaa ccacgaacca ttgaccgtcg attccatcca aatttacgct    720

gggcaaagat attccttcgt tttgactgct gaccaagata tcgacaatta cttcatccgt    780

gctttacctt ctgctggtac cacctctttc gacggtggta tcaactctgc tattttgaga    840

tactccggtg cctccgaagt cgacccaact actactgaaa ccacttctgt tttgccattg    900

gacgaagcta acttagtccc attggattct ccagccgccc cgggtgaccc aaatattggt    960

ggtgtcgact acgctttgaa cttggatttc aactttgacg gtactaactt cttcatcaac   1020

gacgtttctt tcgtttctcc aaccgttcca gtcttgttgc aaattttatc cggtactacc   1080

tccgctgctg acttgttgcc ttctggttct ttgttcgctt tgccatctaa ctccaccatc   1140

gaaatttcct tcccaatcac tgctaccaac gccccaggtg ccccacatcc attccattta   1200

cacggtcaca ctttctctat tgtcagaacc gctggttcca ctgatactaa cttcgttaac   1260

ccagtcagac gagatgtcgt taacaccggt accgccggtg ataacgtcac catcagattc   1320

actaccgaca acccaggtcc atggttcttg cactgtcaca tcgacttcca cttggaagcc   1380

ggttttgcta ttgttttctc tgaagatacc gccgatgttt ccaacactac taccccttct   1440

actgcttggg aagatttgtg tccaacttac aacgctttag attcttctga cttg         1494
```

<210> SEQ ID NO 59
<211> LENGTH: 1497
<212> TYPE: DNA
<213> ORGANISM: Trametes versicolor

<400> SEQUENCE: 59

```
ggtattggtc cagttgctga cttgaccatt actaacgctg cggtcagccc tgatggtttc     60

tccagacaag ctgttgttgt caacggtggt accccaggtc cattgatcac tggtaacatg    120

ggtgacagat ttcaattgaa cgttatcgat aacttaaccg accacactat gttgaagtct    180

acttctatcc actggcacgg tttcttccaa aagggtacca actgggccga tggtccagct    240

tttattaatc aatgcccaat ctcttctggt cactccttct tgtacgactt ccaagttcca    300

gatcaagctg gtacgttttg gtaccactcc cacttgtcta cccaatactg tgacggttta    360

agaggtccat tcgttgttta cgacccaaac gatccagccg ctgacttgta cgacgtggac    420

aacgacgata ccgttattac cttagccgac tggtaccacg ttgctgctaa gttgggtcca    480

gcttttccat tgggtgccga cgccactttg atcaacggta agggtagatc cccatctacc    540

accaccgctg atttgactgt catctctgtt accccaggta agagatacag attcagattg    600

gtttccttgt cctgtgaccc aaaccacact ttctctattg acggtcacaa catgaccatt    660

atcgaaactg actccatcaa cactgcccct ttggtcgttg actcaattca aatcttcgct    720

gctcaaagat actccttcgt cttggaagct aatcaagctg ttgataacta ctggattcgt    780

gctaacccat cctttggtaa cgtcggtttc accggtggta tcaactctgc cattttgaga    840
```

```
tacgacggtg ctgccgctat tgaaccaact accacccaaa ctacctctac tgaaccattg    900
aacgaagtta acttacaccc attagttgcc accgctgttc caggttctcc agccgctggt    960
ggtgtcgatt tggctattaa catggctttc aatttcaacg gtactaactt ctttatcaac   1020
ggtgcttcct tcacccctcc aaccgttcca gttttgttgc aaattatttc cggtgcccaa   1080
aacgcccaag acttattgcc atctggttcc gtctactctt tgccatctaa cgctgatatc   1140
gaaatctctt tcccagccac tgctgctgcc ccaggcgccc cacatccatt ccacttgcac   1200
ggtcacgctt tcgctgttgt tagatccgct ggttccaccg tctacaacta cgacaaccca   1260
atcttcagag atgttgtttc tactggtacc ccagctgccg gtgacaatgt caccattaga   1320
ttcagaaccg ataacccagg tccatggttt ttgcattgtc acatcgattt ccacttggaa   1380
gccggtttcg ctgttgtttt tgccgaagat attcctgacg ttgcttctgc taacccagtt   1440
ccacaagctt ggagcgactt gtgtccaact tacgatgccc gagatccatc tgaccaa      1497
```

<210> SEQ ID NO 60
<211> LENGTH: 1497
<212> TYPE: DNA
<213> ORGANISM: Trametes versicolor

<400> SEQUENCE: 60

```
gctatcggtc cagttgcttc tttggttgtc gccaacgccc cagtttcccc agatggtttc     60
ttaagagatg ctattgttgt taacggtgtt gttccatccc cattgatcac tggtaagaag    120
ggtgacagat ttcaattgaa cgtcgttgac actttgacta accattccat gttgaagtcc    180
acctctattc actggcacgg ttttttccaa gccggtacca actgggctga cggtccagcc    240
ttcgtcaacc aatgtccaat cgcctctggt cattccttct tgtacgattt ccacgttcca    300
gatcaagctg gtactttctg gtaccactct cacttatcta ctcaatactg tgacggtttg    360
agaggtccat tcgttgttta cgacccaaag gacccccacg cttccagata cgatgtcgac    420
aacgaatcca ctgttattac tttgactgac tggtaccata ccgctgctag attgggtcca    480
agatttccat tgggtgctga cgccactttg atcaacggtt tgggtcgttc cgcttctacc    540
ccaaccgctg ccttggctgt cattaacgtt caacacggta agagataccg tttcagatta    600
gtttccattt cttgtgatcc aaactacact ttctctatcg acggtcacaa cttgactgtt    660
attgaagttg acggtattaa cagccaacca ttgttggttg actccatcca aatcttcgct    720
gcccaaagat actccttcgt tttgaacgct aaccaaaccg ttggtaacta ctgggtcaga    780
gctaacccaa acttcggtac tgttggtttt gccggtggta ttaactctgc tattttgaga    840
taccaaggtg ccccagttgc tgagccaacc actacccaaa ctccatctgt cattccttta    900
atcgaaacca acttgcaccc attggccaga atgccagttc caggtagccc aactccaggt    960
ggtgtcgaca aggctttgaa cttagccttc aacttcaacg gtactaactt tttcattgac   1020
aacgcctcct ttactccacc aactgtccca gtcttgttgc aaatcttgtc cggtgctcaa   1080
accgctcaag aattgttgcc agccggttcc gtttacccat tgccagccca ttctaccatc   1140
gaaattactt tacctgctac tgctttagct ccaggtgctc cacacccatt ccacttgcac   1200
ggtcacgcct tcgctgttgt tagatctgct ggttctacca cctacaacta caacgatcca   1260
atcttccgtg acgttgtctc taccggtact ccagctgctg gtgacaacgt tactattaga   1320
ttccaaactg acaacccagg tccttggttc ttgcattgtc acattgattt ccatttggaa   1380
gccggtttcg ctatcgtttt cgctgaggac gttgctgatg ttaaggctgc taacccagtt   1440
cccaaggctt ggtctgactt gtgtcctatc tacgacggtt tgtccgaagc caaccaa      1497
```

<210> SEQ ID NO 61
<211> LENGTH: 1512
<212> TYPE: DNA
<213> ORGANISM: Trametes versicolor

<400> SEQUENCE: 61

```
gctattggtc cagtcactga cttgaccatc tctaacgccg atgtcactcc tgacggtatc      60
accagagctg ccgttttggc tggtggtgtt tttccaggtc cattgatcac gggcaacaag     120
ggtgatgaat tccaaattaa cgtcatcgac aacttgacca acgaaaccat gttaaagtct     180
accaccatcc actggcatgg tatctttcaa gctggtacca attgggctga cggtgctgct     240
ttcgttaacc aatgtccaat cgccactggt aactccttct tgtacgactt cactgtccca     300
gatcaagccg gtaccttctg gtaccactct cacttgtcca cccaatactg cgacggtttg     360
agaggtccat tggtcgtcta cgacccagat gacgccaatg cttctctata tgacgtcgat     420
gacgatacta ccgttatcac tttggccgac tggtaccaca ctgccgctaa gttgggtcct     480
gccttcccag caggtccaga ttccgtctta atcaacggtt tgggtagatt ctctggtgat     540
ggtggtggtg ccaccaactt gaccgttatc accgtcactc aaggtaagcg ttacagattc     600
agattggttt ccatctcttg tgacccaaac ttcactttca gcattgatgg tcacaacatg     660
accatcattg aagttggtgg tgttaaccat gaagctttgg acgttgattc catccaaatt     720
ttcgctggtc aaagatactc tttcatcttg aacgccaacc aatccatcga taactactgg     780
attcgtgcta tcccaaacac tggtaccact gatactactg gtggcgtcaa ctccgccatc     840
ttgagatatg ataccgccga agaaattgaa ccaaccacca acgctaccac ctctgttatc     900
ccattaactg aaaccgactt ggtcccatta gacaacccag ccgccccagg tgatccacaa     960
gtcggtggtg ttgacttggc catgtccttg gatttttctt tcaacggttc taacttcttc    1020
atcaacaacg aaacctttgt tccacccacc gtcccagttt tgttgcaaat cttgtccggt    1080
gctcaagacg ccgcttcctt gttgcctaat ggttctgtct acactttgcc atccaacagc    1140
accatcgaaa tctctttccc aatcatcacc accgacggtg ccttgaacgc tccaggtgcc    1200
ccacacccat tccacttgca cggtcacact ttctctgttg ttagatctgc cggttcctct    1260
actttcaact acgctaaccc agtcagaaga gacaccgttt ccaccggtaa ctctggtgac    1320
aacgtcacta tcagatttac cactgacaac ccaggtccat ggttcttaca ctgtcacatc    1380
gatttccact tggacgccgg tttcgctatc gtttttgctg aagataccgc tgacactgct    1440
tccgctaacc cagttccaac cgcctggtcc gacttgtgtc caacttacga cgccttggat    1500
tcctccgact tg                                                        1512
```

<210> SEQ ID NO 62
<211> LENGTH: 1755
<212> TYPE: DNA
<213> ORGANISM: Trametes versicolor

<400> SEQUENCE: 62

```
aaggtcccag gtatggacat caagtacgac gtcgttattg tcggttccgg tccaatcggt      60
tgtacttacg ctagagaatt ggttgaagct ggttacaaag tcgctatgtt cgacatcggc     120
gaaatcgact ctggtttgaa gattggtgct cacaagaaaa acactgttga ataccaaaag     180
aacatcgaca agtttgtcaa cgtcatccaa ggtcaattga tgtctgtctc tgttccagtt     240
aacactttag tcattgacac cttgtctcca acttcctggc aagcttcctc tttcttcgtt     300
```

```
agaaacggtt ctaacccaga acaagaccca ttaagaaact tgtccggtca agctgtcact    360

agagttgtcg gtggtatgtc tactcactgg acctgtgcta ctccacgttt cgatagagaa    420

caaagaccat tgttggtcaa ggatgaccaa gacgctgatg acgctgaatg ggatagattg    480

tacaccaagg ctgaatcata tttcaagact ggtaccgacc aattcaagga atccatcaga    540

cacaacttgg tcttgaacaa gttggctgaa gaatacaagg gtcaaagaga cttccaacaa    600

attccattgg ctgccactag aagatctcca accttcgtcg aatggtcaag tgctaacact    660

gttttcgact tgcaaaacag accaaacact gatgctccaa acgaaagatt caacttgttt    720

ccagctgtcg cttgtgaaag agttgttcgt aacacttcca actccgaaat cgaatctttg    780

catatccacg acttgattag cggtgacaga ttcgaaatca aggctgacgt tttcgttttg    840

actgctggtg ctgttcacaa cgcccaattg ttagtcaact ccggtttcgg tcaattgggt    900

agaccagacc cagctaaccc accacaattg ttgccctctt tgggttctta catcactgaa    960

caatctttgg tattttgtca aaccgttatg agcactgaat tgatcgattc cgtcaagtct   1020

gacatgatta tcagaggtaa cccaggtgac ttgggttact ccgtcaccta cactccaggt   1080

gccgaaacta acaagcatcc agactggtgg aacgaaaaag ttaagaacca catgatgcaa   1140

catcaagaag atccattgcc tatcccattc gaggaccctg aaccacaagt taccacctta   1200

ttccaaccat ctcacccatg gcacacccaa attcaccgtg atgccttctc ctacggtgcc   1260

gtccaacaat caatcgacag ccgtttgatc gtcgactgga gattcttcgg tagaactgaa   1320

ccaaaggaag aaaacaaatt gtggttctcc gataaaatta ctgataccta caacatgcca   1380

caaccaactt tcgacttcag attcccagct ggtagaacct ctaaggaagc tgaagatatg   1440

atgactgaca tgtgtgttat gtctgccaag atcggtggtt ttttgccagg ttccttgcca   1500

caattcatgg aaccaggttt ggtcttgcac ttgggtggta cccatagaat gggtttcgac   1560

gaacaagaag ataagtgttg tgtgaatact gactccagag ttttcggttt caagaactta   1620

ttcttgggtg gttgtggtaa catcccaacc gcttacggtg ctaaccctac tttgactgct   1680

atgtccctag ctattaaatc ttgtgaatac attaagaaca acttcacccc atccccattc   1740

accgatcaag ctgaa                                                    1755
```

<210> SEQ ID NO 63
<211> LENGTH: 2247
<212> TYPE: DNA
<213> ORGANISM: Trametes versicolor

<400> SEQUENCE: 63

```
caagtcgccg ctccatacgt cgactctggt aacggtttcg tctttgacgg tgtcactgac     60

ccagttcact ccgtcaccta cggtatcgtt ttgccacaag cttctacttc cactgaattc    120

attggtgaat tcgtcgctcc aaacgaagct caatggatcg gtttggcttt gggtggtgct    180

atgattggta acttgttgtt ggtcgcttgg cctaacggta ataaaattgt ttcctcgcca    240

agatacgcta ctggttacac tttgccagct gcttacgctg gtccaaccat cactcaattg    300

ccttcttcct ccgttaactc cacccactgg aagttcgttt tcagatgcca aaactgtact    360

gcttggaacg gtggttccat cgacccatcc ggtaccggtg ttttcgcttg ggctttctcc    420

aatgtcgctg ttgacgatcc atccgaccca aactcttctt tcgctgaaca caccgatttc    480

ggtttttttcg gtatcaactt tccagatgct caatcctcca actaccaaaa ctacttggct    540

ggtaacgctg gtaccccacc accaacctct gtcccatccg gtccatcctc tactactact    600

accactggtc caactgccac tgctactcct ttcgactaca tcgttgtcgg tgctggtcca    660
```

```
ggtggtttgg ttaccgctga cagattgtcc gaagccggta agaaagtctt gttgttggaa    720

agaggtggtc catctacggc tgaaactggt ggtacttacg atgctacttg ggctaagtcc    780

gcaaacttga ccaagttcga cgtcccaggt ttgttcgaaa ccttgttcac tgacactaac    840

ccattctggt ggtgtaagga caccaatttc tttgctggtt gtttgttggg tggtggtact    900

tctgtcaacg gtgctttgta ctggtaccca aactctagag acttctccac tgcttctggt    960

tggccatcct cttggtctaa ccaccaacca ttcactgata agttgaagca aagattgcca   1020

tccaccgacc acccatctgc cgatggtcaa agatacttag aacaatccgc tactgtcgtc   1080

caacaattgt tgtctggtca aggttactcc caaatcacca tcaacggtaa ccctgactcc   1140

aaggatcacg ttttcggttt ctctgctttc gacttcttga acggtcaacg tgctggttcc   1200

gtcgctactt acttcgaaac tgctttggct agaaagaact tcgtctacaa ggacaacgtc   1260

cttgttactc aagttattag aaacggttct actatcttgg gtgtcagaac taacgataac   1320

accttgggtc cagacggtgt tgtcccattg aacccaaacg gtagagtcat cttgtccggt   1380

ggtagcttcg gtactccacg tattttgttt caatcaggta tcggtccaac cgatatgttg   1440

caaaccgtcc aatccaacgc tcaagctgct gctaacttgc caccacaatc cgaatggatt   1500

gatttgccag tcggtcaatc cgtttctgat aacccttcca tcaacttggt ttttacccac   1560

ccatccatcg acgcttacga caactgggct gatgtttggt ccaacccaag accagctgat   1620

gctcaacaat acttgcagtc tagatccggt gtcttggctg gtgcttcttt gaagttgaac   1680

ttctggagag cttacggtgg ttccgacggt atcactggtt acgctcaagg taccgttaga   1740

ccaggtgctg cttctgttaa cacttccgtc gcttacaacg cttctgaaat tttcactact   1800

actttgtact tgtctaacgg tatccaatcc cgtggtagaa ttggtgtcga cgctaccttg   1860

aacgctaagg ctttggttaa cccatggttg actaactctg ttgataagac cgttttgttg   1920

caagctttgc acgatgttac ttccaccatg aaaaacgtta gtggtttgac tatgatcact   1980

ccagacaaca ctatgactct agaacaatac gttgctgctt acgatccagc taccatgtgt   2040

tctaaccact gggttggtgc tgctaagatg ggtacctctt cctccactgc tgtcgttgac   2100

gaaaacgcta aggtttttaa caccgataac ttgttcatcg tcgacgcctc tatcattcca   2160

tctttgccaa tcggtaaccc acaaggtgtc ttgatgtccg ctgctgaaca agctgtttct   2220

agaattttgg ctctagctgg tggtcct                                       2247
```

<210> SEQ ID NO 64
<211> LENGTH: 1497
<212> TYPE: DNA
<213> ORGANISM: Trametes hirsutus

<400> SEQUENCE: 64

```
gctatcggtc caactgctga tttgaccatt tctaacgctg aagtctcccc agacggtttc     60

gctagacaag ctgttgtcgt caacaacgtt actccaggtc cattggttgc tggtaacaaa    120

ggtgacagat tccaattgaa tgttatcgat aacttgacca accacaccat gttgaagtca    180

acttctatcc actggcacgg tttcttccaa aagggtacca actgggctga tggtccagct    240

ttcgtcaacc aatgtccaat ctcctctggt cactccttct tgtacgactt ccaagtccca    300

gatcaagctg gtaccttctg gtaccactct cacttgtcca ctcaatactg tgacggtttg    360

agaggtccct tcgtcgttta cgatcccaac gacccacatg cttccttgta cgacgttgac    420

aacgatgaca ccgtcatcac cttggccgac tggtaccaca ctgctgctaa attgggtcca    480
```

```
gctttccctt tgggtgccga cgctaccttg atcaacggtt taggtagaag tccatctact    540

accgctgctg acttggccgt tatcaatgtc accaagggta agagatacag atttagattg    600

gtcagcttgt cctgcgaccc aaaccacact ttcagcattg atggtcacga cttgaccatc    660

atcgaagttg attctatcaa cagccaacca ttggtcgtcg actccatcca aatcttcgct    720

gcccaacgtt actccttcgt cttgaacgct gatcaagacg ttggtaacta ttggattaga    780

gctaacccaa acttcggtaa cgtcggtttc gccggtggta tcaactctgc tattttgaga    840

tacgacggtg ccgatccagt tgaaccaacc accactcaaa ccactccaac caagccattg    900

aacgaagtcg acttgcaccc attggctact atggccgtcc caggctcccc agttgcgggt    960

ggtgtcgaca ccgctatcaa catggctttt aacttcaacg gtactaattt cttcattaac   1020

ggtgcttctt tcgtcccacc taccgtccca gttttgttgc aaatcatttc tggtgctcaa   1080

aacgctcaag acttgttgcc aagtggttct gtctactcct tgccaagtaa cgctgacatc   1140

gaaatttcct tcccagccac cgctgctgct ccaggtgccc cacacccatt ccacttgcac   1200

ggtcacgctt tcgccgttgt tagatctgct ggttccactg tttacaacta cgataaccca   1260

atcttccgtg atgtagtttc taccggtacc cctgccgctg gtgataacgt cactattaga   1320

ttccgtactg acaacccagg tccatggttc ttgcactgtc acatcgattt ccacttggaa   1380

gctggtttcg ctgtcgtctt tgctgaggac attcccgatg ttgccagcgc taacccagtc   1440

ccacaagctt ggtctgactt atgtccaatc tacgacgctt tggacgttaa cgaccaa      1497
```

<210> SEQ ID NO 65
<211> LENGTH: 1020
<212> TYPE: DNA
<213> ORGANISM: Bjerkandera adusta

<400> SEQUENCE: 65

```
gtcgcttgtc cagacggtgt taacactgcc accaacgctg cctgttgtgc tttgttcgct     60

gtccgtgatg acattcaaca aaacttgttc gatggtggtg aatgtggtga agaagttcac    120

gaatctttga gattgacttt ccacgatgct atcggtatct ctccatccat cgctgctacc    180

ggtaagttcg gtggtggtgg tgccgatggt agcattatga tcttcgatga catcgaacca    240

aacttccatg ctaacaacgg tgttgacgaa attatctccg ctcaaaagcc attcgtcgct    300

aagcacaaca tgactgccgg tgatttcatt caattcgccg gtgctgttgg tgtttccaac    360

tgtccaggtg ctccacaact atctttcttc ttaggtagac cagctgccac tcaaccagct    420

ccagacggtc tagtcccaga accattcgat tctgttaccg atatcttgaa ccgtttcgct    480

gatgccggtg gtttcactac tcaagaagtt gtctggttgt tggcttctca ctctattgcc    540

gctgccgatc atgtcgaccc aaccatccca ggttccccat tcgattctac cccagaaatc    600

tttgacaccc aattctttgt tgaaactttg ttgaagggta ccttgttccc aggtacttcc    660

ggtaaccaag gggaagtcga atccccattg gctggtgaaa tcagattaca atccgatgcc    720

gacttcgcta gagattctag aactgcttgt gaatggcaat cttttgttaa caaccaacca    780

agaatgcaag ttttgttcaa ggctgctatg caaaagttgt ccatcttggg tcacgatttg    840

actcaaatga tcgactgctc cgacgttatc ccagttccac catccaccgc tgtcagaggt    900

tctcacttgc cagctggtaa cactttagac gatatcgaac aagcctgtgc ttccaccccca   960

ttcccaactt tgaccgccga cccaggtcca gccacttctg ttgctccagt tccaccatct   1020
```

<210> SEQ ID NO 66
<211> LENGTH: 1047

<212> TYPE: DNA
<213> ORGANISM: Bjerkandera adusta

<400> SEQUENCE: 66
gttgcttgtc cagacggtaa gaacaccgct attaacgctg cctgttgctc tttgttcacc 60
gctagagatg acatccaaaa gaacatgttt gatggtggtc aatgtaacga tatcgctcac 120
caagctatca gattgacttt ccatgacgct gtcgccttct ctccaacttt aactgctcaa 180
ggtaagttcg gtggtaacgg ggccgacggt tccattatga ccttcgatac cattgaaacc 240
aatttccacc caaacattgg tttggatgaa attgttaaca ttgaaaagcc attcgctcaa 300
ttccacaaca tgactccagg tgactttatc cacttcgctg gtgctttggc cgtcaccaac 360
tgtccaggtg ctccaacttt aaccttttct atcggtcgtc caccaccagt cgccgctgcc 420
ccagacggtt tggttccaga accatttcac actgccgatc aaatcttcgc tagaatgttg 480
gatgctctac aatttgacga attggaaacc gtctggggtc ttatcgctca cactgtcggt 540
gcctccaatg atgttgaccc atccattcca agaaccccat tcgactctac tccatccatt 600
ttcgatggcc aatttttat tgatacacaa ttgagaggtg aattgttccc aggtcaaggt 660
ggtttgcaag gtgaagtcga atccccattg aagggtcaaa ttagattaca atctgatcac 720
attattgcta gagactctag atccgcctgt gaatggcaat ctttcgctaa cgatcatgat 780
aagttgacca acagatttca atttgtcatc gaaactttgg ccatggttgg tcaagaccca 840
actaatatga tcgactgttc cgaagtcatt cccattccaa aggatttgac cgctgctcaa 900
ttgactccaa tgttcccagc tggtaagact aacgctgacg ttgagcaagc ttgtgctgac 960
accccattcc catccttcgc cactagacca ggtccagcca ccgctgtccc accagtccca 1020
tctgctaaga ccggtgcccc aggttcc 1047

<210> SEQ ID NO 67
<211> LENGTH: 1491
<212> TYPE: DNA
<213> ORGANISM: Trametes cinnabarina

<400> SEQUENCE: 67
gctatcggtc cagtcgctga cttgactttg accaacgctg ctgtttctcc agacggtttc 60
tccagagaag ctgttgttgt caacggtatt actccagctc cattgatcgc cggtcaaaag 120
ggtgacagat ttcaattgaa cgtcatcgac aacttgacca accacactat gttaaaaacc 180
acctccatcc actggcacgg tttcttccaa cacggtacca actgggccga cggtgtttct 240
ttcgtcaacc aatgtccaat cgcttccggt cactctttct tatacgattt ccaagttcca 300
gaccaagctg gtactttctg gtaccactct cacttgtcta cccaatactg tgatggtttg 360
agaggtccat tcgtcgttta cgacccaaac gatccacaag cttctttgta tgatattgac 420
aacgatgata ctgttattac cttggccgac tggtaccacg tcgctgctaa gttgggtcca 480
agattcccat tgggtgctga tgcaaccttg atcaacggtt tgggtagatc cccaggtacc 540
accactgctg acttggctgt tatcaaggtt actcaaggta agagatacag attcagattg 600
gtttctttgt cctgtgatcc aaatcacacc ttctccattg acggtcacac tatgaccgtc 660
atcgaagccg actctgttaa cactcaacca ttggaagttg actctatcca aatcttcgct 720
gctcaaagat actccttcgt tttggacgcc tcccaaccag tcgataacta ctggatcaga 780
gctaacccag ctttcggtaa cgttggtttc gctggtggta tcaactccgc cattttgcgt 840
tacgacggtg ccccagaagt tgaaccaacc accacccaaa ctacttctac caagccattg 900

```
aacgaagctg atttgcatcc attgactcca atgccagtcc caggtagacc agaagctggt     960

ggtgttgaca agccattgaa catggtgttc aacttcaacg gtaccaactt cttcattaac    1020

aaccactcct tcgttccacc atctgtccca gttttgttgc aaatcttgtc cggtgcccaa    1080

gctgctcaag atttggttcc agacggttcc gtctacgtct tgccaagcaa ctcttccatc    1140

gaaatttcct tcccagccac tgcaaacgcc ccaggtaccc cacacccatt ccatttgcat    1200

ggtcacacct tcgctgttgt cagatctgct ggttcctccg aatacaacta cgacaatcct    1260

atcttccgtg acgttgtttc cactggtcaa ccaggtgata acgtcactat cagattccaa    1320

accaacaacc caggtccatg gttcttgcac tgtcacatcg acttccactt ggaagctggt    1380

tttgccgttg tcttggccga agatactcca gacaccgctg ctgttaaccc agtcccacaa    1440

tcctggtccg acttgtgtcc aatttacgac gccttagacc catctgactt g             1491
```

<210> SEQ ID NO 68
<211> LENGTH: 2250
<212> TYPE: DNA
<213> ORGANISM: Trametes cinnabarina

<400> SEQUENCE: 68

```
caagtcgctg ccccatacgt cgattccggt aacggtttcg tctttgacgg tattactgat      60

ccagtttacc acgtcagtta cggtatcgtt ttgccacaag ctaccacttc ctccgaattc     120

atcggtgaaa ttgtcgctcc attggatgct aagtggatcg gtttggcttt gggtggtgct     180

atgatcggtg acctattgat cgtcgcttgg ccaaacggta acgaaattgt ttcctccacc     240

agatatgcta ccgcttacca actgccagat gtttacgctg gtccaactat cactactttg     300

ccttcctcct tggtcaactc cactcactgg aagtttgttt tcagatgtca aaactgtacc     360

tcttgggaag gtggtggtgg tatcgaccca actggtactg gtgtttttgc ttgggcttac     420

tcctctgtcg gtgttgatga cccatctgac ccaaacacca ccttccaaga acacaccgac     480

ttcggtttct tcggtattaa ctttccagac gctcaaaaca gtaactacca aaactacttg     540

caaggcaacg ctggtactcc accaccaacc tctactccat ctggtccaac caccacttcc     600

aagcctaccg gtccaactgc ttctgctacc ccatacgatt acatcattgt cggtgccggt     660

cctggtggta tcattgctgc cgaccgtttg tctgaagctg gtaagaaggt tatcttgttg     720

gaaagaggtg gtccatccac cgctgaaact ggtggtacct actacgctcc atgggctaag     780

tcccaaaact tgactaaatt cgatattcca ggtttgttcg aatctatgtt caccgaccca     840

aacccatggt ggtggtgtaa agacactaac ttcttcgctg gttgtttgtt gggtggtggt     900

acttctgtca acggtgcttt gtactggtta ccatctgacg ctgatttctc taccgccaac     960

ggttggccaa ctaactgggg taaccatgct ccatacacct ccaagttgaa gcaacgtttg    1020

ccatctactg accacccatc cgctgacggt aacagatact tggaacaatc cgctaccgtt    1080

gtctcccaat tgttgcaagg tcaaggttac caacaaatca ccattaacga caacccagat    1140

tacaaggacc atgtctttgg ttactctgct ttcgacttca tcaacggtca aagagctggt    1200

ccagttgcta cctacttcca aactgcttcc gctagaagca acttcgtcta caaggactac    1260

accttggttt cacaagtctt gagaaacggt tccactatca ccggtgtcag aactaacaac    1320

actgctttgg gtccagacgg tatcgtccca ttgaacccaa acggtagagt tattttggct    1380

gctggttctt tcggtacccc tagaatcttg tttcaatctg gtattggtcc aactgacatg    1440

attcaaaccg ttcaatccaa cccaactgcc gctgctaact tgccaccaca atctgaatgg    1500

attaacttgc cagttggtca aggtgtttcc gacaacccat ctattaactt ggttttcacc    1560
```

```
cacccatcca tcgacgctta cgaaaactgg gctgacgttt ggtccaaccc aagaccagct   1620

gacgctcaac aatacttgca atccagatct ggtgttttcg ctggtgcttc cccaaagttg   1680

aacttctgga gagcttacgg tggttccgac ggtaagacca gatatgctca aggtactgtt   1740

agaccaggtg ctgcctccgt caacacttcc gttgcttaca acgcctccca aattttcacc   1800

atcaccgttt acttatctga aggtattacc tccagaggta gattgggtgt cgacgcagct   1860

ttgaacatga aagctattac taccccatgg ttgaccgatc cagttgacaa gactattttg   1920

ttgcaagctt tgcacgacgt tgtttccaac atcaacaacg tccctggttt gaccttgatt   1980

acccccgatc acacccaaac tttggaacaa tacgttgctg cttacgaccc agctaccatg   2040

tgctctaacc actgggtcgg tgctgccaag atcggttcct ccccatctac tgctgttgtt   2100

gacgaaaaca ccaaggtttt taacaccgac aacttattca ttgttgacgc ttctattatc   2160

ccatccttgc cagtcggtaa ccctcacggt gctttgatgt ctgccgctga acaagctgcc   2220

gctaagatct tggctttggc tggtggtcca                                    2250
```

<210> SEQ ID NO 69
<211> LENGTH: 1029
<212> TYPE: DNA
<213> ORGANISM: Phanerochaete chrysosporium

<400> SEQUENCE: 69

```
gccacttgcg caaatggtaa gaccgttggt gacgcaagct gctgtgcctg gtttgatgta     60

ctagacgata ttcaggcaaa catgttccat ggaggtcagt gcggagcgga ggcacacgag    120

tcaattcgcc ttgtatttca cgactctatc gcgatcagcc cggctatgga ggcgaaaggc    180

aagttcggtg gcggtggggc cgatggttca attatgattt tcgacacaat cgagactgca    240

ttccacccca acatcggcct ggatgaagtc gttgctatgc agaaaccgtt cgttcaaaag    300

cacggagtta cacccggcga ctttattgcc ttcgcgggag cggtcgccct gagcaattgt    360

ccaggcgcgc cgcagatgaa cttcttcacc gggcgcaaac cggcaacaca acccgccccc    420

gacggcctgg tgccggagcc attccacacg gtagaccaga tcatcgcaag agtcaacgat    480

gccggggagt tcgacgagct ggagctcgta tggatgctgt cagctcattc ggtcgcagca    540

gtcaacgacg tggatcccac cgttcaggga ttgccattcg acagcactcc ggggattttc    600

gactctcaat tttcgttgga gactcagttc aggggaacat tgttcccagg ttccgggggc    660

aaccagggtg aagtcgagtc aggtatggct ggggaaatac ggatacagac tgatcacact    720

ttagcccgtg actcgcgcac ggcctgcgag tggcagtctt ttgtcggtaa ccaatcgaag    780

ctcgtcgatg attttcagtt catctttctt gcactgaccc agcttggcca ggatcccaac    840

gcaatgactg attgcagtga cgttattcca ttgtccaaac caattccggg gaacgggccc    900

ttctcattct tcccacctgg gaaaagccat tctgatatag aacaggcttg tgccgagaca    960

ccgttccctt ctcttgtcac actgccaggt cccgcaactt cagttgctag gattccacca   1020

cacaaagca                                                           1029
```

<210> SEQ ID NO 70
<211> LENGTH: 1071
<212> TYPE: DNA
<213> ORGANISM: Phanerochaete chrysosporium

<400> SEQUENCE: 70

```
gccgtctgcc cggatggaac aagggtgtcg cacgccgctt gttgcgcgtt cattccttta     60
```

```
gcccaggacc tccaagagac tatattccag aacgaatgcg gtgaggacgc acacgaggtt    120

atccgtttga ccttccatga tgccatcgcg atttcccgct ctcaaggtcc aaaggccggc    180

ggcggtgcgg acggatccat gctactattc cccacagttg aaccgaactt ttccgccaat    240

aatggcatag acgatagtgt caacaatctg attcctttca tgcaaaagca caacacgata    300

tccgctgctg acctcgttca gtttgcaggc gctgtcgccc tgagcaactg ccccggtgcc    360

cctcgacttg aatttctcgc cggccgtcca aacaagacta tcgctgcagt tgacggcctc    420

atccccgagc cccaggacag tgtcacgaag atcctacagc gcttcgagga tgccgggggt    480

tttactccct ttgaagtagt ctcgctgctc gcatctcact ctgtcgctag ggccgacaaa    540

gttgatcaaa ccatcgatgc agcccctttt gactccacac ccttcacttt tgatacgcaa    600

gtgttcttgg aggtcctgct caagggcgtg ggtttcccgg gatcagctaa taacacaggt    660

gaagttgcca gccccccttcc gcttggctct ggtagcgata ctggtgaaat gaggctgcaa    720

agcgactttg ccctcgcgca tgaccctcga accgcctgta tttggcaggg attcgtcaat    780

gagcaggcat ttatggctgc ctcgttccgc gcagctatga gcaagcttgc ggtcctcggc    840

cataatcgaa actctttaat cgattgttcc gacgtagtac ccgtcccgaa acctgctacc    900

ggtcagccag caatgttccc tgcctcgacg ggtcctcaag acctggagtt atcgtgccca    960

tccgagcgat ttcctaccct gacaactcag cctggtgcta gccaatcgct cattgcccat   1020

tgccctgacg gctcaatgtc ctgcccagga gtccagttca atggtccggc g            1071
```

<210> SEQ ID NO 71
<211> LENGTH: 2265
<212> TYPE: DNA
<213> ORGANISM: Phanerochaete chrysosporium

<400> SEQUENCE: 71

```
cagtccgcat cgcaatttac ggatccgacc acgggtttcc agtttactgg aatcaccgat     60

cccgtgcatg atgtcacgta cggtttcgtg tttccaccgc tcgccactag tggggctcaa    120

agcaccgaat tcatcggcga ggttgtcgca cccatcgcgt ctaaatggat cggaatcgcc    180

ctaggtggtg cgatgaacaa cgacttactc ctggtcgcct gggcaaatgg caaccagatc    240

gtcagcagca cgcgctgggc taccggttac gtccagccca cggcctatac tggtactgct    300

acgctgacca ctcttccaga aacgacgatc aatagtacac actggaagtg ggtctttcgt    360

tgccaaggat gtactgaatg gaacaatggc ggtggcattg acgtgacaag ccagggtgtt    420

ctagcctggg catttagcaa tgtcgctgtt gatgacccgt cggatccaca gtcaactttt    480

tcagagcaca cggatttcgg gttctttggc atcgactaca gcaccgccca cagcgccaac    540

tatcagaatt acctgaatgg ggattctggc aatcctacga caacgtccac aaaaccgaca    600

tctacgagct ccagcgtcac tacggggccc accgtttctg ccaccccata cgattatatt    660

attgtcgggg caggcccagg tggaatcatc gccgccgatc gactgagcga ggccggcaag    720

aaggtccttc tgctcgaaag aggtggtcca agcacgaaac aaaccggcgg tacttatgtg    780

gcgccatggg ctacttcctc agggctgacg aaatttgaca tcccgggctt gttcgagtcc    840

ctcttcacag atagcaatcc attctggtgg tgcaaggata ttaccgtctt tgccggttgt    900

ctggttggag gggtactag cgtcaacggc gcactatact ggtatcctaa cgacggagat    960

ttcagcagca gtgtcgggtg gccgtcctca tggactaatc atgcccctta caccagtaaa   1020

ctgagcagca gactaccatc caccgaccat ccttctacgg atggtcaacg ctatctggaa   1080

caaagcttca acgttgtcag tcaacttctc aagggccagg gttacaatca ggctacgatc   1140
```

```
aacgacaatc cgaattataa ggatcatgtc tttggataca gcgccttcga ctttctgaac   1200

ggcaagcgtg ctggtccagt cgccacgtac cttcaaactg ctttggcgcg tcctaatttc   1260

actttcaaga cgaacgtcat ggtttctaat gtcgtccgca acggctccca gattctcgga   1320

gtccaaacca atgatccaac cctaggcccg aacggattca ttccagtaac gccaaagggt   1380

agagtaatcc tctcggctgg cgctttcggt acatcccgca tactattcca aagtggcata   1440

ggaccgactg atatgatcca gaccgtccag tccaatccta cggctgcggc cgcgctgccc   1500

ccgcaaaatc agtggattaa tcttccagtg ggtatgaatg cccaagacaa tccttccata   1560

aatttagtat ttacccatcc gagtatcgac gcctatgaga actgggcgga tgtctggtca   1620

aaccccaggc cagccgatgc tgcacaatac ttggcaaatc agagcggcgt tttcgcgggc   1680

gcttccccta agcttaattt ctggagagct tatagtggct ccgacggatt tacacgatac   1740

gcccaaggca ctgtaaggcc aggagctgcg tccgtcaact cttcccttcc gtataacgcc   1800

agtcaaatct tcaccataac ggtttatctg tctacaggca ttcaatcacg tggtcgaata   1860

ggcatcgatg cggccctgag aggcaccgta ctcacgcccc cttggctggt taatccagtt   1920

gataaaacag tattgcttca ggcgctccac gacgtcgtca gcaacatagg ttccattcca   1980

ggcctaacta tgattacgcc agatgtcact caaacccttg aagagtacgt agatgcatat   2040

gaccctgcta ctatgaactc aaaccattgg gtttcctcga ccactatcgg atcctcaccc   2100

cagtctgcgg tggtcgattc caacgtgaag gtttttggca ctaataacct cttcatcgtg   2160

gatgcgggta taatcccaca tcttcctaca ggtaaccccc aaggtacgct catgtcggcc   2220

gctgagcaag ctgccgcaaa gatactcgcg ctggccgggg gacca                    2265
```

<210> SEQ ID NO 72
<211> LENGTH: 993
<212> TYPE: DNA
<213> ORGANISM: Pleurotus eryngii

<400> SEQUENCE: 72

```
gctacctgtg acgatggtag gacaacggca aacgcagcct gctgcatcct tttccccatc     60

ctcgatgaca tacaagagaa cctgttcgac ggtgcccagt gtggcgaaga ggtccacgag    120

agtctgcgcc tcacttttca tgatgcaatt gggttcagcc ccacactagg cggcggcgga    180

gccgacggct ctatcatcgc gttcgatacg atcgaaacca atttcccggc caatgcgggc    240

attgacgaga ttgtgtcagc acagaaacct ttcgttgcaa agcataatat cagcgcggga    300

gattttattc agttcgctgg tgcagttggt gtgtcaaatt gccctggcgg cgtccgtatc    360

ccgtttttcc tcggcaggcc agacgcagtg gcagcgagcc ctgaccacct tgtccccgaa    420

cccttcgata gcgttgattc cattcttgcg agaatggggg acgccggctt ttccccggtg    480

gaggtggtct ggctgctcgc ttcgcattcc atcgcggcag cggataaagt tgatccgtcc    540

attcctggta cgccttttga ttcaacccct ggtgttttcg acagccaatt cttcatagaa    600

acccaactga aaggccgtct gttcccgggc acggcagata acaagggtga ggcacagtcg    660

cctttgcaag gcgaaatccg tttgcagagc gatcatctgc ttgcaaggga cccacagaca    720

gcctgtgaat ggcaatcaat ggtgaacaat cagccgaaga ttcagaaccg cttcgctgcc    780

acgatgtcga agatggctct gcttggtcag gataaaacga aactgatcga ctgctccgat    840

gttatcccaa ctccgcccgc tttggttggc gcagcgcacc ttccagctgg gttctccctc    900

agcgatgttg agcaggcgtg cgcagctacc cctttcccgg ctctgaccgc agaccccggc    960
```

cctgtcacct cagttccgcc cgttcctgga tcc 993

<210> SEQ ID NO 73
<211> LENGTH: 1539
<212> TYPE: DNA
<213> ORGANISM: Pleurotus eryngii

<400> SEQUENCE: 73
agcatcggcc ctcgtggtac gctgaacatc gcaaacgaag tgattaagcc agacggcttc 60
agtcgttcgg cggtactagc cggtggctca tacccggggc ctcttatcaa aggcgaaacc 120
ggtgaccgct ttcagatcaa tgtcgtaaac aagctcgcgg acacttccat gccggtagat 180
acgtccatcc attggcatgg gatctttgta agggggcaca actgggccga cggacctgcg 240
atggtgactc agtgtccgat tgttccaggt cacagcttcc tttacgattt cgaaatcccc 300
gaccaggccg gcacattctg gtaccattcc caccttggta cccaatactg cgatggattg 360
cgcggtccgt tcgtggttta ttctaaaaat gaccctcata agcgactcta cgacgtggat 420
gacgagtcaa cggtactgac ggtcggcgac tggtatcacg caccttcgtt gtcgttatcc 480
ggagttccgc acccggacag cactttattt aacggtttgg gcagatcgct aaatggtccc 540
gcttctccat tatacgtcat gaacgtcgtt aagggcaagc gttataggat tcgcctgatc 600
aacacgagct gtgattcaaa ctaccaattc agcatcgacg gtcacgcatt cactgtgatc 660
gaggcggacg gagaaaatac acaacctctt caagtcgatc aagtccagat tttcgctggc 720
cagaggtaca gcttggtact taatgccaac caagcggtcg gcaattactg gatccgggct 780
aaccctaact ccggggaccc tggctttgca aaccaaatga actcagccat tctccgatat 840
aaaggtgcca ggaacgttga tccgactaca ccagaacgta acgcgacaaa cccgttgcgg 900
gaatacaact tgcgcccgct aataaaggaa ccggctcccg gaaagccttt tcctggcggc 960
gcggaccaca acattaatct taacttcgcc ttcgatccag cgactgtgct tttacggcc 1020 aacaattata ccttcgtgcc gccaacggtg cccgtccttc tccagatcct atcgggcacc 1080
cgcgacgctc atgatttggc acccgctggg agtatctacg acattaagtt gggcgacgtg 1140
gtcgaggtga caatgcctgc acttgttttt gcgggaccgc accccatgca cttgcacggt 1200
cattcatttg ccgttgtcag gagcgcagga tcctctacat acaactatga aaacccggtg 1260
cggcgggatg tagtgagcat cggcgacgat ccaactgaca acgttacaat tcgcttcgtg 1320
gcggataacg cggggccttg gtttttacac tgccatattg attggcacct cgacctggga 1380
ttcgcggtgg tttttgcaga aggcgtgaac caaacagcag tggcgaaccc ggtgccggaa 1440
gcatggaacg acctctgccc catttacaac tcgtcgaacc cgagtaaact tctgatgggt 1500
acgaatgcaa ttggccgcct ccacgcccct ttgaaggcg 1539

<210> SEQ ID NO 74
<211> LENGTH: 1698
<212> TYPE: DNA
<213> ORGANISM: Pleurotus eryngii

<400> SEQUENCE: 74
gcggattttg attatgtggt tgtcggtgct gggaatgctg gcaacgtggt tgcagcgcgg 60
ttgacagagg accctgatgt gtcggtcttg gttctggaag cgggagtctc ggacgagaat 120
gtgctcggtg cagaggcccc cctccttgcc ccgggcctgg tcccgaactc aatcttcgat 180
tggaattaca cgacgactgc tcaagcggga tataatggga gatcgatcgc ttacccgagg 240
ggacgcatgc tcggcggttc ctcaagcgtc cactatatgg ttatgatgcg tggttcgacc 300

```
gaggattttg acaggtatgc tgcggtgaca ggggatgaag gttggaattg ggacaacatt    360

cagcaattcg tccgaaaaaa tgagatggtt gtccctcctg ctgataacca caacacgtct    420

ggcgaattta tcccggcggt acatggaact aatggctccg tcagcatatc acttcccggt    480

ttcccgacac cgttggatga ccgcgtcctc gctactaccc aagagcagag cgaggaattc    540

ttctttaacc cggacatggg aacgggccat ccactgggta taagctggtc gattgcctcg    600

gtgggaaacg gccagcggtc tagctcgtcg acggcgtatc tccgccctgc acagagccgt    660

ccgaacctgt cggtcctcat aaatgcccag gtgaccaagt tagtaaacag cggtacaacc    720

aatggactgc cggcatttcg atgtgtcgag tacgctgagc aggagggggc cccaactact    780

acggtatgcg caaagaagga ggttgtcctt tccgctggat ccgtcggaac tccaatccta    840

cttcaactta gcggcatcgg ggatgaaaac gacctgtcct cagttgggat tgatacgata    900

gtcaataacc cttccgttgg gcgcaatctc tctgaccatc ttctcctccc cgcagctttc    960

ttcgtcaatt ccaaccagac gttcgataac atcttccgcg actcttctga gttcaatgtg   1020

gaccttgacc aatggaccaa cacgcgcact ggtccattga ctgccctgat tgctaaccac   1080

ctcgcatggt tgcgcctgcc gtcgaattcc agcatcttcc agacattccc cgatccggcc   1140

gccgggccaa actctgctca ttgggaaact atattctcaa atcagtggtt ccaccctgca   1200

attccgcggc ccgacacggg ctcatttatg tcggttacga atgccctgat cagccctgtt   1260

gcccgtggag atataaagct cgccactagc aatccgttcg acaagcctct catcaatccc   1320

caatatctct ctactgaatt cgacattttc actatgattc aggccgtgaa gtcaaacttg   1380

agatttctct caggtcaagc ttgggctgac ttcgtcatac gtccgttcga cccccggctc   1440

cgcgacccaa ctgatgacgc ggctatcgag agctacattc gtgataatgc gaacacgatc   1500

ttccatccag tcgggactgc ttcaatgtcc ccgagaggcg cttcgtgggg tgtcgttgac   1560

ccagatctta aggtcaaagg agttgatggg ttacggatcg tcgacggctc aatcctgcca   1620

ttcgccccta atgcacatac ccaagggccg atctatttgg tcggcaaaca gggagccgat   1680

ctaataaagg ccgatcag                                                 1698
```

<210> SEQ ID NO 75
<211> LENGTH: 1014
<212> TYPE: DNA
<213> ORGANISM: Ceriporiopsis subvermispora

<400> SEQUENCE: 75

```
gcgacatgcc cagacggtaa caccgtcacg aatgaagctt gctgctttct ctttcccatt     60

cttgaagata ttcaggccaa cctctttaat ggcggggagt gcggctcgga ggctcatgag    120

tccctgcggc tcacgttcca tgacgcaatc ggcttctctc cagccctgac agctcagggt    180

caattcggcg gtggtggcgc cgatggttcg gtaattacct ttgcttctat tgagactgct    240

tacgctgcga atgcaggcat cgaagatata gtcgccgaac aagcgcagtt tgtcgcgaag    300

tataacgtgt cagccgggga ctttgtacag ttcgctgggg ccgtgggctt gtcgaactgc    360

cctggagccc cacagctcga ttttgttatc ggtcgtccgg cggccacggc tgcatcaccg    420

gacggtttag tccctgagcc tttcgataac gttacttcga tcttggcccg tttcaacgat    480

gctggcgggt tcgacccaca acatgtcgtc tggctcttaa gtagtcattc cgttgcagct    540

gctgagctgg tcgaccctag tatccccggc gccccgtttg atagtactcc tggcttgttt    600

gacacacagt tctttattga gacacaactg accgggaccc tctggccagg tacggcaaat    660
```

```
aaccaagggg aggtcgagtc cccgctcctg ggcgaaattc ggcttcaatc cgattttctg    720

ctggccagag ataaccgcac cgcatgcgag tggcaatcgt tcgctaacga tttgtccagg    780

cagcagacgc tttttaaggc ggcaatgtca acgctggcca caataggtca agatacgtcc    840

acactgactg actgttcgga tgtgattccc gtaccagctg ctccggttgg caccccacat    900

ttccctgccg gtttgactaa tgctgacgta gaccaagcct gcacgaccgc agcctttccc    960

acgctttcca cggatccagg ccccgctaca tctgtggcac ccgtccccac ggct         1014
```

<210> SEQ ID NO 76
<211> LENGTH: 996
<212> TYPE: DNA
<213> ORGANISM: Pleurotus ostreatus

<400> SEQUENCE: 76

```
gccacttgcg cgggtggcca ggttacggcg aacgcggctt gttgcgtgct tttccccctc     60

atggaagatc tgcagaagaa tcttttcgat gacggggcat gcggagagga tgcgcatgaa    120

gccctgcgtc ttacatttca tgacgcaatt ggcttcagtc ctagccgagg agtcatgggt    180

ggcgctgatg gaagcgttat cacgttttcc gatacagaag ttaattttcc agcaaaccta    240

ggcattgacg agattgttga agcggagaaa ccttttcttg caaggcacaa catttcggcg    300

ggggatctcg tccatttcgc aggaacgctc gctgtaacca actgccccgg agcgccacga    360

attccttttt ttctcggccg gccgcccgct aaggcagcca gcccaatcgg gctggtgccg    420

gagcctttcg acaccatcac tgacattctc gcaagaatgg atgatgcggg atttgtgtcc    480

gtggaggttg tgtggctgct ctcagcccat agtgtcgcag cagctgacca tgtcgatgag    540

acaatccccg gcaccccttt tgactctacg ccaaacctgt ttgactccca aatctttatc    600

gagactcaat tgcgaggaat tagctttcct ggcacgggag gaaaccacgg agaagttcag    660

agccccctca aaggagaaat gcgactccaa tccgatcacc tcttcgcccg cgacgaccgt    720

acaagttgtg agtggcaaag catgacaaat gaccaacaga aaatccagga tcgctttagc    780

gatacgctgt tcaagatgtc gatgctcggt caaaatcagg acgccatgat cgattgctca    840

gacgtaattc ctgtcccggc agcgctcgtc acaaaacctc atcttcccgc gggcaagtct    900

aaaaccgacg ttgagcaggc atgtgcgacg ggagcttttc cggctttagg agcggatcca    960

ggtcctgtga cctccgttcc gcgcgtgccc cccgcc                              996
```

<210> SEQ ID NO 77
<211> LENGTH: 1038
<212> TYPE: DNA
<213> ORGANISM: Trametes versicolor

<400> SEQUENCE: 77

```
gtcgcgtgcc ctgatggcgt taacaccgca acaaatgctg cttgttgcca actcttcgcg     60

gtccgtgagg atctccaaca gaatctgttc cacggagggc tctgtactgc tgaggctcat    120

gagagcctgc gactcacatt ccatgatgct attgcgatca gtccggcttt ggaggcgcaa    180

ggaatcttcg gcggaggtgg cgctgatggt tcgattgcta tattcccaga gatcgagact    240

aatttccacc cgaatatagg gctcgatgag ataattgaac tccaaaagcc atttatcgca    300

cgccataata tctctgttgc cgacttcatt caattcgccg gtgccattgg cgccagtaac    360

tgtgccggag ctccccaact agcggctttc gtggggcgta aggatgcgac ccaacccgcc    420

ccggatggac tagttcctga gccatttcac acgcctgacc aaatattcga ccgtcttgct    480

gatgcatcgc agggggagtt cgatcctata ctcacagttt ggctcctcac tgcgcataca    540
```

```
gtagctgcag ccaatgatgt ggaccccacg aagtcgggcc tccccttcga tagcacaccc    600

gagctatggg atactcaatt cttcctcgag acacagctca ggggaacctc ttttccaggt    660

tcaggcggaa atcaaggcga ggttgagtcc cctctggccg gggaaatgag actccagtca    720

gaccacacaa tcgctcgcga cagtcgtact gcttgcgagt ggcagtcctt cgtcgacaac    780

caaccgaagg cgcagcaaat gttccaattc gtattccacg atctcagcat cttcggccag    840

gatatcaaca ctctagttga ctgtaccgaa gtcgttccta tccccgcaga tcctcaagga    900

catacacatt ttcctgcagg gttgtcaaac gcagatatcg aacaggcgtg tgctgagact    960

cccttcccga ccttccccac ggacccagga cctaaaactg cagtcgctcc ggtccctaag   1020

cctcctgcgg cccgtaag                                                 1038
```

<210> SEQ ID NO 78
<211> LENGTH: 924
<212> TYPE: DNA
<213> ORGANISM: Armoracia rusticana

<400> SEQUENCE: 78

```
caacttaccc ctaccttcta cgacaattca tgtcctaacg tctcaaacat agtacgggac     60

actattgtca atgagttacg atcggaccct aggatcgccg cgagcatcct tcgtcttcac    120

ttccacgact gctttgttaa cggttgtgac gcatcgatct tgttagacaa cacaacatca    180

tttcgaacag agaaagatgc gtttgggaac gcaaactcgg cgcgcggatt tcctgtgatt    240

gacagaatga aggcggccgt ggagagtgca tgcccaagaa ctgtatcctg cgcagatctg    300

cttaccattg cagctcaaca atctgttact ttggcaggag gtccctcttg gagggttcct    360

ttgggacgtc gagacagcct acaagcattt ttagatctcg cgaatgcgaa tcttccagct    420

ccattcttca cacttccaca acttaaggat tcttttagaa atgttggttt aaaccgttct    480

tctgatctcg ttgccctcag cggtggtcac acatttggta aaaatcaatg tcgatttatt    540

atggacagat tatacaactt cagcaacacc gggttacccg accctaccct caacactact    600

taccttcaaa ctcttcgtgg actatgtccc cttaatggca acctaagcgc cttggtcgac    660

ttcgatctgc gtacgccaac aattttcgat aacaaatact atgtgaatct tgaagagcaa    720

aaaggtctca tccagagtga tcaagagttg ttctctagcc ccaatgccac tgacacaatc    780

ccactagtga gatcatttgc taatagcaca caaacattct tcaacgcgtt tgtggaggcc    840

atggatagga tgggaaacat tacacctctt acaggaactc aaggacaaat caggttgaac    900

tgtagggtgg tgaactccaa ctct                                           924
```

<210> SEQ ID NO 79
<211> LENGTH: 680
<212> TYPE: DNA
<213> ORGANISM: artificial sequence
<220> FEATURE:
<223> OTHER INFORMATION: GAL10-GAL1

<400> SEQUENCE: 79

```
ttatattgaa ttttcaaaaa ttcttacttt ttttttggat ggacgcaaag aagtttaata     60

atcatattac atggcattac caccatatac atatccatat acatatccat atctaatctt    120

acttatatgt tgtggaaatg taaagagccc cattatctta gcctaaaaaa accttctctt    180

tggaactttc agtaatacgc ttaactgctc attgctatat tgaagtacgg attagaagcc    240

gccgagcggg tgacagccct ccgaaggaag actctcctcc gtgcgtcctc gtcttcaccg    300
```

```
gtcgcgttcc tgaaacgcag atgtgcctcg cgccgcactg ctccgaacaa taaagattct    360

acaatactag cttttatggt tatgaagagg aaaaattggc agtaacctgg ccccacaaac    420

cttcaaatga acgaatcaaa ttaacaacca taggatgata atgcgattag ttttttagcc    480

ttatttctgg ggtaattaat cagcgaagcg atgatttttg atctattaac agatatataa    540

atgcaaaaac tgcataacca ctttaactaa tactttcaac attttcggtt tgtattactt    600

cttattcaaa tgtaataaaa gtatcaacaa aaaattgtta atatacctct atactttaac    660

gtcaaggaga aaaaactata                                                680


<210> SEQ ID NO 80
<211> LENGTH: 2175
<212> TYPE: DNA
<213> ORGANISM: artificial sequence
<220> FEATURE:
<223> OTHER INFORMATION: AGA1

<400> SEQUENCE: 80

actgaaaatt acattgcaag caactgccat gatggcgaag accaactttc ctaatggcaa     60

acgcgtttgc gatccactgc ccatatattg gctaattgtt accattgatg aagtttggta    120

ttgtatggag attgaagtag tggaaacttc tgtagtggta acagatgttt gtagagaaga    180

gggagcagat gatgatgaga ggaaaataga agataccgtc ggagtcaatg atgaagattc    240

aatagtcgat tccacagagg tagatggtgt agagatagat gttgcggaaa gtgatgatgt    300

agaggcagat attgtagcaa tagctgtgga agaagtgggt tgtaaaatct ctgatgttga    360

agaaatttga agtgtggtaa ctggtgactg ttcgacactt agtgatgata cagaactgaa    420

tagcaaaata gtactgtcag aggataatgt agcagacaag gaggaggatg aaaggaccga    480

tgtcgataat aagtgtgatg attgttcttg agattctgag tcaatgcttg atgtactcgt    540

ggcttcactt acactagtcg aaatggttga ggtacctgaa gatgttacat gatacttacc    600

ggtagcgtgc ttattgaaat cttcatccga agttgtcatt gaacttaccc aactctttgt    660

ggatgtggtc tgctgtgtta cagaacttga tgaagctgtt tgcacggaag aatacgagtg    720

tgacgtttca gcacatgtgg agcatgcata tgaggattca accgttgagg tgcttacaga    780

agttgcgacg tttttagtgg acatttttat agaagatgta atcaaacttg ttgtctgcga    840

gggcatgcaa gactcgtgag tgcagactgt agcgtctgtt gtaaccgttt catgcatact    900

ggttaatgtg ctagtctcag attcagagct ataaggacac catgtcgtat acattgtagt    960

gactccacta acagtggtga aatatgtaga catggaaaat gatgggatag tagtagaaat   1020

tgaggatttg gtgatatatt cagacgaact ttgtgaacta acagttgttt caacagttga   1080

agaagtcata gaaggagttg caacatttga cgaagtcgaa gggacggagt aaacaggtgt   1140

ggatgggctg tataatgaca cagacgttga tgaagatgct atagaggagc caagggatga   1200

agttgaatca gtaaaagtag agctaataga tgttgaactt ggagaagtgg aagccaaagt   1260

tggagatgaa gaagtcaaac ttggggatgt agatgttgaa tatgaagaag tggaagtgga   1320

gcttgcagaa gtagatttag aacttggaga tgtagatgtt gaacttgatg aggtagatgt   1380

agagcttgga gatgtagatg tcgaacttga tgaggtagat gtagaacttt gggatgtaga   1440

tgtagaactt gaagatgtgg atgtcaaact tgaagatgtg gatgtcgaac ttggagatgt   1500

agatgtcgaa cttgatgagg tagatgtcga acttgatgag gtagatgtcg aacttgatga   1560

ggtagatgta gagcttggag atgtagatgt agagcttgga gatgtagatg tcgaacttag   1620

ggaggtagta gttggattgg acgatgttgt actcgaaagt gtagaggtga caggtgagat   1680
```

-continued

```
tatagaggca cttgatggtt caatggcgct ggatgatacc acggttgtag ttcctacttc   1740

ggataatgag ctgatagcgg ttgtgtgaca agtagggcaa atatatgaag tgaacttgga   1800

agtcacagat aaggtggtgg ttggcaacgt cgatgacgaa ggacatgcct catgggagca   1860

gacttctgta gataatgtca aagtactaaa tctggatagg gtagtagcgt acgatattga   1920

aggacttatt tcggcagcag atgaagtgga taccgtcaat ggacaccaag tcgtatacaa   1980

tgtcgtagtg ccagcttgaa cgatagtgga tgtggagact agcgcgggtg aaactgtagt   2040

tgtaacaacc ccatttgcat cgtttgtctt ggttatcgtc actagaatcg tttctggatc   2100

agatgccaag gcaatattag ttaatcccaa caatattgtg aacaggtagg taaaatgagc   2160

gaaagataat gtcat                                                     2175


<210> SEQ ID NO 81
<211> LENGTH: 261
<212> TYPE: DNA
<213> ORGANISM: artificial sequence
<220> FEATURE:
<223> OTHER INFORMATION: AGA2

<400> SEQUENCE: 81

atgcagttac ttcgctgttt ttcaatattt tctgttattg cttcagtttt agcacaggaa     60

ctgacaacta tatgcgagca aatcccctca ccaactttag aatcgacgcc gtactctttg    120

tcaacgacta ctattttggc caacgggaag gcaatgcaag gagtttttga atattacaaa    180

tcagtaacgt ttgtcagtaa ttgcggttct caccccctcaa caactagcaa aggcagcccc   240

ataaacacac agtatgtttt t                                              261
```